US007978774B2

(12) United States Patent
Feher

(10) Patent No.: US 7,978,774 B2
(45) Date of Patent: Jul. 12, 2011

(54) INTERNET GSM, CDMA, OFDM, WI-FI WIRELESS AND WIRED MULTIMODE SYSTEMS

(76) Inventor: Kamilo Feher, El Macero, CA (US)

( * ) Notice: Subject to any disclaimer, the term of this patent is extended or adjusted under 35 U.S.C. 154(b) by 840 days.

(21) Appl. No.: 11/875,925

(22) Filed: Oct. 21, 2007

(65) Prior Publication Data
US 2008/0043868 A1 Feb. 21, 2008

Related U.S. Application Data

(63) Continuation of application No. 11/197,670, filed on Aug. 3, 2005, now Pat. No. 7,548,787.

(51) Int. Cl.
*H04L 27/28* (2006.01)
(52) U.S. Cl. .......................... 375/260; 375/219
(58) Field of Classification Search .................. 375/219, 375/260, 267, 295, 316
See application file for complete search history.

(56) References Cited

U.S. PATENT DOCUMENTS

| | | | |
|---|---|---|---|
| 3,702,476 A | 11/1972 | Nathanson |
| 3,944,926 A | 3/1976 | Feher |
| 4,030,033 A | 6/1977 | Bibl et al. |
| 4,229,821 A | 10/1980 | De Jager et al. |
| 4,339,724 A | 7/1982 | Feher |
| 4,350,879 A | 9/1982 | Feher |
| 4,531,221 A | 7/1985 | Chung et al. |
| 4,567,602 A | 1/1986 | Kato et al. |
| 4,584,880 A | 4/1986 | Matzuk |
| 4,644,565 A | 2/1987 | Seo et al. |
| 4,720,839 A | 1/1988 | Feher et al. |
| 4,742,532 A | 3/1988 | Walker |
| 4,745,628 A | 5/1988 | McDavid et al. |
| 4,852,090 A | 7/1989 | Borth |
| 4,945,549 A | 7/1990 | Simon et al. |
| 4,962,510 A | 10/1990 | McDavid et al. |
| 5,084,903 A | 1/1992 | McNamara et al. |
| 5,107,260 A | 4/1992 | Meissner |
| 5,157,686 A | 10/1992 | Omura et al. |
| 5,185,765 A | 2/1993 | Walker |
| 5,282,222 A | 1/1994 | Fattouche et al. |

(Continued)

FOREIGN PATENT DOCUMENTS

AU   2005335219   1/2008

(Continued)

OTHER PUBLICATIONS

Feher, K.—U.S. Appl. No. 09/370,360, filed Aug. 9, 1999.

(Continued)

*Primary Examiner* — Chieh M. Fan
*Assistant Examiner* — Freshteh N Aghdam

(57) ABSTRACT

Internet, wireless and wired multimode systems. Processing, modulating, transmitting and receiving internet provided and location finder signals. Cross-correlator, transmit baseband filter and modulator for cross-correlating, filtering and modulating in-phase and quadrature-phase signal, and providing modulated signal to a transmitter. Orthogonal Frequency Division Multiplex (OFDM) or Orthogonal Frequency Division Multiple Access (OFDMA), Wi-Fi, spread spectrum, Code Division Multiple Access (CDMA), time division multiplexed (TDM), Time Division Multiple Access (TDMA) and Global Mobile System (GSM) processors and baseband filters for providing OFDM, OFDMA, TDM, TDMA, Bluetooth, spread spectrum CDMA and GSM system signals to transmitter and diversity receiver. Diversity receiver systems. Demodulator for demodulating, filtering and processing diversity system received signal. Receive baseband filter is intentionally mismatched to the transmit baseband filter. Receiver and demodulator baseband filter provides received baseband mis-match filtered cross-correlated in-phase and quadrature-phase signal.

19 Claims, 30 Drawing Sheets

U.S. PATENT DOCUMENTS

| | | |
|---|---|---|
| 5,299,228 A | 3/1994 | Hall |
| 5,313,173 A | 5/1994 | Lampe |
| 5,345,439 A | 9/1994 | Marston |
| 5,359,521 A | 10/1994 | Kyrtsos et al. |
| 5,430,416 A | 7/1995 | Black et al. |
| 5,479,448 A | 12/1995 | Seshadri |
| 5,488,631 A | 1/1996 | Gold et al. |
| 5,491,457 A | 2/1996 | Feher |
| 5,497,777 A | 3/1996 | Abdel-Malek et al. |
| 5,535,432 A | 7/1996 | Dent |
| 5,539,730 A | 7/1996 | Dent |
| 5,550,881 A | 8/1996 | Sridhar et al. |
| 5,564,076 A | 10/1996 | Auvrey |
| 5,572,516 A | 11/1996 | Miya et al. |
| 5,596,333 A | 1/1997 | Bruckert |
| 5,608,722 A | 3/1997 | Miller |
| 5,668,880 A | 9/1997 | Alajajian |
| 5,745,480 A | 4/1998 | Behtash et al. |
| 5,757,858 A | 5/1998 | Black et al. |
| 5,778,024 A | 7/1998 | McDonough |
| 5,784,402 A * | 7/1998 | Feher ............................ 375/130 |
| 5,794,159 A | 8/1998 | Portin |
| 5,815,525 A | 9/1998 | Smith et al. |
| 5,818,827 A | 10/1998 | Usui et al. |
| 5,842,140 A | 11/1998 | Dent et al. |
| 5,850,392 A | 12/1998 | Wang et al. |
| 5,903,592 A | 5/1999 | Itaya |
| 5,909,435 A | 6/1999 | Apelewicz |
| 5,909,460 A | 6/1999 | Dent |
| 5,915,207 A | 6/1999 | Dao et al. |
| 5,930,303 A | 7/1999 | Walker |
| 5,933,421 A | 8/1999 | Alamouti et al. |
| 5,943,361 A | 8/1999 | Gilhousen et al. |
| 5,982,819 A | 11/1999 | Womack et al. |
| 5,999,519 A | 12/1999 | Basile et al. |
| 6,006,105 A | 12/1999 | Rostoker et al. |
| 6,008,703 A | 12/1999 | Perrott et al. |
| 6,014,551 A | 1/2000 | Pesola et al. |
| 6,035,212 A | 3/2000 | Rostoker |
| 6,067,018 A | 5/2000 | Skelton et al. |
| 6,075,973 A | 6/2000 | Greeff et al. |
| 6,088,585 A | 7/2000 | Schmitt et al. |
| 6,101,174 A | 8/2000 | Langston |
| 6,101,224 A | 8/2000 | Lindoff et al. |
| 6,107,959 A | 8/2000 | Levanon |
| 6,128,330 A | 10/2000 | Schilling |
| 6,138,330 A | 10/2000 | Schilling |
| 6,167,099 A * | 12/2000 | Rader et al. ................... 375/347 |
| 6,177,861 B1 | 1/2001 | MacLellan et al. |
| 6,192,070 B1 | 2/2001 | Poon et al. |
| 6,195,563 B1 | 2/2001 | Samuels |
| 6,198,777 B1 | 3/2001 | Feher |
| 6,208,875 B1 | 3/2001 | Damgaard et al. |
| 6,216,012 B1 | 4/2001 | Jensen |
| 6,240,133 B1 | 5/2001 | Sommer et al. |
| 6,249,252 B1 | 6/2001 | Dupray |
| 6,256,508 B1 | 7/2001 | Nakagawa et al. |
| 6,269,246 B1 | 7/2001 | Rao et al. |
| 6,282,184 B1 | 8/2001 | Lehman et al. |
| 6,298,244 B1 | 10/2001 | Boesch et al. |
| 6,321,090 B1 | 11/2001 | Soliman |
| 6,332,083 B1 | 12/2001 | Shi et al. |
| 6,389,055 B1 | 5/2002 | August et al. |
| 6,393,294 B1 | 5/2002 | Perez-Breva et al. |
| 6,418,324 B1 | 7/2002 | Doviak et al. |
| 6,424,867 B1 | 7/2002 | Snell et al. |
| 6,430,695 B1 | 8/2002 | Bray et al. |
| 6,445,749 B2 * | 9/2002 | Feher ............................ 375/298 |
| 6,448,022 B1 | 9/2002 | Walker |
| 6,466,163 B2 | 10/2002 | Naruse et al. |
| 6,470,055 B1 | 10/2002 | Feher |
| 6,522,895 B1 | 2/2003 | Montalvo |
| 6,535,320 B1 | 3/2003 | Burns |
| 6,535,561 B2 | 3/2003 | Boesch et al. |
| 6,539,253 B2 | 3/2003 | Thompson et al. |
| 6,546,044 B1 | 4/2003 | Dent et al. |
| 6,574,211 B2 | 6/2003 | Padovani et al. |
| 6,577,229 B1 | 6/2003 | Bonneau et al. |
| 6,591,084 B1 | 7/2003 | Chuprun et al. |
| 6,665,348 B1 * | 12/2003 | Feher ............................ 375/259 |
| 6,711,440 B2 | 3/2004 | Deal et al. |
| 6,741,187 B2 | 5/2004 | Flick |
| 6,745,126 B1 * | 6/2004 | Pavlak et al. .................. 701/213 |
| 6,748,021 B1 | 6/2004 | Daly |
| 6,748,022 B1 | 6/2004 | Walker |
| 6,757,334 B1 | 6/2004 | Feher |
| 6,772,063 B2 | 8/2004 | Ihara et al. |
| 6,775,254 B1 | 8/2004 | Willenegger et al. |
| 6,775,371 B2 | 8/2004 | Elsey et al. |
| 6,788,946 B2 | 9/2004 | Winchell et al. |
| 6,807,564 B1 | 10/2004 | Zellner et al. |
| 6,823,181 B1 | 11/2004 | Kohno et al. |
| 6,834,073 B1 | 12/2004 | Miller et al. |
| 6,842,617 B2 | 1/2005 | Williams et al. |
| 6,865,395 B2 | 3/2005 | Riley |
| 6,876,310 B2 | 4/2005 | Dunstan |
| 6,876,859 B2 | 4/2005 | Anderson et al. |
| 6,879,584 B2 | 4/2005 | Thro et al. |
| 6,879,842 B2 | 4/2005 | King et al. |
| 6,889,135 B2 | 5/2005 | Curatalo et al. |
| 6,897,952 B1 | 5/2005 | Hagler |
| 6,901,112 B2 | 5/2005 | McCorkle |
| 6,906,996 B2 | 6/2005 | Ballantyne |
| 6,907,291 B1 | 6/2005 | Snell et al. |
| 6,928,101 B2 | 8/2005 | Feher |
| 6,963,659 B2 | 11/2005 | Tumey et al. |
| 6,968,014 B1 | 11/2005 | Bobier |
| 6,999,759 B2 * | 2/2006 | Harris et al. ................... 455/418 |
| 7,035,344 B2 | 4/2006 | Feher |
| 7,043,268 B2 | 5/2006 | Yukie et al. |
| 7,057,512 B2 | 6/2006 | Stilp |
| 7,068,738 B2 | 6/2006 | Lee et al. |
| 7,079,584 B2 | 7/2006 | Feher |
| 7,103,085 B1 | 9/2006 | Dabak et al. |
| 7,110,433 B2 | 9/2006 | Feher |
| 7,133,456 B2 | 11/2006 | Feher |
| 7,133,471 B2 | 11/2006 | Feher |
| 7,162,236 B2 | 1/2007 | Dorenbosch et al. |
| 7,228,136 B2 | 6/2007 | Myllymaki |
| 7,236,883 B2 | 6/2007 | Garin et al. |
| 7,245,668 B2 | 7/2007 | Feher |
| 7,260,366 B2 | 8/2007 | Lee et al. |
| 7,260,369 B2 | 8/2007 | Feher |
| 7,263,133 B1 | 8/2007 | Miao |
| 7,280,810 B2 | 10/2007 | Feher |
| 7,286,592 B2 | 10/2007 | Pietila et al. |
| 7,321,783 B2 | 1/2008 | Kim |
| 7,356,343 B2 | 4/2008 | Feher |
| 7,359,449 B2 | 4/2008 | Feher |
| 7,376,180 B2 | 5/2008 | Feher |
| 7,415,066 B2 | 8/2008 | Feher |
| 7,418,028 B2 | 8/2008 | Feher |
| 7,421,004 B2 | 9/2008 | Feher |
| 7,426,248 B2 | 9/2008 | Feher |
| 7,440,488 B2 | 10/2008 | Feher |
| 7,440,516 B2 | 10/2008 | Kim et al. |
| 7,450,628 B2 | 11/2008 | Feher |
| 7,457,385 B2 | 11/2008 | Feher |
| 7,466,975 B2 | 12/2008 | Feher |
| 7,483,492 B2 | 1/2009 | Feher |
| 7,545,883 B2 | 6/2009 | Feher |
| 7,548,787 B2 | 6/2009 | Feher |
| 7,555,054 B2 | 6/2009 | Feher |
| 7,558,313 B2 | 7/2009 | Feher |
| 7,558,574 B2 | 7/2009 | Feher |
| 7,561,881 B2 | 7/2009 | Feher |
| 7,593,481 B2 | 9/2009 | Feher |
| 7,593,733 B2 | 9/2009 | Feher |
| 7,603,125 B2 | 10/2009 | Feher |
| 7,627,320 B2 | 12/2009 | Feher |
| 7,627,340 B2 | 12/2009 | Leedom, Jr. |
| 7,630,717 B2 | 12/2009 | Feher |
| 7,693,229 B2 | 4/2010 | Feher |
| 7,711,368 B2 | 5/2010 | Feher |
| 7,720,488 B2 | 5/2010 | Feher |
| 7,725,114 B2 | 5/2010 | Feher |
| 7,738,608 B2 | 6/2010 | Feher |

| | | |
|---|---|---|
| 7,769,386 B2 | 8/2010 | Feher |
| 7,783,291 B2 | 8/2010 | Feher |
| 7,787,882 B2 | 8/2010 | Feher |
| 7,805,143 B2 | 9/2010 | Feher |
| 7,809,374 B2 | 10/2010 | Feher |
| 2001/0016013 A1 | 8/2001 | Feher |
| 2001/0020912 A1 | 9/2001 | Naruse et al. |
| 2002/0001337 A1 | 1/2002 | Chauncey et al. |
| 2002/0063622 A1 | 5/2002 | Armstrong et al. |
| 2002/0085641 A1 | 7/2002 | Baum |
| 2002/0086684 A1 | 7/2002 | Pande et al. |
| 2002/0188575 A1* | 12/2002 | Freeny, Jr. ............ 705/72 |
| 2002/0193108 A1 | 12/2002 | Robinett |
| 2003/0063683 A1 | 4/2003 | Macfarlane Shearer et al. |
| 2003/0134664 A1 | 7/2003 | Zancewicz |
| 2003/0147471 A1 | 8/2003 | Simon et al. |
| 2003/0179833 A1 | 9/2003 | Porco et al. |
| 2004/0013166 A1 | 1/2004 | Goodings |
| 2004/0017858 A1 | 1/2004 | Rozenblit et al. |
| 2004/0081248 A1 | 4/2004 | Parolari |
| 2004/0196923 A1 | 10/2004 | Feher |
| 2004/0203377 A1 | 10/2004 | Eaton et al. |
| 2004/0203715 A1 | 10/2004 | Camp, Jr. |
| 2004/0208243 A1 | 10/2004 | Feher |
| 2004/0253955 A1 | 12/2004 | Love et al. |
| 2005/0068918 A1 | 3/2005 | Mantravadi et al. |
| 2005/0090266 A1 | 4/2005 | Sheynblat |
| 2005/0093584 A1 | 5/2005 | Meacham |
| 2005/0094589 A1 | 5/2005 | Camp, Jr. |
| 2005/0097595 A1 | 5/2005 | Lipsanen et al. |
| 2005/0175116 A1 | 8/2005 | Feher |
| 2005/0181810 A1 | 8/2005 | Camp, Jr. |
| 2005/0185699 A1 | 8/2005 | Feher |
| 2005/0185700 A1 | 8/2005 | Pietila et al. |
| 2005/0195769 A1 | 9/2005 | Kaewell et al. |
| 2005/0202809 A1 | 9/2005 | Lappetelainen et al. |
| 2005/0232135 A1 | 10/2005 | Mukai et al. |
| 2006/0050625 A1 | 3/2006 | Krasner |
| 2006/0072646 A1 | 4/2006 | Feher |
| 2006/0072647 A1 | 4/2006 | Feher |
| 2006/0072684 A1 | 4/2006 | Feher |
| 2006/0083320 A1 | 4/2006 | Feher |
| 2006/0087432 A1 | 4/2006 | Corbett |
| 2006/0088121 A1 | 4/2006 | Feher |
| 2006/0135183 A1 | 6/2006 | Zavada et al. |
| 2006/0146913 A1 | 7/2006 | Feher |
| 2006/0274838 A1 | 12/2006 | Feher |
| 2006/0293078 A1 | 12/2006 | Qi et al. |
| 2007/0030116 A1 | 2/2007 | Feher |
| 2007/0032220 A1 | 2/2007 | Feher |
| 2007/0032246 A1 | 2/2007 | Feher |
| 2007/0032250 A1 | 2/2007 | Feher |
| 2007/0032266 A1 | 2/2007 | Feher |
| 2007/0032832 A1 | 2/2007 | Feher |
| 2007/0036203 A1 | 2/2007 | Feher |
| 2007/0053471 A1 | 3/2007 | Feher |
| 2007/0053472 A1 | 3/2007 | Feher |
| 2007/0202890 A1 | 8/2007 | Feher |
| 2007/0265018 A1 | 11/2007 | Feher |
| 2008/0031126 A1 | 2/2008 | Feher |
| 2008/0031310 A1 | 2/2008 | Feher |
| 2008/0043868 A1 | 2/2008 | Feher |
| 2008/0056399 A1 | 3/2008 | Feher |
| 2008/0057886 A1 | 3/2008 | Feher |
| 2008/0062856 A1 | 3/2008 | Feher |
| 2008/0161043 A1 | 7/2008 | Feher |
| 2008/0181151 A1 | 7/2008 | Feher |
| 2008/0188240 A1 | 8/2008 | Feher |
| 2008/0205535 A1 | 8/2008 | Feher |
| 2008/0212656 A1 | 9/2008 | Feher |
| 2008/0214164 A1 | 9/2008 | Feher |
| 2008/0219362 A1 | 9/2008 | Feher |
| 2008/0219385 A1 | 9/2008 | Feher |
| 2008/0240070 A1 | 10/2008 | Feher |
| 2008/0253275 A1 | 10/2008 | Feher |
| 2008/0253353 A1 | 10/2008 | Feher |
| 2008/0281585 A1 | 11/2008 | Feher |
| 2009/0061852 A1 | 3/2009 | Feher |
| 2009/0066667 A1 | 3/2009 | Feher |
| 2009/0076803 A1 | 3/2009 | Feher |
| 2009/0092114 A1 | 4/2009 | Feher |
| 2009/0098852 A1 | 4/2009 | Feher |
| 2009/0240308 A1 | 9/2009 | Feher |
| 2009/0247187 A1 | 10/2009 | Feher |
| 2009/0270113 A1 | 10/2009 | Feher |
| 2009/0310591 A1 | 12/2009 | Feher |
| 2010/0029284 A1 | 2/2010 | Feher |
| 2010/0067595 A1 | 3/2010 | Feher |
| 2010/0124920 A1 | 5/2010 | Feher |
| 2010/0208852 A1 | 8/2010 | Feher |

FOREIGN PATENT DOCUMENTS

| | | |
|---|---|---|
| AU | 2005335219 | 1/2010 |
| CN | 2005 8005 1233.3 | 1/2008 |
| DE | 212005000081.6 | 3/2008 |
| JP | 2005-020493 | 1/2005 |
| JP | 2005-086581 | 3/2005 |
| JP | 2008-523857 | 1/2008 |
| KE | K 344 | 9/2009 |
| KR | 10-2008-7002382 | 1/2008 |
| MX | A/2008/001123 | 1/2008 |
| NZ | 565452 | 1/2008 |
| RU | 2008107948 | 10/2005 |
| RU | 8107948 | 2/2008 |
| RU | 2008107948 | 2/2008 |
| SG | 200800527-4 | 10/2005 |
| SG | 8005274 | 11/2008 |
| SG | 200800527-4 | 11/2008 |
| WO | WO 95/23485 | 8/1995 |
| WO | WO 97/30524 | 8/1997 |
| WO | WO 99/09721 | 2/1999 |
| WO | PCT/US99/17995 | 8/1999 |
| WO | PCT/US99/19909 | 8/1999 |
| WO | PCT/US2005/035931 | 10/2005 |
| WO | PCT/US2006/000486 | 7/2006 |
| WO | PCTUS2006000486 | 7/2006 |
| WO | WO/2006/074386 | 7/2006 |
| ZA | 2008/00922 | 12/2008 |

OTHER PUBLICATIONS

Feher, K.—U.S. Appl. No. 09/370,361, filed Aug. 9, 1999.
Feher, K.—U.S. Appl. No. 09/370,362, filed Aug. 9, 1999.
Feher, K. U.S. Appl. No. 60/095,943, filed Aug. 10, 1998.
Feher, K. U.S. Appl. No. 60/098,612, filed Aug. 31, 1998.
Feher, K.—U.S. Appl. No. 10/831,562, filed Apr. 23, 2004.
Feher, K.—U.S. Appl. No. 10/831,724, filed Apr. 24, 2004.
Feher, K. U.S. Appl. No. 60/615,678, filed Oct. 5, 2004.
Feher, K. U.S. Appl. No. 90/007,305 reexamination of US Pat. 6,665,348 Certificate issued Jan. 10, 2006, filed Dec. 19, 2004.
Feher, K. U.S. Appl. No. 11/023,279, filed Dec. 22, 2004.
Feher, K. U.S. Appl. No. 11/102,896, filed Dec. 22, 2004.
Feher, K. U.S. Appl. No. 11/023,254, filed Dec. 28, 2004.
Feher, K. U.S. Appl. No. 11/105,295, filed Apr. 14, 2005.
Feher, K. U.S. Appl. No. 11/107,516, filed Apr. 18, 2005.
Feher, K.: U.S. Appl. No. 11/197,610, filed Aug. 3, 2005.
Feher, K.: U.S. Appl. No. 11/197,670, filed Aug. 3, 2005.
Feher, K.: U.S. Appl. No. 11/197,609, Aug. 3, 2005.
Feher, K. U.S. Appl. No. 90/007,687, filed Aug. 22, 2005, reexamination application of US Pat. 6,470,055.
Feher, K. U.S. Appl. No. 90/007,688, filed Aug. 22, 2005, reexamination application of: US Pat. 6,757,334.
Feher, K.: U.S. Appl. No. 11/294,656, filed Dec. 5, 2005.
Feher, K. U.S. Appl. No. 11/299,344, filed Dec. 10, 2005.
Feher, K. U.S. Appl. No. 11/323,976, filed Dec. 30, 2005.
Feher, K. U.S. Appl. No. 11/410,492, filed Apr. 25, 2006.
Feher, K. U.S. Appl. No. 11/413,687, filed Apr. 28, 2006.
Feher, K. U.S. Appl. No. 11/413,984, filed Apr. 29, 2006.
Feher, K. U.S. Appl. No. 60/831,512, filed Jul. 18, 2006.
Feher, K. U.S. Appl. No. 11/502,720, filed Aug. 10, 2006.
Feher, K.: U.S. Appl. No. 11/534,675, filed Sep. 25, 2006.
Feher, K.: U.S. Appl. No. 11/552,491, filed Oct. 24, 2006.
Feher, K.: U.S. Appl. No. 11/552,936, filed Oct. 25, 2006.
Feher, K.: U.S. Appl. No. 11/745,201, filed May 7, 2007.

Feher, K.: U.S. Appl. No. 11/766,766, filed Jun. 21. 2007, Cont. of U.S. Appl. No. 11/197,610.
Feher, K.: U.S. Appl. No. 11/866,995, filed Oct. 3, 2007, Cont. of U.S. Appl. No. 11/197,609.
Feher, K.: U.S. Appl. No. 11/867,688, filed Oct. 5, 2007, Cont. of U.S. Appl. No. 11/197,609.
Feher, K.: U.S. Appl. No. 11/868,858, filed Oct. 8, 2007, Cont. of U.S. Appl. No. 11/197,609.
Feher, K.: U.S. Appl. No. 11/871,076, filed Oct. 11, 2007.
Feher, K.: U.S. Appl. No. 11/872,007, filed Oct. 13, 2007.
Feher, K.: U.S. Appl. No. 11/872,527, filed Oct. 15, 2007.
U.S. Appl. No. 11/866,995, filed Oct. 3, 2007, Feher, K.
U.S. Appl. No. 11/875,925, filed Oct. 21, 2007, Feher, K.
U.S. Appl. No. 11/924,263, filed Oct. 25, 2007, Feher, K.
U.S. Appl. No. 11/926,144, filed Oct. 29, 2007, Feher, K.
U.S. Appl. No. 11/927,686, filed Oct. 30, 2007, Feher, K.
U.S. Appl. No. 11/924,893, filed Oct. 26, 2007, Feher, K.
U.S. Appl. No. 11/929,447, filed Oct. 30, 2007, Feher, K.
U.S. Appl. No. 11/930,159, filed Oct. 31, 2007, Feher, K.
U.S. Appl. No. 11/932,458, filed Oct. 31, 2007, Feher, K.
U.S. Appl. No. 11/937,467, filed Nov. 8, 2007, Feher, K.
U.S. Appl. No. 12/014,692, filed Jan. 15, 2008, Feher, K.
U.S. Appl. No. 12/047,117, filed Mar. 12, 2008, Feher, K.
U.S. Appl. No. 12/058,299, filed Mar. 28, 2008, Feher, K.
U.S. Appl. No. 12/099,113, filed Apr. 7, 2008, Feher, K.
U.S. Appl. No. 12/102,147, filed Apr. 14, 2008, Feher, K.
U.S. Appl. No. 12/115,936, filed May 6, 2008, Feher, K.
U.S. Appl. No. 12/125,741, filed May 22, 2008, Feher, K.
U.S. Appl. No. 12/252,215, filed Oct. 15, 2008, Feher, K.
U.S. Appl. No. 12/255,515, filed Oct. 21, 2008, Feher, K.
U.S. Appl. No. 12/271,089, filed Nov. 14, 2008, Feher, K.
U.S. Appl. No. 12/324,378, filed Nov. 26, 2008, Feher, K.
U.S. Appl. No. 12/334,493, filed Dec. 14, 2008, Feher, K.
U.S. Appl. No. 12/335,351, filed Dec. 15, 2008, Feher, K.
3GPP TS 25.213 V6.0.0 (Dec. 2003) $3^{rd}$ Generation Partnership Project ; Technical Specification Group Radio Access Network Spreading and Modulation (FDD) (Release 6) 29 pages.
3GPP TS 05.04 V8.4.0 (Nov. 2001) Technical Specification Group GSM/EDGE Radio Access Network; Digital cellular telecommunications system (Phase 2+); Modulation (Release1999); 3GPP:$3^{rd}$ Generation Partnership Project; (10 pages).
Brown, C., Feher, K: "A reconfigurable modem for increased network capacity and video, voice, and data transmission over GSM PCS", IEEE Transactions on Circuits and Systems for Video Technology, pp. 215-224; vol. 6 , No. 2, Apr. 1996 (10pages).
Brown, C.W.:"New Modulation and Digital Synchronization Techniques for Higher Capacity Mobile and Personal Communications Systems" Ph.D. Thesis University of California, Davis, Nov. 1996 pp. i-vii;138-190; 269-272; 288-289;291.
Brown, C., Feher, K. : "A Flexible Modem Structure for Increased Network Capacity and Multimedia Transmission in GSM PCS", Proceedings of the Fifteenths Annual Joint Conference of the IEEE Computer and Communication Societies (INFOCOM '96), 1996 (8 pages).
Furuscar, A. et al .: "EDGE: Enhanced Data Rates for GSM and TDMA /136 Evolution" IEEE Personal Communications , Jun. 1999 , pp. 56-66.
Qualcomm : "MSM 6275 Chipset Solution", Qualcomm CDMA Technologies, San Diego, CA, 2004 (8 pages). Copyright 2004 Qualcomm.
Qualcomm : "MSM 6300 Chipset Solution", Qualcomm CDMA Technologies, San Diego, CA, 2004 (8 pages). Copyright 2004 Qualcomm.
Baisa , N. "Designing wireless interfaces for patient monitoring equipment", RF Design Magazine Apr. 2005, www.rfdesign.com (5 pages).
Hickling, R.M.: "New technology facilitates true software-defined radio"RF Design Magazine Apr. 2005, www.rfdesign.com (5 pages).
Feher, K.: "Wireless Digital Communications: Modulation & Spread Spectrum Applications", Prentice Hall, Upper Saddle River, NJ 07458, Copyright 1995, Book ISBN No. 0-13-098617-8 (pp. front page; copyright page; pp. 164-177; 461-471; and 475-483).

Holma, H., Toskala, A.: "WCDMA for UMTS Radio Access for Third Generation Mobile Communications", Second Edition, John Wiley & Sons Ltd. Chichester, West Sussex, England , Copyright 2002 , ISBN 0-470-84467-1 (pp. front page;copyright page; pp. xv-xvi; 1-4; 90-95; 199-201; and 235-236).
Tuttlebee, W.:"Software Defined Radio: Baseband Technology for 3G Handsets and Basestations", John Wiley & Sons, Ltd., Chichester, West Sussex, England, Copyright 2004 , ISBN 0-470-86770-1 (pp. front page; copyright page; pp. 1-3; 8-15; 34-39; and 274-279).
Dobkin,D.M and Wandinger, T.: "A Radio Oriented Introduction to Radio Frequency Identification"—RFID Tutorial , High Frequency Electronics, Jun. 2005 , Copyright 2005 Summit Technical Media (6 pages).
Dale Setlak : "Fingerprint sensors in Wireless handsets" a presentation at the EOEM Design Expo Jun. 22, 2005, Wireless OEM Design Expo Online Conference & Exhibition , http://www.reedbusinessinteractive.com/eoem/index.asp (38 pages).
Kato, S. and Feher, K.: "XPSK: A new cross-correlated phase shift keying modulation technique", IEEE Trans. Commun., vol. COM-31, No. 5, May 1983, (pp. 701-707).
Perrott et al.,: "A 27-mW CMOS Fractional-N Synthesizer Using Digital Compensation for 2.5-Mb/s GFSK Modulation", IEEE Journal of Solid-State Circuits, Vo.32, No. 12, Dec. 1997, (pp. 2048-2060 ).
Jian et al.,: "An Efficient IF Architecture for Dual-Mode GSM/W-CDMA Receiver of a Software Radio," . . . 1999 International Workshop on Mobile Multimedia Communications, IEEE, Nov. 15-17, 1999 San Diego ,CA(pp. 21-24).
Mangold et al.,: Software-definable Implementation of a Dual Mode TD-CDMA/DCS 1800 Transceiver Communication Summit, vol. 1, Jun. 1998, ( 5 pages).
Morrison, I. S. "ACE-8PSK: Band-Limited 8PSK With an Almost Constant Envelope", Tenth International Conference on Digital Satellite Communications, May 15-19, 1995, Brighton, UK. (pp. 325-331).
Hyunchol Shin: "GSM RF Transmitter Design", Kewangwoon University, Seoul, Korea. Presented at PERC, ICU Aug. 19, 2004 (40 slides).
Grieco, D.M. & Schilling, D.L.: "The Capacity of Broadband CDMA Overlaying a GSM Cellular System", IEEE Vehicular Technology Conference, Jun. 8-10, 1994, Stockholm, Sweden , 1994 IEEE (pp. 31-35).
Malkemes et al.,: "An Interoperable PACS and DCS1900 Subscriber Unit Radio Architecture", Sixth IEEE International Symposium, PIMRC'95: Personal Indoor and Mobile Radio Communication, Sep. 27-29, 1995, Toronto, Ont. Canada, 1995 IEEE (pp. 1149-1154).
Bitkom: "RFID White Paper Technology, Systems, and Applications", Bitkom German Association for Information Technology, German Version published Aug. 2005, and English Version published Dec. 2005. The English Version published Dec. 2005 has been used in Applicant's search.
Nokia: Nokia 5140i phone; Nokia 5140i NFC Shell User Guide"Issue 1.0, May 4, 2006; Nokia 6131 NFC User Guide in English" Issue 1, Feb. 6, 2007; Nokia Field Force Solution is an easy-to-use, flexible management tool especially designed to help enterprise improve their mobile and field-based business operations Copyright 2007.
Quorum articles and publications downloaded from www.quorumsystems.com on Jun. 24, 2007, including: Why Convergence? The Sereno Platform. Sereno QS1000, QS 2000 and QS 3000, Copyright 2006 Quorum.
Kellerer, W. et al. "A communication gateway for infrastructure-independent 4G wireless access", this paper appears in: Communications Magazine, IEEE Publication Date: Mar. 2002 vol. 40, Issue: 3 pp. 126-131.
Spiegel, S.J. and Kovacs, I.G. "An efficient integration of GPS and WCDMA radio front-ends", IEEE Transactions on Microwave Theory and Techniques, vol. 52, Issue 4, Apr. 2004 pp. 1125-1131.
Walker, H.R. : "Understanding Ultra Narrowband Modulation" from Microwaves and RF Dec. 1, 2003 downloaded from: http://www.highbeam.com/doc/1P3-523237701.html.
Feher, K.—U.S. Appl. No. 09/732,953, filed Dec. 7, 2000.
Feher, K.—U.S. Appl. No. 10/831,562, filed Jul. 23, 2002.

Feher, K. U.S. Appl. No. 90/007,305, filed Dec. 19, 2004, reexamination of US Pat. 6,665,348 Certificate issued Jan. 10, 2006.
Feher, K. U.S. Appl. No. 11/023,254, filed Dec. 22, 2004.
Feher, K.: U.S. Appl. No. 11/197,609, filed Aug. 3, 2005.
Feher, K.: U.S. Appl. No. 11,294,656, filed Dec. 5, 2005.
Feher, K.: U.S. Appl. No. 11/766,766, filed Jun. 21, 2007, Cont. of U.S. Appl. No. 11/197,610.
Feher, K.: U.S. Appl. No. 11/866,995, filed Oct. 3, 2007, Cont. of 11/197,609.
Feher, K.: U.S. Appl. No. 11/867,688, filed Oct. 5, 2007, Cont. of 11/197,609.
Feher, K.: U.S. Appl. No. 11/868,858, filed Oct. 8, 2007, Cont. of 11/197,609.
3GPP TS 25.213 V6.0.0 (Dec. 2003) $3^{rd}$ Generation Partnership Project ; Technical Specification Group Radio Access Network Spreading and Modulation (FDD) (Release 6) 28 pages.
Hickling, R.M.: "New technology facilitates true software—defined radio"RF Design Magazine Apr. 2005, www.rfdesign.com (5 pages).
Dobkin,D.M. and Wandinger, T.: "A Radio Oriented Introduction to Radio Frequency Identification"—RFID Tutorial , High Frequency Electronics, Jun. 2005 , Copyright 2005 Summit Technical Media (6 pages).
U.S. Appl. No. 09/370,360, filed Aug. 9, 1999, Feher, K.
U.S. Appl. No. 09/370,361, filed Aug. 9, 1999, Feher, K.
U.S. Appl. No. 09/370,362, filed Aug. 9, 1999, Feher, K.
U.S. Appl. No. 09/385,693, Feher, K.
U.S. Appl. No. 60/095,943, filed Aug. 10, 1998, Feher, K.
U.S. Appl. No. 60/098,612, filed Aug. 31, 1998 Feher, K.
U.S. Appl. No. 60/615,678, filed Oct. 5, 2004 Feher, K.
U.S. Appl. No. 90/007,305, filed Dec. 19, 2004 reexamination of US Pat. 6,665,348 Certificate issued Jan. 10, 2006.
U.S. Appl. No. 90/007,687, filed Aug. 22, 2005 Feher, K. reexamination application of US Pat. 6,470,055.
U.S. Appl. No. 90/007,688, filed Aug. 22, 2005 Feher, K. reexamination of: US Pat.6,757,334.
U.S. Appl. No. 11/927,686, filed Oct. 30, 2007 Feher, K.
U.S. Appl. No. 11/930,159, filed Oct. 31, 2007 Feher, K.
U.S. Appl. No. 11/937,467, filed Nov. 8, 2007 Feher, K.
U.S. Appl. No. 12/753,802, filed Apr. 2, 2010 Feher, K.
Tuttlebee, W. :"Software Defined Radio: Baseband Technology for 3G Handsets and Basestations", John Wiley & Sons, Ltd., Chichester, West Sussex, England, Copyright 2004 , ISBN 0-470-86770-1 (pp. front page; copyright page; pp. 1-3; 8-15; 34-39; and 274-279).
Feher, K. U.S. Appl. No. 90/007,305, filed Dec. 19, 2004 reexamination of US Pat. 6,665,348 Certificate issued Jan. 10, 2006.
Feher, K. U.S. Appl. No. 90/007,687, filed Aug. 22, 2005 reexamination application of US Pat. 6,470,055.
Feher, K. U.S. Appl. No. 90/007,688, filed Aug. 22, 2005 reexamination application of: US Pat.6,757,334.
U.S. Appl. No. 12/467,995, filed May 15, 2009, Feher, K.
U.S. Appl. No. 12/471,293, filed May 22, 2009, Feher, K.
U.S. Appl. No. 12/495,714, filed Jun. 30, 2009, Feher, K.
U.S. Appl. No. 12/577,215, filed Oct. 12, 2009, Feher, K.
U.S. Appl. No. 12/623,403, filed Nov. 21, 2009.
U.S. Appl. No. 12/753,802, filed Apr. 2, 2010, Feher, K.
U.S. Appl. No. 12/767,802, filed Apr. 27, 2010, Feher, K.

* cited by examiner

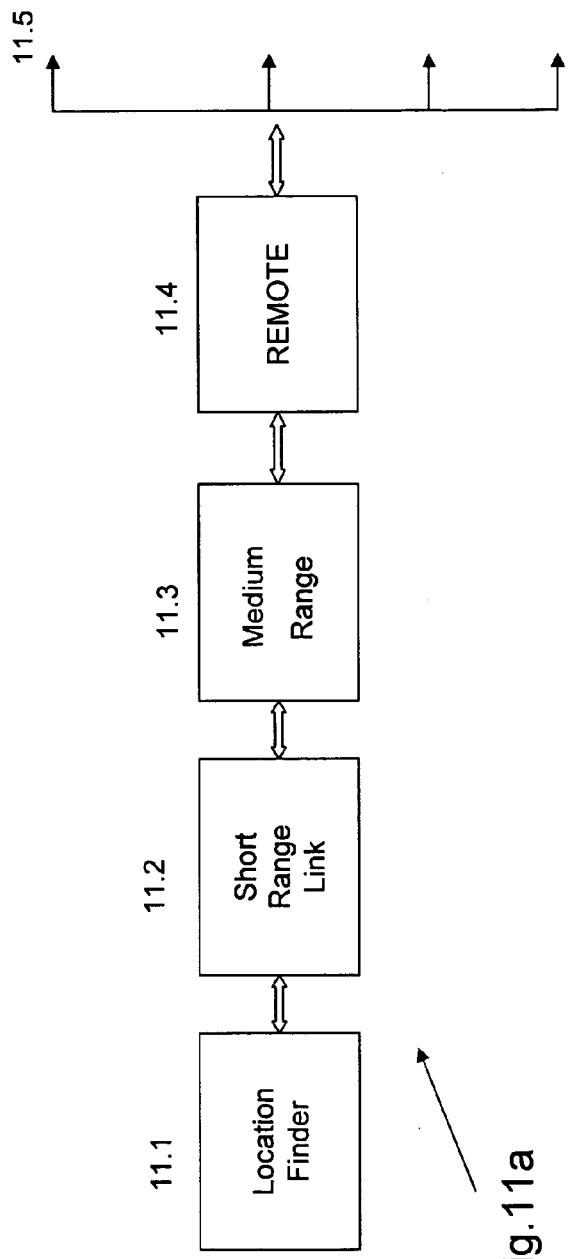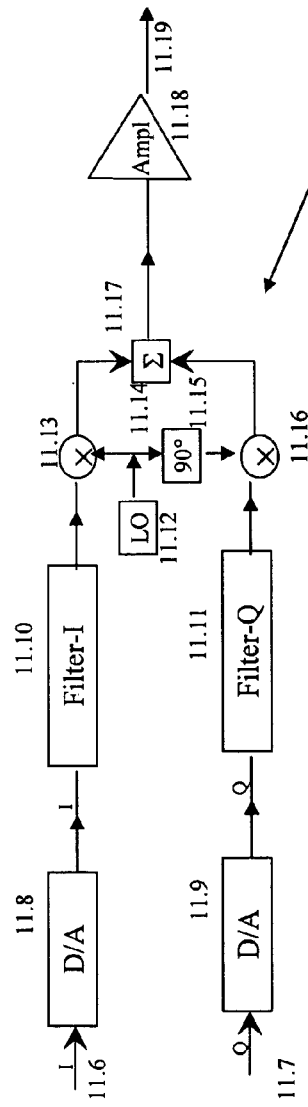
FIG. 11

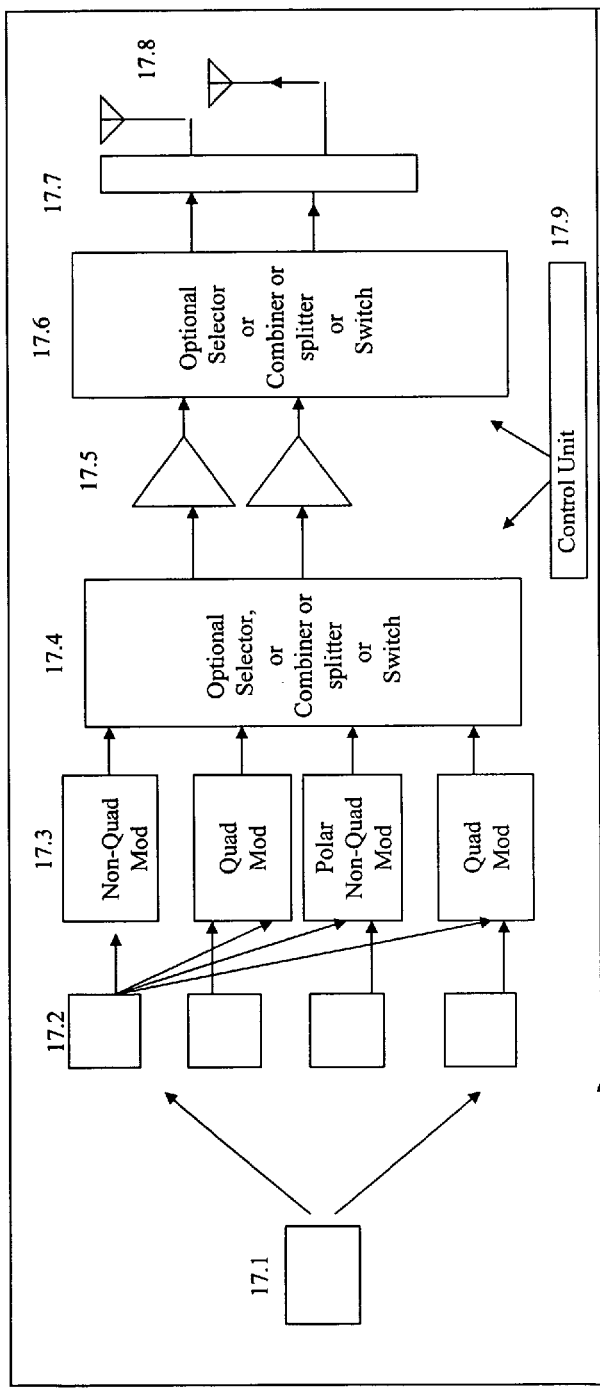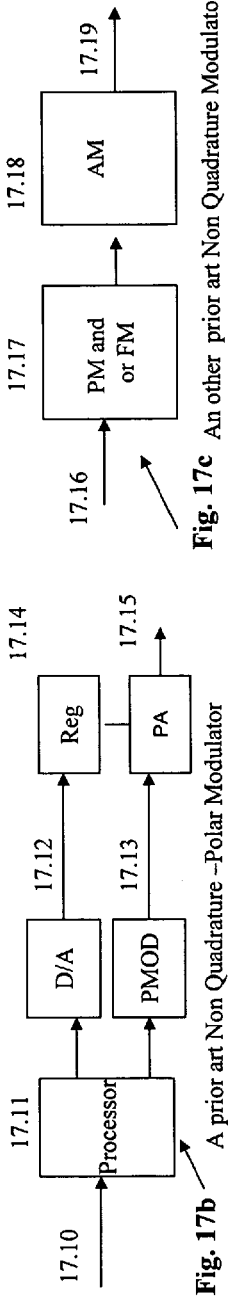
Fig. 17a Multi-mode quad and non-Quad modulators, including polar modulators
Fig. 17b A prior art Non Quadrature –Polar Modulator
Fig. 17c An other prior art Non Quadrature Modulator
0 MED Feher, Aug.3,05

INTERNET GSM, CDMA, OFDM, WI-FI WIRELESS AND WIRED MULTIMODE SYSTEMS

RELATED CO-PENDING U.S. AND PCT INTERNATIONAL APPLICATIONS

The current application is filed as a continuation application of U.S. utility patent application Ser. No. 11/197,670, which was submitted to the USPTO and filed on Aug. 3, 2005. Applicant's co-pending U.S. patent application Ser. No. 11/413,984, filed on Apr. 29, 2006, also claims the benefit of application Ser. No. 11/197,670.

Applicant's co-pending international patent application PCT US2005/035931, entitled: "Multiuse location finder, communication, medical, control system", was submitted and filed Oct. 6, 2005, with the Patent Cooperation Treaty, PCT-USPTO claiming priorities of U.S. application Ser. Nos. 11/197,609, 11/197,610 and 11/197,670, filed on Aug. 3, 2005. In this continuation application, Applicant corrected certain typographical errors which were noticed by Applicant in the parent patent application. The aforementioned applications are included herewith by reference.

RELATED CO-PENDING U.S. PATENT APPLICATIONS

The following three (3) related U.S. patent applications, submitted by Applicant/Inventor Kamilo Feher, are co-pending:

U.S. utility patent application Ser. No. 11/197,610, Ref No. (56), entitled "Location finder, tracker, communication and remote control system", submitted to the United States Patent and Trademark Office (USPTO) on Aug. 3, 2005.

U.S. utility patent application Ser. No. 11/197,670, Ref No. (57), entitled "Medical diagnostic and communication system", submitted to the United States Patent and Trademark Office (USPTO) on Aug. 3, 2005.

U.S. utility patent application Ser. No. 11/197,609, Ref. No. (58), entitled "Multimode communication system", submitted to the United States Patent and Trademark Office (USPTO) on Aug. 3, 2005.

CITED REFERENCES

Partial List of Relevant Literature

Several references, including issued United States patents, pending US patents, and other references are identified herein to assist the reader in understanding the context in which the invention is made, some of the distinctions of the inventive structures and methods over that which was known prior to the invention, and advantages of this new invention, the entire contents of which being incorporated herein by reference. This list is intended to be illustrative rather than exhaustive.

All publications including patents, pending patents, documents, published papers, articles and reports contained, listed or cited in these mentioned publications and/or in this disclosure—patent/invention are herein incorporated by reference to the same extent as if each publication or report, or patent or pending patent and/or references listed in these publications, reports, patents or pending patents were specifically and individually indicated to be incorporated by reference.

CROSS REFERENCE TO U.S. PATENTS

The following referenced documents contain subject matter related to that disclosed in the current disclosure:

1. U.S. Pat. No. 6,907,291 issued Jun. 14, 2005, Snell et al.: "Secure telemetry system and method for an implantable cardiac stimulation device", assigned to Pacesetter, Inc., Sylmar, Calif.
2. U.S. Pat. No. 6,906,996 issued Jun. 14, 2005, Ballantyne, G. J.: "Multiple modulation wireless transmitter"
3. U.S. Pat. No. 6,889,135 issued May 3, 2005, Curatolo, B. S. et al.: "Security and tracking system"
4. U.S. Pat. No. 6,879,842 issued Apr. 12, 2005, King, J. et al.: "Foldable Wireless Communication Device Functioning as a Cellular Telephone and Personal Digital Assistant"
5. U.S. Pat. No. 6,879,584 issued Apr. 12, 2005, Thro et al.: "Communication services through multiple service providers"
6. U.S. Pat. No. 6,876,859 issued Apr. 5, 2005 Anderson, R. J. et al.: "Method for Estimating TDOA and FDOA in a Wireless Location System"
7. U.S. Pat. No. 6,876,310 issued Apr. 5, 2005, Dunstan, R. A.: "Method and apparatus to locate a device in a dwelling or other enclosed space"
8. U.S. Pat. No. 6,865,395 issued Mar. 8, 2005, Riley, W.: "Area based position determination for terminals in a wireless network"
9. U.S. Pat. No. 6,842,617 issued Jan. 11, 2005, Williams B. G.: "Wireless Communication Device with Multiple External Communication Links"
10. U.S. Pat. No. 6,823,181 issued Nov. 23, 2004, Kohno et al.: "Universal platform for software defined radio"
11. U.S. Pat. No. 6,807,564 issued Apr. 12, 2005, Zellner et al.: "Panic button IP device"
12. U.S. Pat. No. 6,788,946 issued Sep. 7, 2004 Winchell, D. et al.: "Systems and Methods for Delivering Information within a Group of Communication System"
13. U.S. Pat. No. 6,741,187 issued May 25, 2004, Flick, K.: "Vehicle tracker providing vehicle alarm alert features and related methods"
14. U.S. Pat. No. 6,711,440 issued Mar. 23, 2004, Deal et al.: "MRI-compatible medical device with passive generation of optical sensing signals" issued to Biophan Technologies, Inc.
15. U.S. Pat. No. 6,424,867 issued Jul. 23, 2002, Snell et al.: "Secure telemetry system and method for an implantable cardiac stimulation device", assigned to Pacesetter, Inc., Sylmar, Calif.
16. U.S. Pat. No. 6,393,294 issued May 21, 2002 Perez-Breva et al.: "Location determination using RF fingerprinting"
17. U.S. Pat. No. 6,067,018 issued May 23, 2000 Skelton et al.: "Lost Pet Notification System"
18. U.S. Pat. No. 6,591,084 issued Jul. 8, 2003, Chuprun, et al.: "Satellite based data transfer and delivery system"
19. U.S. Pat. No. 6,772,063 Ihara et al.: "Navigation Device, Digital Map Display System, Digital Map Displaying Method in Navigation Device, and Program", Issued Aug. 3, 2004.
20. U.S. Pat. No. 6,775,254 Willenegger et al.: "Method and Apparatus for Multiplexing High Speed Packet Data Transmission with Voice/Data Transmission", Issued Aug. 10, 2004.
21. U.S. Pat. No. 6,748,021 Daly, N.: "Cellular radio communications system" Issued Jun. 8, 2004.
22. U.S. Pat. No. 6,775,371 Elsey et al.: "Technique for Effectively Providing Concierge-Like Services in a Directory Assistance System", issued Aug. 10, 2004.
23. U.S. Pat. No. 6,539,253 Thompson et al.: "Implantable medical device incorporating integrated circuit notch filters", issued Mar. 25, 2003
24. U.S. Pat. No. 6,418,324 Doviak, et al.: "Apparatus and method for transparent wireless communication between a remote device and host system", Jul. 9, 2002

25. U.S. Pat. No. 6,128,330 Schilling; D. L.: "Efficient shadow reduction antenna system for spread spectrum", issued Oct. 3, 2000.
26. U.S. Pat. No. 6,101,224, Lindoff et al.: "Method-apparatus for linearly modulated signal using polar modulation" issued on Aug. 8, 2000
27. U.S. Pat. No. 6,088,585 Schmitt, J. C., and Setlak; D. R.: "Portable telecommunication device including a fingerprint sensor and related methods", issued on Jul. 11, 2000.
28. U.S. Pat. No. 5,479,448, Seshadri, N.: "Method and Apparatus for Providing Antenna Diversity", issued on Dec. 26, 1995
29. U.S. Pat. No. 5,430,416, issued on Jul. 4, 1995 Black et al.: "Power amplifier having nested amplitude modulation controller and phase modulation controller"
30. U.S. Pat. No. 4,745,628, McDavid et al.: "Symbol Generator for Phase Modulated Systems" issued on May 17, 1988
31. U.S. Pat. No. 3,944,926, Feher, K.: "Timing Technique for NRZ Data Signals", issued Mar. 16, 1976.
32. U.S. Pat. No. 4,339,724, Feher, K.: "Filter" issued Jul. 13, 1982.
33. U.S. Pat. No. 4,720,839, Feher et al.: "Efficiency Data Transmission Techniques", issued Jan. 19, 1988.
34. U.S. Pat. No. 4,350,879 Feher, K.: "Time Jitter Determining Apparatus", issued Sep. 21, 1982.
35. U.S. Pat. No. 4,567,602 S. Kato, K. Feher: "Correlated Signal Processor", issued Jan. 28, 1986.
36. U.S. Pat. No. 4,644,565 issued Feb. 17, 1987. J. Seo, K. Feher: "Superposed Quadrature Modulated Baseband Signal Processor"
37. U.S. Pat. No. 5,491,457 Issued Feb. 13, 1996: K. Feher: "F-Modulation Amplification"
38. U.S. Pat. No. 5,784,402 Issued Jul. 21, 1998: K. Feher: "FMOD Transceivers Including Continuous and Burst Operated TDMA, FDMA, Spread Spectrum CDMA, WCDMA and CSMA,"
39. U.S. Pat. No. 6,445,749, Issued Sep. 3, 2002 K. Feher: "FMOD Transceivers Including Continuous and Burst Operated TDMA, FDMA, Spread Spectrum CDMA, WCDMA and CSMA,"
40. U.S. Pat. No. 6,198,777 issued Mar. 6, 2001. K. Feher: "Feher Keying (FK) Modulation and Transceivers Including Clock Shaping Processors"
41. U.S. Pat. No. 6,470,055 issued Sep. 3, 2002. K. Feher: "Spectrally efficient FQPSK, FGMSK, and FQAM for enhanced performance CDMA, TDMA, GSM, OFDN, and other systems".
42. U.S. Pat. No. 6,665,348, K. Feher: "System and Method for Interoperable Multiple-Standard Modulation and Code Selectable Feher's GMSK, Enhanced GSM, CSMA, TDMA, OFDM, and other Third-Generation CDMA, WCDMA and B-CDMA" issued Dec. 16, 2003.
43. U.S. Pat. No. 6,757,334 K. Feher: "Bit Rate Agile Third-Generation wireless CDMA, GSM, TDMA and OFDM System", issued Jun. 29, 2004.

CROSS REFERENCES TO RELATED U.S. PATENT APPLICATIONS

44. U.S. patent application Ser. No. 10/205,478 K. Feher: "Modulation and Demodulation Format Selectable System", filed Jul. 24, 2002. Continuation of U.S. patent application Ser. No. 09/370,360 filed Aug. 9, 1999; and now U.S. Pat. No. 6,470,055;
45. U.S. patent application Ser. No. 10/831,562 K. Feher: "Adaptive Receivers for Bit Rate Agile (BRA) and Modulation Demodulation (Modem) Format Selectable (MFS) Signals", Continuation of application Ser. No. 09/370,362 filed Aug. 9, 1999 and now U.S. Pat. No. 6,757,334.
46. U.S. patent application Ser. No. 10/831,724, filed on Apr. 24, 2004 K. Feher: "CDMA, W-CDMA, $3^{rd}$ Generation Interoperable Modem Format Selectable (MFS) systems with GMSK modulated systems", [Continuation of Ser. No. 09/370,362 filed Aug. 9, 1999 and now U.S. Pat. No. 6,757,334].
47. U.S. patent application Ser. No. 09/732,953 Pub. No.: 2001/0016013 Published Aug. 23, 2001 K. Feher: "Ultra Efficient Modulation and Transceivers"
48. U.S. patent application Ser. No. 11/023,279 filed: Dec. 28, 2004 Feher, K. "BROADBAND, ULTRA WIDEBAND AND ULTRA NARROWBAND RECONFIGURABLE INTEROPERABLE SYSTEMS", claiming benefits of Provisional Application "Ultra Wideband, Ultra Narrowband and Reconfigurable Interoperable Systems" 60/615,678 filed Oct. 5, 2004
49. U.S. patent application Ser. No. 11/023,254 filed: filed: Dec. 28, 2004; Feher, K. "DATA COMMUNICATION FOR WIRED AND WIRELESS COMMUNICATION,"
50. U.S. patent application Ser. No. 11/102,896, Applicant Feher, K., entitled: "HYBRID COMMUNICATION AND BROADCAST SYSTEMS" claiming benefits of Provisional Application "Ultra Wideband Ultra Narrowband and Reconfigurable Interoperable Systems" 60/615,678 filed Oct. 5, 2004. submitted to the USPTO on Dec. 22, 2004 and filed by USPTO on Mar. 28, 2005.
51. U.S. patent application Ser. No. 11/105,295, Applicant Feher, K., entitled: "OFDM, CDMA, SPREAD SPECTRUM, TDMA, CROSS-CORRELATED AND FILTERED MODULATION" a continuation Application of U.S. patent application Ser. No. 10/205,478 and of U.S. patent application Ser. No. 09/370,360 now U.S. Pat. No. 6,470,055. This application was Submitted to the USPTO on Apr. 11, 2005.
52. U.S. patent application Ser. No. 11/023,279, Applicant Feher, K., entitled: "BROADBAND, ULTRA WIDEBAND AND ULTRA NARROWBAND RECONFIGURABLE INTEROPERABLE SYSTEMS", filed Dec. 28, 2004, United States Patent and Trademark Office (USPTO)
53. U.S. patent application Ser. No. 11/102,896 Applicant Feher, K., entitled: "HYBRID COMMUNICATION AND BROADCAST SYSTEMS". submitted to the United States Patent and Trademark Office (USPTO) on Dec. 22, 2004; filed by USPTO on Mar. 28, 2005
54. U.S. patent application Ser. No. 11/023,254, Applicant Feher, K., entitled: and entitled "DATA COMMUNICATION FOR WIRED AND WIRELESS COMMUNICATION", submitted to the United States Patent and Trademark Office (USPTO) on Dec. 22, 2004
55. U.S. patent reexamination application Ser. No. 90/007,305 of U.S. Pat. No. 6,665,348 issued Dec. 16, 2003: "System and Method for Interoperable Multiple-Standard Modulation and Code Selectable Feher's GMSK, Enhanced GSM, CSMA, TDMA, OFDM, and other Third-Generation CDMA, WCDMA and B-CDMA". Parent patent application Ser. No. 09/370,361. Reexamination application filed on Nov. 19, 2004

CROSS REFERENCES TO RELATED CO-PENDING U.S. PATENT APPLICATIONS

The following three (3) related U.S. patent applications, submitted by Applicant/Inventor Kamilo Feher, are co-pending:

56. U.S. utility patent application Ser. No. 11/197,610, Ref No. (56), entitled "Location finder, tracker, communication and remote control system", submitted to the United States Patent and Trademark Office (USPTO) on Aug. 3, 2005.

57. U.S. utility patent application Ser. No. 11/197,670, Ref No. (57), entitled "Medical diagnostic and communication system", submitted to the United States Patent and Trademark Office (USPTO) on Aug. 3, 2005.
58. U.S. utility patent application Ser. No. 11/197,609, Ref No. (58), entitled "Multimode communication system", submitted to the United States Patent and Trademark Office (USPTO) on Aug. 3, 2005.

CROSS REFERENCE TO PUBLICATIONS 59. 3GPP TS 25.213 V6.0.0 (2003-12) $3^{rd}$ Generation Partnership Project; Technical Specification Group Radio Access Network Spreading and Modulation (FDD) (Release 6) 28 pages
60. 3GPP TS 05.04 V8.4.0 (2001-11) Technical Specification Group GSM/EDGE Radio Access Network; Digital cellular telecommunications system (Phase 2+); Modulation (Release 1999); 3GPP:$3^{rd}$ Generation Partnership Project; (10 pages)
61. Brown, C., Feher, K: "A reconfigurable modem for increased network capacity and video, voice, and data transmission over GSM PCS", IEEE Transactions on Circuits and Systems for Video Technology, pp: 215-224; Volume: 6, No. 2, April 1996 (10 pages)
62. Brown, C. W.: "New Modulation and Digital Synchronization Techniques for Higher Capacity Mobile and Personal Communications Systems" Ph.D. Thesis University of California, Davis, Nov. 1, 1996 pp: i-vii; 138-190; 269-272; 288-289; 291.
63. Brown, C., Feher, K.: "A Flexible Modem Structure for Increased Network Capacity and Multimedia Transmission in GSM PCS", Proceedings of the Fifteenths Annual Joint Conference of the IEEE Computer and Communication Societies (INFOCOM '96), 1996 (8 pages)
64. Furuscar, A. et al.: "EDGE: Enhanced Data Rates for GSM and TDMA/136 Evolution" IEEE Personal Communications, June, 1999, pp: 56-66.
65. Qualcomm: "MSM 6275 Chipset Solution", Qualcomm CDMA Technologies, San Diego, Calif., 2004 (8 pages)
66. Qualcomm: "MSM 6300 Chipset Solution", Qualcomm CDMA Technologies, San Diego, Calif., 2004 (8 pages)
67. Baisa, N. "Designing wireless interfaces for patient monitoring equipment", RF Design Magazine April 2005, www.rfdesign.com (5 pages)
68. Hickling, R. M.: "New technology facilitates true software-defined radio" RF Design Magazine April 2005, www.rfdesign.com (5 pages)
69. Feher, K.: "Wireless Digital Communications: Modulation & Spread Spectrum Applications", Prentice Hall PTR, Upper Saddle River, N.J. 07458, Copyright 1995, Book ISBN No: 0-13-098617-8 (pages: front page; copyright page; pp. 164-177; 461-471; and 475-483)
70. Holma, H., Toskala, A.: "WCDMA for UMTS Radio Access for Third Generation Mobile Communications", Second Edition, John Wiley & Sons Ltd. Chichester, West Sussex, England, Copyright 2002, ISBN 0-470-84467-1 (pages: front page; copyright page; pp. xv-xvi; 1-4; 90-95; 199-201; and 235-236)
71. Tuttlebee, W.: "Software Defined Radio: Baseband Technology for 3G Handsets and Basestations", John Wiley & Sons, Ltd., Chichester, West Sussex, England, Copyright 2004, ISBN 0-470-86770-1. (pages: front page; copyright page; pp. 1-3; 8-15; 34-39; and 274-279)
72. Dobkin, D. M. and Wandinger, T.: "A Radio Oriented Introduction to Radio Frequency Identification" RFID Tutorial, High Frequency Electronics, June 2005, Copyright 2005 Summit Technical Media (6 pages)
73. Dale Setlak: "Fingerprint sensors in Wireless handsets" a presentation at the EOEM Design Expo Jun. 22, 2005, Wireless OEM Design Expo Online Conference & Exhibition, http://www.reedbusinessinteractive.com/eoem/index.asp (38 pages)

Acronyms

To facilitate comprehension of the current disclosure frequently used acronyms and or abbreviations used in the prior art and/or in the current disclosure are highlighted in the following LIST of acronyms:

2G Second generation or $2^{nd}$ generation wireless or cellular system
3D three dimensional
3G Third Generation or $3^{rd}$ generation wireless or cellular system
4G Fourth Generation wireless or cellular system
5G Fifth Generation or future generation
AM Amplitude Modulation
AMC Adaptive Modulation and Coding
ACM Adaptive Coding and Modulation
Bluetooth Wireless system standardized by the Bluetooth organization
BPSK Binary Phase Shift Keying
BRA Bit Rate Agile or Bit Rate Adaptive
BST Base Station Transceiver
BWA Broadband Wireless Access
CC cross-correlation or cross-correlate
CCOR cross-correlation or cross-correlate
CDMA Code Division Multiple Access
CM Clock Modulated
CS Code Selectable
CSMA Collision Sense Multiple Access
CL Clock Shaped
DECT Digital European Cordless Telecommunication
DNA Deoxyribose Nucleic Acid
DS-SS Direct Sequence Spread Spectrum
EDGE Enhanced Digital GSM Evolution; Evolution of GSM or E-GSM
EMI Electromagnetic Interference
FA Frequency Agile (selectable or switched IF or RF frequency)
FDM Frequency Division Multiplex
FH-SS Frequency Hopped Spread Spectrum
FQPSK Feher's QPSK or Feher's patented QPSK
FOC Fiber Optic Communication
FSK Frequency Shift Keying
GFSK Gaussian Frequency Shift Keying
GPS Global Positioning System
GPRS General Packet Radio Service
GMSK Gaussian Minimum Shift Keying
GSM Global Mobile System or Global System Mobile
HDR Hybrid Defined Radio
IEEE 802 Institute of Electrical and Electronics Engineers Standard Number 802
IR Infrared
LAN Local Are Network
LINA Linearly amplified or Linear amplifier or linearized amplifier
LR Long Response
MES Modulation Embodiment Selectable
MFS Modulation Format Selectable
MIMO Multiple Input Multiple Output
MISO Multiple Input Single Output
MMIMO Multimode Multiple Input Multiple Output
MSDR Multiple Software Defined Radio NLA Non-Linearly Amplified or Non-Linear Amplifier
NQM non-quadrature modulation
NonQUAD non-quadrature modulator
NRZ Non Return to Zero
OFDM Orthogonal Frequency Division Multiplex
OFDMA Orthogonal Frequency Division Multiple Access
PDA Personal Digital Assistants
PDD Position Determining Device
PDE Position Determining Entity
PTT push to talk
QUAD Quadrature; also used for quadrature modulation
quad Quadrature; also used for quadrature modulation
QM Quadrature Modulation
QPSK Quadrature Phase Shift Keying
RC Remote Control
RFID Radio Frequency Identification
Rx receive
SDR Software Defined Radio (SDR)
SIMO Single Input Multiple Output
STCS Shaped Time Constrained Signal
MSDR Multiple Software Defined Radio
TBD to be decided
TCS Time Constrained Signal
TDM Time Division Multiplex
TDMA Time Division Multiple Access
TR transceiver (transmitter-receiver)
Tx transmit
TV television
UMTS Universal Mobile Telecommunication System
UNB Ultra narrowband or Ultra narrow band
URC Universal Remote Control
UWB Ultrawideband or ultra wideband
UWN Ultrawideband-Ultra Narrow Band
ViIP Video over Internet Protocol
VoIP Voice over Internet Protocol
W waveform, wavelet or wave (signal element)
WAN Wide Area Network
WCDMA Wideband Code Division Multiple Access
W-CDMA Wideband Code Division Multiple Access
Wi Fi Wireless Fidelity or related term used for systems such as IEEE 802.x_standardized systems; See also Wi-Fi
Wi-Fi wireless fidelity
WLAN Wireless Local Area Network
www World Wide Web (or WWW or) WEB
XCor cross-correlation or cross-correlator or cross-correlate

FIELD OF THE INVENTION

The field of the invention includes wired and wireless communication, broadcasting, entertainment, remote control, medical diagnostics, emergency and alarm, interactive touch screen, fingerprint controlled communication and control systems for single or multimode communications, broadcasting, teleinformatics and telemetry systems.

The disclosed subject matter is for multiuse and or multipurpose applications, devices and systems, including systems for: position determination, location finding based services and applications, remote control, wireless, wired, cabled, internet, web based communication systems, communicator devices, radio frequency identification (RFID) systems with single or plurality of devices, emergency and other alarm systems, medical patient monitor-sensor devices, medical diagnostics devices, fingerprint identification, fingerprint control, interactive communication or control of communications and control systems, communications, broadcasting, teleinformatics and telemetry systems.

BACKGROUND

Prior art references disclose position location, tracking and communication devices. Exemplary prior art includes: U.S. Pat. No. 6,865,395, U.S. Pat. No. 6,889,135, U.S. Pat. No. 6,879,584, U.S. Pat. No. 6,876,859, U.S. Pat. No. 6,876,310 and U.S. Pat. No. 6,842,617. From the prior art it is known that it is often desired, and sometimes necessary, to know the position, that is, the location of a wireless user. For example, the ITS Federal Communications Commission (FCC) has ordered an enhanced emergency 911 (emergency 911 or enhanced emergency E-911) wireless service that requires the location of a wireless terminal (e.g., a cellular phone) to be provided to a Public Safety Answering Point (PSAP) each time a 911 call is made from the terminal. The recognized need for improved personal security and emergency response capability has been documented in the prior art. In situations where an individual is injured, lost or abducted, immediate notification of an emergency situation including location of the emergency to a local law enforcement or emergency response organization is required to maintain the safety of the individual and to mitigate or avoid severe and or tragic situations.

In addition to emergency situations, there is also a recognized need for improved personal healthcare and in particular patient monitor and other diagnostic systems. Patients are often confined in a fixed area to cabled (or tethered) monitoring equipment. An illustrative, cited prior art reference, published by Baisa, N.: "Designing wireless interfaces for patient monitoring equipment". RF Design Magazine April 2005, highlights that recent advances in wireless technologies now make it possible to free patients from their equipment, allowing greater freedom and even making possible monitoring by their health provider while the patient is on the go. The position of a wireless terminal may be estimated using various techniques including "range-domain" and "position-domain" techniques as well as other techniques and/or combined hybrid techniques.

Acronyms and abbreviations: several terms, acronyms and abbreviations, used in literature, including patents, journal papers, conference publications, books, published standards and reports have the same and/or similar meaning as in the present application. In particular, terms acronyms and abbreviations, used in the prior art Feher et al. patents: U.S. Pat. No. 6,470,055 (the '055 patent) U.S. Pat. No. 6,665,348, U.S. Pat. No. 6,757,334, U.S. Pat. No. 4,567,602 and U.S. Pat. No. 5,491,457 are often used in this document. To facilitate comprehension of some of the terms used in the prior art literature, parts of the prior art '055 patent are reviewed in this application. For other prior art terms, acronyms and abbreviations described in the cited references, the references contained in the cited references and other prior art material are applicable.

Position determining devices (PDD), also designated as position determining entities (PDE) and position determining transmitters mean devices and transmitters which generate and transmit signals used by receivers and receive processors for location or position determination and/or location or position estimation have been also described in the prior art.

Exemplary prior art single-chamber pacemaker and/or dual-chamber pacemaker and implantable cardiac stimulation devices are described in exemplary cited U.S. Pat. No. 6,539,253 and in U.S. Pat. No. 6,907,291.

SUMMARY AND NEED FOR THIS INVENTION

Multiuse wireless communication applications, having extended coverage, improved performance, seamless interoperability, high speed operation, enhanced capacity, multipurpose, multi functionality, multi-mode and multi-standard interoperability are highly desired. The current application discloses multiuse and or multipurpose applications, devices and systems, including systems for: position determination, location finding based services and applications, remote control, wireless, wired, cabled, internet, web based communication systems, communicator devices, radio frequency identification (RFID) systems with single or plurality of devices, emergency and other alarm systems, medical patient monitor-sensor devices, medical diagnostics devices, fingerprint identification, fingerprint control, interactive communication or control of communications and control systems, communications, broadcasting, teleinformatics and telemetry systems.

Most multi-media and video services require bandwidths and or other multiuse capabilities that transcend the capabilities of currently operational second generation 2G and or third generation 3G cellular service providers. Hence, many wide bandwidth applications and services that are rapidly evolving, for example, on the Internet, have not to date readily and widely accessible cellular and cellular interconnections to mobile wireless users via wireless local area networks (WLAN) and/or other wideband networks. New systems and end user devices or units are being contemplated that provide for or include, respectively, high bandwidth short range networking capabilities, using WLAN technologies such as IEEE 802.x_ or Bluetooth. These links may allow mobile handsets to establish Internet attachments when they approach a network access point (NAP). These WLAN based systems may create an opportunity for these untethered devices to enjoy high bandwidth services, once reserved for fixed devices. However, the WLAN systems only provide short range coverage, are not widely deployed, or do not provide for user mobility and hence are not generally suitable of providing enhanced services for mobile users over a wide area. It is desirable to develop multiuse, multi-mode, multi standard interoperable technologies which integrate the capabilities of cellular, infrared (IR), satellite, wide area network (WAN) and WLAN systems to provide complete end-to-end enhanced services. This can be achieved by modulation format selectable (MFS) and bit rate agile (BRA) multi-mode, multiuse interoperable systems. Wireless Fidelity (Wi-Fi) systems and Wi-Fi embodiments are included and integrated with other implementation architectures in the current disclosure. The terms Wi-Fi or wireless fidelity or related terms, used in this application, are for systems such as IEEE 802.x_ standardized systems and are to be used generically when referring of any type of 802.11 network, whether IEEE 802.11b, 802.11a, 802.16, 802.20 dual-band, etc. The term Wi-Fi is also used as promulgated by the Wi-Fi Alliance and has also broader interpretations; alternative terms to Wi-Fi, such as UWB/W-USB, ZigBee, NFC and WiMax are also used and included in the embodiments of this invention. Nowadays it is not unusual that an individual has a cellular phone, a pager, about three or more remote control (RC) devices e.g. one or more RC for one or more television sets, for VCR for satellite channel TV set, garage opener, car opener, portable FM radio, video camcorder, computer, PDA, multiple cordless phones and other electronic devices. It is overwhelming just to keep track of all of these devices. Thus, consolidation or integration of many devices, units into one multipurpose or multiuse unit would be desirable. To enable the implementation of efficient multiuse communication devices for single or multiple information signals and communications between and within multiple standardized and a multitude of non-standardized systems, between a large class of communication and control transmission-reception media, such as wireless (e.g. cellular, land mobile, satellite), cable, Fiber Optics Communication (FOC), internet, intranet and other media there is a need to have adaptable or agile systems and adaptable embodiment structures. Such structures including Intermediate Frequency (IF) and or Radio Frequency (RF) agile, Bit Rate Agile or Bit Rate Adaptable (BRA), Modulation Format Selectable (MFS) and or Modulation Embodiment Selectable (MES) systems are disclosed. The multiuse modulator-demodulator (modem) and or modulator and or demodulator implementations, disclosed in this application, have Intermediate Frequency (IF) and or Radio Frequency (RF) agile, that is IF adaptable and or RF adaptable embodiments. In IF and or RF adaptable or IF and or RF agile systems the center frequency of the modulated signal(s) is selectable and or adaptable to the desired transmission frequency band. The RF transmitter-receiver (transceiver) embodiments are also RF agile implementations. Several features of the multiuse embodiments are optional and are not included in some implementation structures. Some of these include the optional Bit Rate Agile or Bit Rate Adaptable (BRA) structures and or RF agile implementations and or cross-correlated and or other structures and or features. There is a need for one or more of the modulators, in certain embodiments to have BRA and or Code Selectable and or MFS and or MES implementations. The term Modulation Format Selectable (MFS), as used in this application is defined to mean that the modulation technique (modulation format) is adaptable, changeable (selectable) and also that the coding technique, if coding is used in the system is also adaptable, changeable (selectable) in certain embodiments. In some disclosed embodiments the same modulation format and same bit rate is used, however the modulation embodiment is different. For example, in an application a GMSK modulated system uses a Quadrature Modulation (QM) structure for low transmit power applications, while for a high transmit power application it uses a non-quadrature modulation (NQM), e.g. polar implementation structure. Thus, in this example the same GMSK modulation format, having the same bit rate (or a different bit rate) is switched (or selected) to be transmitted instead in the QM embodiment in a NQM embodiment The disclosed subject matter is for multiuse and or multipurpose applications, devices and systems, including systems for: position determination, location based services and applications, location finding, tracking, single or multiple tracking, Remote Control (RC), Universal Remote Control (URC), wireless, wired, cabled, internet web based communication systems, communicator devices, radio frequency identification (RFID) systems with single or plurality of devices, emergency and other alarm systems, medical patient monitor-sensor devices, diagnostics units and systems, Deoxyribose Nucleic Acid (DNA) systems, fingerprint identification, fingerprint control and or using DNA samples for interactive communication or control of certain communications and control systems, cardiac stimulation devices, systems having push to talk (PTT) options, interactive touch screen controlled communication and control systems for single or multimode communications broadcasting, teleinformatics and telemetry systems.

The presented implementations and embodiments are for single and multiple devices in single and multiple mode systems and networks. Location finding, tracking and identification of devices, including processing of certain measured parameters or diagnostics results (via sensors, such as motion detectors, body temperature, blood pressure or other devices) are communicated to devices and units which might be at central locations and or are peers of the monitored located device and are also mobile units, e.g. mobile telephones, mobile computers such as Personal Digital Assistants (PDA) or laptop computers, mobile entertainment or educational devices, or mobile navigational and interactive devices, or are units at fixed locations, e.g. wired telephones or computers. Interactive location based and educational and or entertainment devices and systems for mobile wireless and or wired media or internet web media information transfer and telematics and telemetry are also included. Regarding images, pictures and video and scanned or stored images and pictures three dimensional (3D) images are included in the communications units. Certain devices have incorporated touch screens for control or communication or interaction with the communication and or display devices.

Multimode, multiuse system operation, multi-purpose diagnostics, patient monitoring, multi purpose systems, including connections of multi mode devices to allow users communication and control with interoperable connected cellular Global Mobile System (GSM), Wireless-Fidelity (Wi-Fi) systems devices or phones to roam from wide area to local area wireless networks and vice versa, with location finder seamless operation and wired or internet web based monitoring signal processing implementations are presented. These systems, in certain applications are connected to cordless telephones and or other cordless devices. The term signal processing refers to signal and or data processing. This application includes multi operation and multi function of a plurality of embodiments of one or more of the following system components: single or multiple location finder, location tracker devices, position finder devices (note the terms "location finder", "location tracker" and "position finder" have in several parts of this disclosure practically the same meaning), Radio Frequency Identification Devices (RFID), connected with single or multiple Bit Rate Agile (BRA), and single modulation or Modulation Format Selectable (MFS) satellite and/or land based devices. These multiuse system components assembled in one or more combinations and variations, also known as "plug and play", are disclosed for operation in standardized systems, e.g. GSM, General Packet Radio Service (GPRS), Enhanced Digital GSM Evolution (EDGE), or Evolution of GSM (E-GSM), Code Division Multiple Access (CDMA), Wideband Code Division Multiple Access (WCDMA or W-CDMA), Orthogonal Frequency Division Multiplex (OFDM) Time Division Multiple Access (TDMA), IEEE 802.xx, Digital European Cordless Telecommunication (DECT), Infrared (IR), Wireless Fidelity (Wi-Fi), Bluetooth, and other standardized as well as non-standardized systems. While, prior art wireless short range systems such as the standardized Bluetooth system provide connection to cell phone systems the prior art short range systems do not provide connection to selectable enhanced performance multi-standard, multi-mode, Modulation Format Selectable (MFS) and Bit Rate Selectable systems (also designated as Bit Rate Agile (BRA) systems) and cascaded wireless, wired and Internet Protocol (IP) and embodiments, such as described and claimed in the invention. This application includes embodiments and architectures for more efficient implementation and of enhanced performance second generation (2G), third generation (3G), fourth generation (4G) and fifth generation (5G) and other new generations of wireless and broadcast, processing, storage, medical diagnostics-communications and control, interactive entertainment and educational and business systems with or without use of internet and/or multimedia systems. The terms 2G, 3G, 4G, and 5G have a broad generic meaning and are not limited to certain specific standards. These terms are interpreted, within the new inventions disclosed herein, as new generation and or enhanced performance or more efficient implementation of prior art system.

In addition to finding lost, runaway or kidnapped humans, lost, runaway or stolen pets/animals or objects, several medical applications for patient monitoring with multi-mode wireless, wired and internet systems are also disclosed in this application. For surgery, other medical procedures and medical patient monitoring and diagnostics, hybrid wired and wireless or purely wireless systems which reduce or eliminate the cables and wires attached to human body are also described. Video broadcasting, multicasting and video conferencing technologies, in conjunction with the aforementioned technologies are also disclosed. Language translators with written and audio converted text are presented. Voice recognition systems and fingerprint recognition transmission and activation methods are disclosed.

To remove or minimize cables for patient monitoring systems new architectures, structures and embodiments for multi mode, multi standard, non standardized wireless, wired, cabled, infrared, multiple "cascaded" switched and combined solutions and systems are presented in this disclosure. This include cascade of cellular i.e. GSM or GSM switched to CDMA systems, with short range wireless systems—one or multiple such as Wi-Fi, Bluetooth or other. Motivation for reducing the number of cables include, the desire to eliminate the cumbersome cables connected to the patient, facilitate the surgery, and facilitate and speed up the patient recovery-enabling the patient to move, exercise and improve the quality of life of the patient during surgery, recovery and post recovery monitoring and shorten emergency time response including a remote physician, nurse or other authorized health provider—in a reverse link to control-administer certain medical—pharmaceutical items, e.g. insulin or other; also to eliminate or reduce cable caused potentially harmful currents to the patient. The term reverse link means the link (signal flow) from the physician, nurse or other authorized health provider to the patient or patients medical device; the term forward link refers to the link from the patients medical device, e.g. from the cardiac stimulation device to the physician, nurse or other authorized health provider or health monitoring system.

The prior art pacemaker control requires magnet detection circuit for magnet controlled pacemaker parameters. Unfortunately this magnet dependent operation/change of parameters of pacemakers is in many cases causing difficulties and or even rendering impossible to have Magnetic Resonance Imaging (MRI), and/or Magnetic Resonance Image scanning on a patient who has a pace maker. Since MRI is a frequently desired diagnostic procedure for diagnostic purposes, even in an emergency where the information from the MRI scan could be life saving, and since MRI interferes with the correct operation of currently available magnetic detection-magnetic controlled based pacemakers, it would be highly desirable to develop a new generation of pacemakers which could be operated and controlled without substantial magnetic materials, i.e. without the need of magnet based detection and magnet control.

In distinction with the prior art magnet detection circuit, in the current invention there is no need for magnet detection circuits and no need for magnet's to be placed over or into the pacemaker to reset or modify parameters and functions/operation of the pacemaker. In the current invention magnetic detection and magnet control of pacemaker is replaced by wireless signal detection and based on the detected wireless signals and processing of said wireless detected signals (received from a physician operated wireless transmitter) control signals are generated to control the parameters and operation of the pacemaker.

Wireless systems authentication with fingerprint and or other means is also disclosed.

In this application the terms "multiuse" and or "multipurpose" mean that one or more of the aforementioned applications, systems, system architectures and or embodiments or combinations of the aforementioned system components are used.

BRIEF DESCRIPTION OF THE FIGURES

FIG. 11a is a new implementation architecture and block diagram of a multiple communication link, also designated as a cascaded link, or a system having cascaded units which inter operate in a sequence for multimode operated wireless and or wired and internet systems including fixed location systems and mobile systems.

FIG. 11b shows an exemplary prior art quadrature modulator.

FIG. 17a is a Non-quadrature (non-QUAD) and quadrature modulation (Quad Mod or QUAD mod) multiple modulator embodiment, including polar modulator structures.

FIG. 17b shows a polar (non Quadrature) exemplary prior art modulator implementation block diagram.

FIG. 17c a Non-Quadrature (non-QUAD) exemplary prior art modulator architecture is illustrated.

DETAILED DESCRIPTION OF THE INVENTION AND OF THE PREFERRED EMBODIMENTS

In this section, the present invention is more fully described with reference to the accompanying drawings in which preferred embodiments of the invention are shown. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art.

One or more devices (alternatively designated as units, elements, systems, terminals, devices, leads or connections) are optional in the embodiments. The elements may be interconnected and or used in various configurations. In the figures and relevant descriptions of the figures, as well as in the specifications of this disclosure, some of the units or elements are optional and are not required for certain applications, embodiments and or structures. In this document the term "signal" has the most generic meaning used in the prior art and includes electrical, acoustical, infrared, X-ray, fiber optics, light sound, position, altitude diagnostics, beat, density, and other sensor or device or human being or animal or object generated or processed waveforms, images, pictures, symbols, wavelets, wave shapes and analog or digital or "hybrid" analog and digital signals.

Figure 1:
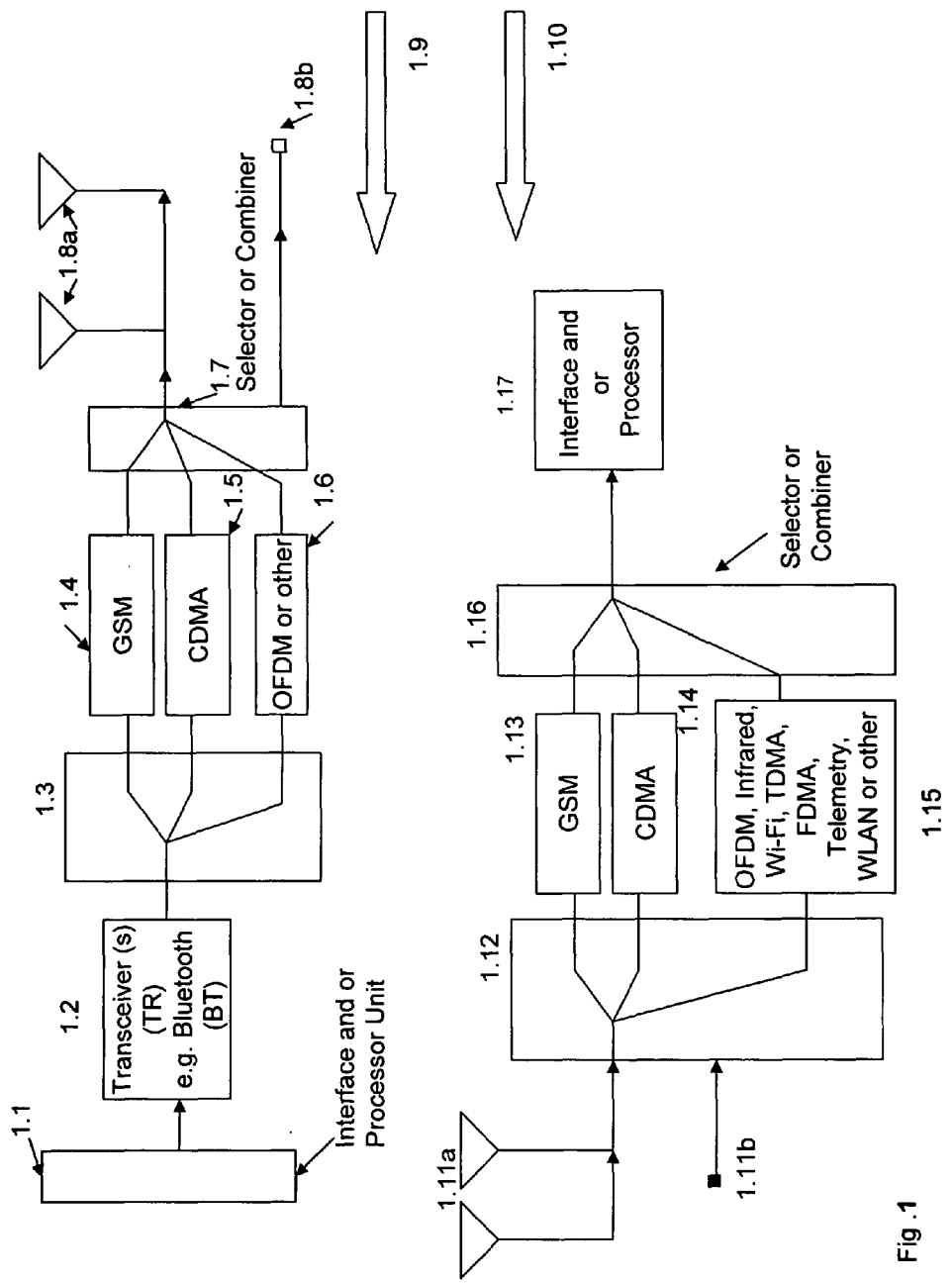
FIG. 1 shows implementation structures for single and or multiple communications systems, including single and or multiple location or position finder systems, Radio Frequency Identification Devices (RFID), medical diagnostics, emergency and remote control systems.

FIG. 1 shows implementation structures for single and or multiple communications systems, including single and or multiple location or position finder systems, Radio Frequency Identification Devices (RFID), medical diagnostics, emergency communication and remote control systems connected with single or multiple Bit Rate Agile (BRA), and single modulation or Modulation Format Selectable (MFS) cellular, other mobile wireless, satellite and/or land based devices for Global Mobile System (GSM), General Packet Radio Service (GPRS), Enhanced Digital GSM Evolution (EDGE), or Evolution of GSM (E-GSM), Code Division Multiple Access (CDMA), Wideband Code Division Multiple Access (WCDMA or W-CDMA), Orthogonal Frequency Division Multiplex (OFDM), Time Division Multiple Access (TDMA), IEEE 802.xx, Digital European Cordless Telecommunication (DECT), Infrared (IR), Wireless Fidelity (Wi-Fi), Bluetooth, and other standardized as well as non-standardized systems. In particular, FIG. 1 is an embodiment of interface units, processors, transmitters and receivers (also designated as transceivers or TR), single or multiple communication and or broadcast devices, location finder, location, position finder and tracking devices and processors, connected through selectors or combiners with single or multiple transceivers, communication systems entertainment devices, educational systems and or medical devices, e.g. patient monitor devices and or sensors connected to one or more communication systems. Interface Unit 1.1 is a device or part of a communication system and or part of location finder or location tracking or location positioning system or processor, for example part of a Global Positioning System (GPS) receiver or an interface to a GPS receiver or other location finder or tracking device or a sensor, signal detector and processor of acoustic (e.g. voice, sound, music) signals, video and/or visual and/or image signals (moving video, still photographs, X-Ray pictures, telemetry signals), temperature (e.g. human body temperature, animal's body temperature, temperature of an object), electrical signal, Radio Frequency Identification Devices (RFID) received or generated signal, infrared, X-ray and or of other signals, parameters generated by sensors or obtained from any other sources. Unit 1.1 may contain sensors for heart beat, strength, pulse rate, glucose, arterial blood gas sensors, insulin sensors or monitors and or other medical devices. Unit 1.1 may also contain sensors and medical apparatus or devices connected to a patient during a surgery, or post surgery for patient monitoring. Unit 1.1 may contain only one of the mentioned elements, or more of the aforementioned elements. Unit 1.1 may contain certain combinations and/or variations of the devices described in this section. In some other embodiments Unit 1.1 is a simple interface unit to connect signals from a signal source and or from multiple sources to and or from the communication medium. The term "signal source" or "source" includes a broad class of signal sources, signal processors and or signal generators, including speech, audio, video, picture, display, data storage, information processors and other devices which generate, contain or process signals. Implementation of interface Unit 1.1 consists of a connection device (such as a wire or cable or part of circuit or connection to an antenna or an electronic or acoustical or infrared or laser coupler or connector, or an electronic or electrical circuit) or a combination of one or more devices. Interface Unit 1.1 may be a simple interface for video or television (TV), or digital camera (digital photo camera or digicam) signals or interface unit for a sequence of images or other visual signals such as photographs, scanned images or processors or devices of visual signals and or stored and programmable music-such as contained in prior art portable music players or integrated prior art MP3 players, with or without prior art Windows Mobile smart-phone software, computer, entertainment, games, interactive video games with or without location finders, location finders with or without radio FM/AM or digital radio or other radio or television broadcast signals. In one of the implementations Unit 1.1 contains the web or WEB or the World Wide Web, shortly web or www, Mobile Web access from mobile devices. Unit 1.1 contains in some of the embodiments a push to talk (PTT) processor. The signal or plurality of different type of signals is connected to one or more transceivers (TR) contained in Unit 1.2. The term transceiver refers to one or multiple transmitters and receivers and also to one or multiple receivers and transmitters. Specifically, the TR, Unit 1.2 may include one or multiple entire transceivers or could consist of one or multiple receivers or one or multiple transmitters. Unit 1.2 (also designated as Element 1.2 or Device 1.2) could be one or multiple Bluetooth (BT), infrared (IR), other wireless, e.g. satellite or cable, or wired transceiver(s), or part of a transceivers). Unit 1.3 is a signal splitter or signal selector device or connection which selects or combines and connects the Element 1.2 provided signals (one or more signals) to one or more communication systems or subsystems contained in communicator devices Unit 1.4, Unit 1.5, and Unit 1.6. The communicator devices Unit 1.4, Unit 1.5, and Unit 1.6 are parts or entire GSM, CDMA or Wireless Local Area Network (WLAN) or other wired, cabled or wireless devices respectively. Systems components in Unit 1.6, designated as "OFDM or other", are assembled in one or more combinations and variations, also known as "plug and play" and are for operation in single or multiple standardized systems, e.g. GSM, General Packet Radio Service (GPRS), Enhanced Digital GSM Evolution (EDGE), or Evolution of GSM (E-GSM), Code Division Multiple Access (CDMA), Wideband Code Division Multiple Access (WCDMA or W-CDMA), Orthogonal Frequency Division Multiplex (OFDM), Time Division Multiple Access (TDMA), IEEE 802.xx, Digital European Cordless Telecommunication (DECT), Infrared (IR), Wireless Fidelity (Wi-Fi), Bluetooth, and other standardized as well as non-standardized systems. One or more of the FIG. 1 components could be Modulation Format Selectable (MFS) and or Bit Rate Agile (BRA) systems. Signal selector or signal combiner Unit 1.7 provides the selected or combined signals to one or plurality antennas, shown as Unit 1.5a or other signal interface units which provide the selected or combined signals to the wireless or wired, or cabled, or internet medium, such as web (or WEB) or www, represented by Unit 1.8b. Single or plurality of signals are received on single or multiple antennas 1.11a and or on single or multiple interface points 1.11b and are provided to Splitter or switch Unit 1.12 for connecting one or more of the received signal(s) to communication devices, Unit 1.13, Unit 1.14, and/or Unit 1.15, respectively. Unit 1.15 is the receiver section of the transmitted signals of Unit 1.6, designated as OFDM or other. In other embodiments Unit 1.15 is receiver section of other signals, such as OFDM, infrared, WI-Fi, TDMA, FDMA, telemetry WLAN, WMAN, GSM, CDMA, WCDMA, or other signals or a combination of one or more of such signals. Signal selector or signal combiner Unit 1.16, provides one or multiple signals to interface or processor Unit 1.17. In some of the implementations, structures and architectures Units 1.6 and Unit 1.15 contain one or more of the following devices: interface devices, processors, modulators, demodulators, transmitters, receivers, splitters, combiners for one or more of OFDM, infrared, Bluetooth, Wi-Fi, TDMA, FDMA, FDM, telemetry, RFID, WLAN, MLAN, cellular systems, cable, wireless web wireless internet or other wired or internet systems.

In the transmitter part, shown in the upper part of FIG. 1, and also in the receiver part, illustrated in the lower part of FIG. 1, the selection or combing of signals is under the control of processors and or programs and/or manual control. The selection or combing of signals is not shown in FIG. 1. Interface and or processor Unit 1.17 interfaces to and or processes one or more of the received signals and may provide control signals to the receiver and also to the transmitter. Block arrows Unit 1.9 and Unit 1.10 designate signal and control path and or physical connections for processing and/or control of parts of the elements shown in FIG. 1.

Figure 2:
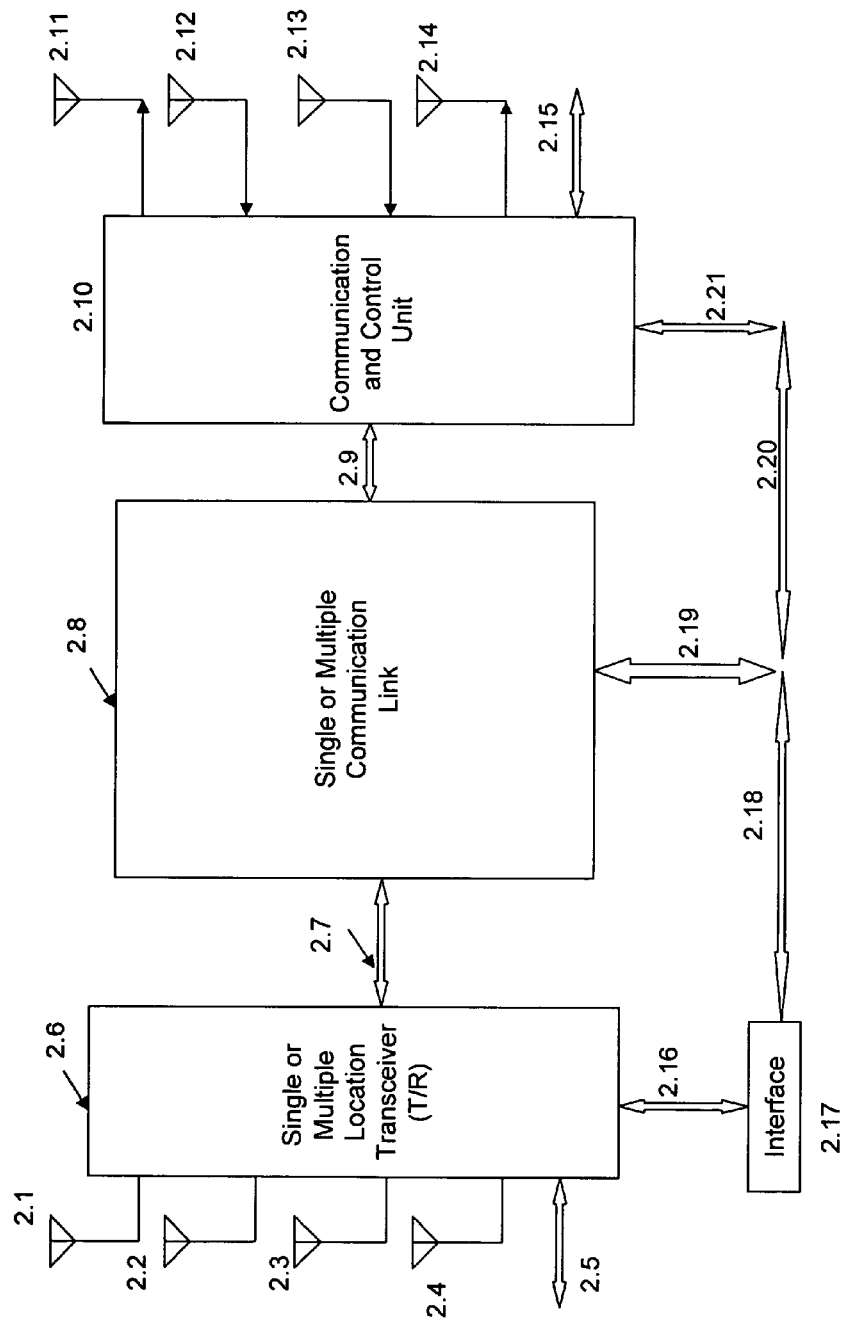
FIG. 2 is a structure of a multi mode location and multimode communication system, including wireless, wired (or cabled) and internet-web based connections with single or multiple communication links and or communication transceivers (T/R) and or communication and control units.

FIG. 2 is a structure of a multi mode location and multi-mode communication system, including wireless, wired (or cabled) and internet-web based connections with single or multiple communication links and or communication transceivers (T/R) and or communication and control units. One or more antennas Unit 2.1, Unit 2.2, Unit 2.3 and Unit 2.4, transmit or receive one or more signals. On block arrow Unit 2.5 one or more other signals are connected to the or from the single or multiple transceivers. Unit 2.6 is an interface unit or single or multiple transceivers connected to the signal transmission or signal reception medium. The signals from or to Unit 2.6 are connected with the single or multiple communication link, Unit 2.8. Interface Unit 2.17 through connections 2.16, 2.18, 2.19, 2.20, 2.21 and communication and control Unit 2.10 process signals and provide communication and control signals from or to antenna Units 2.11, 2.12, 2.13, 2.14, interface Unit 2.1S, interface connection Unit 2.17, antenna Units 2.1, 2.2, 2.3, 2.4 and interface connection Unit 2.5. All antenna units and connections 2.5 and connections 2.15 provide duplex (bi directional) signal transfers. Units 2.6 and 2.8 are in "cascade", i.e. they are connected to each other in a sequence. Communication and Control Unit 2.10 may also operate in cascade with one or more of Unit 2.6 or 2.8. In other embodiments, one or more of the units, shown in FIG. 2, are connected in parallel or a star or mesh network, or other configurations.

Figure 3:
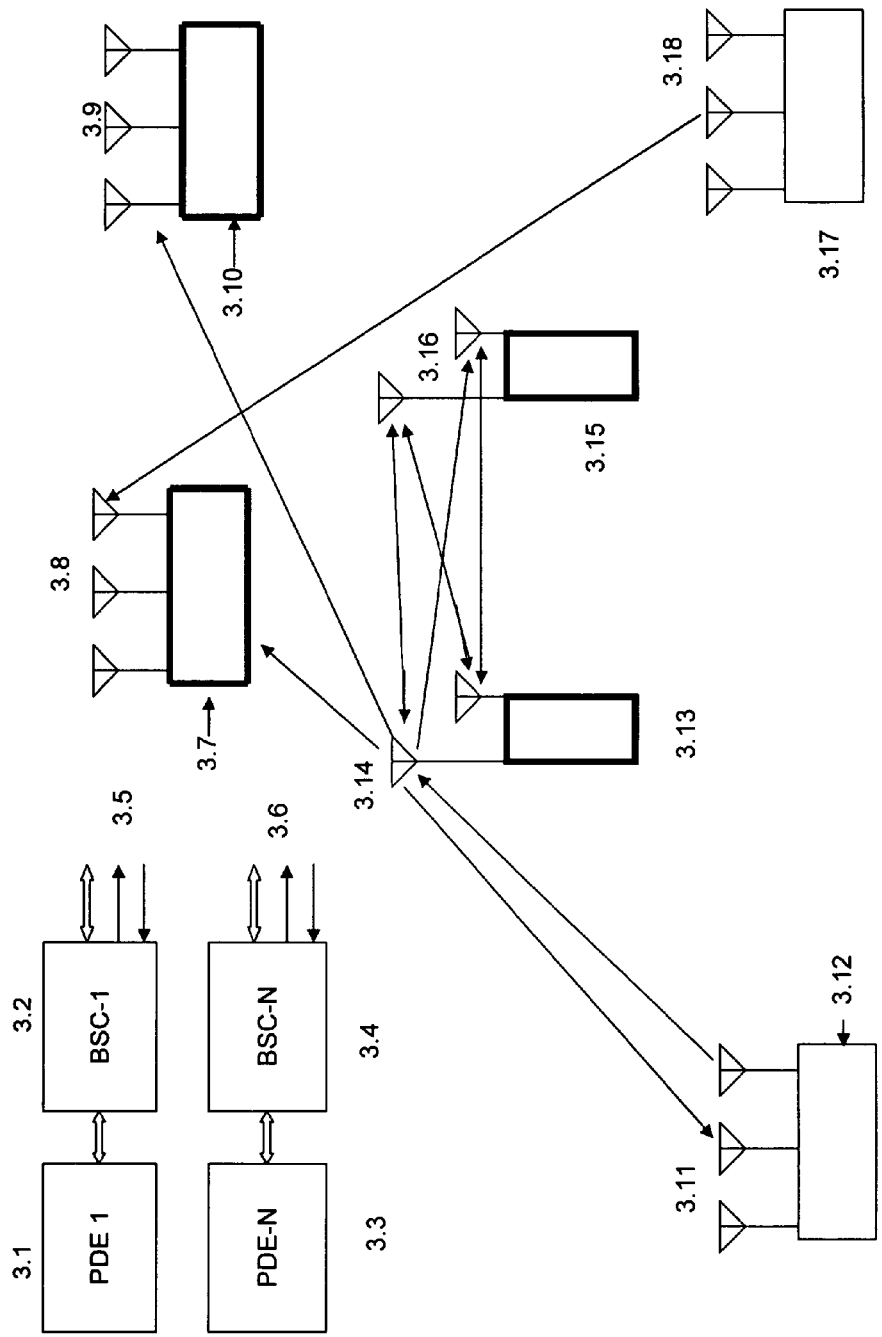
FIG. 3 is a structure of a system having single or a plurality of selectable Position Determining Entity (PDE), Base Station Controller (BSC), Terminal (Subscriber Unit) Base Station Transceiver Subsystem (BTS) devices.

FIG. 3 is a structure of a system having single or a plurality of selectable Position Determining Entity (PDE), Base Station Controller (BSC), Terminal (Subscriber Unit) Base Station Transceiver Subsystem (BTS) devices. While the cited prior art, such as Riley's U.S. Pat. No. 6,865,395 Ref 8, Qualcomm CDMA Technologies' MSM 6275 and Qualcomm CDMA Technologies' MSM 6300 chipset solution Ref 65 and Ref 66 disclose system and network operations of PDE, BSC, BTS and subscriber units, the prior art does not disclose nor anticipate the structures and connections of multi-mode, multi-purpose MFS systems operated in cascaded and or parallel, star or mesh configurations, selectable single or multiple single structures such as disclosed and claimed in this application. The term cascaded or cascade refers to units or devices operated in a sequence or in parallel with each others. FIG. 3 includes processing of Receiver or Location Finder Signals, e.g. GPS signals and or land line and or web-internet information signals and it includes Transmit Section of Multiple Communicator Devices. Elements (also designated as Units or Devices) 3.8, 3.9, 3.11, 3.14, 3.16 and 3.18 are single or multiple antennas which receive and or transmit signals from to a Position Determining Entity (PDE) transmitter or to one or more Base Station Transceivers (BTS) devices and/or to subscriber units, including peer to peer direct communication between subscribers. In some of the implementations transmitters of PDE signals include one or more satellite systems, such as GPS satellites, cellular base stations, wireless base stations or other wireless transmitters such as cellular phones PDA wireless transmitters, Remote Control (RC) transmitters, infrared or any other transmitters. Units 3.1 and 3.3 are interface units and or front end ports respectively, for reception of the PDE signals from the antennas, from infrared transmitters, from laser transmitters and or from wired connections or from the internet. Wired connections include fiber optics, copper, cable and any other connection. In some embodiments the Position Determining Entity (PDE) front end is a Remote Front end while in other cases it is co-located with the entire receiver. Units 3.2 and 3.4 are one or a plurality of Base Station Controller (BSC) units, designated as units BSC-1 to BSC-N. The BSC units control signals of the Base Station Transceiver Subsystem (BTS) units 3.7, 3.10, 3.12, 3.13, 3.15 and 3.17. Signal reception and or signal processing and or signal transmission by the antenna units or sets of antenna units 3.8, 3.9, 3.11, 3.14, 3.16 and or 3.18 is controlled by one or more BSC units or by controller devices located in the Base Station Transceivers (BTS), or by control devices located outside of these units.

Figure 4:
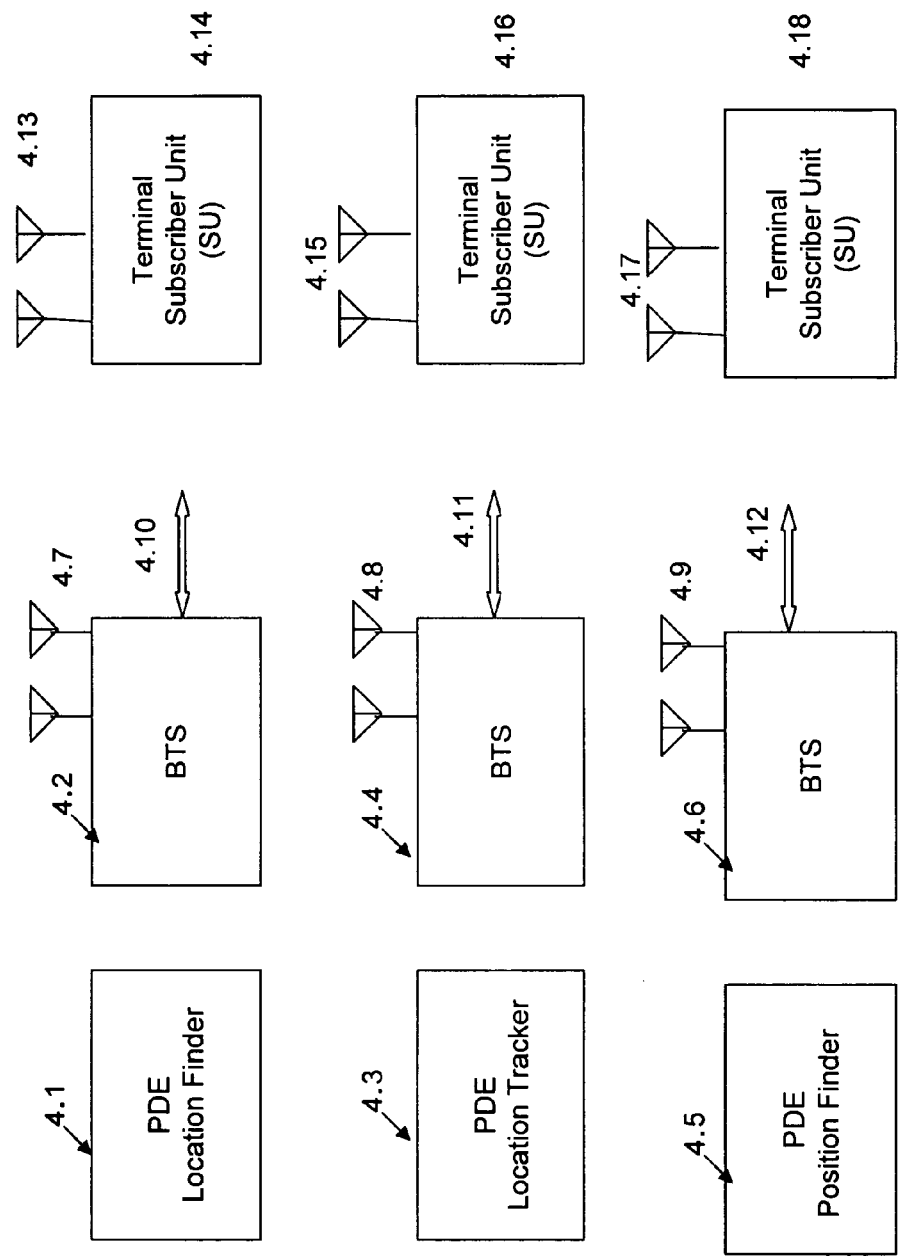
FIG. 4 shows embodiments and structures for systems and networks containing Multiple Position Determining Entity (PDE), Base Station Controller (BSC) units, Terminal or Subscriber Unit (SU) and Base Station Transceiver Subsystem (BTS) units.

FIG. 4 shows embodiments and structures for systems and networks containing Multiple Position Determining Entity (PDE), also designated as Position Determining Device (PDD), location tracker, location finder or position finder devices, Base Station Controller (BSC) units and Terminal or Subscriber Unit (SU) Base Station Transceiver Subsystem (BTS) units. Remote Control (RC), Universal Remote Control (URC), wireless, wired, cabled, internet, web based communication systems and communicator devices, radio frequency identification (RFID) systems with single or plurality of devices, emergency and other alarm systems, medical patient monitor-sensor devices, diagnostics units and systems, Deoxyribose Nucleic Acid (DNA) systems, fingerprint identification, fingerprint control and or using DNA samples for interactive communication or control of certain communications and control systems and systems having push to talk (PTT) options are included in some of the embodiments. Each unit may contain interface unit and or processor unit, memory, communication port, single or multiple modulator or transmitter(s) and single or multiple receivers and or demodulators with or without single or multiple switching selection devices and/or signal combining and splitting devices. Communications, telematics, telemetry, video broadcasting and or point to point video transmission, transmission of audio and or data and or video to mobile units is embodied by the implementation of single or multiple Bit Rate Agile (BRA), and single modulation format and or multimode Modulation Format Selectable (MFS), single bit rate and or multiple bit rate and or Bit Rate Agile (BRA) systems, such as enhanced performance or new features, new applications and new embodiment based GSM, General Packet Radio Service (GPRS), Enhanced Digital GSM Evolution (EDGE), or Evolution of GSM (E-GSM), Code Division Multiple Access (CDMA), Wideband Code Division Multiple Access (WCDMA or W-CDMA), Orthogonal Frequency Division Multiplex (OFDM), Time Division Multiple Access (TDMA), IEEE 802.xx, Digital European Cordless Telecommunication (DECT), Infrared (IR), Wireless Fidelity (Wi-Fi), Bluetooth, and other standardized as well as non-standardized systems, disclosed in this application. Units 4.1, 4.3 and 4.5 contain single or Multiple Position Determining Entity (PDE) devices, while Units 4.2, 4.4 and 4.6 are single or multiple BTS devices. Units 4.7, 4.8 and 4.9 are single or multiple transmit and or receive or transmit/receive antennas embodied as single band or multiple band antenna systems. Units 4.14, 4.16 and 4.18 are terminals, also designated as subscriber units (SU). In certain implementations the SU contain the PDE or position finder or location finder or location tracker unit, or RFID units. The BTS devices or BTS units communicate directly with the SC devices (units); in other applications some SC units communicate with other SC units without the use of BTS devices (also designated as BTS units). Block arrows 4.10, 4.11 and 4.12 show communication links between BTS, PDE and SC units and combinations of units, without the need to have all units in the network.

Figure 5:
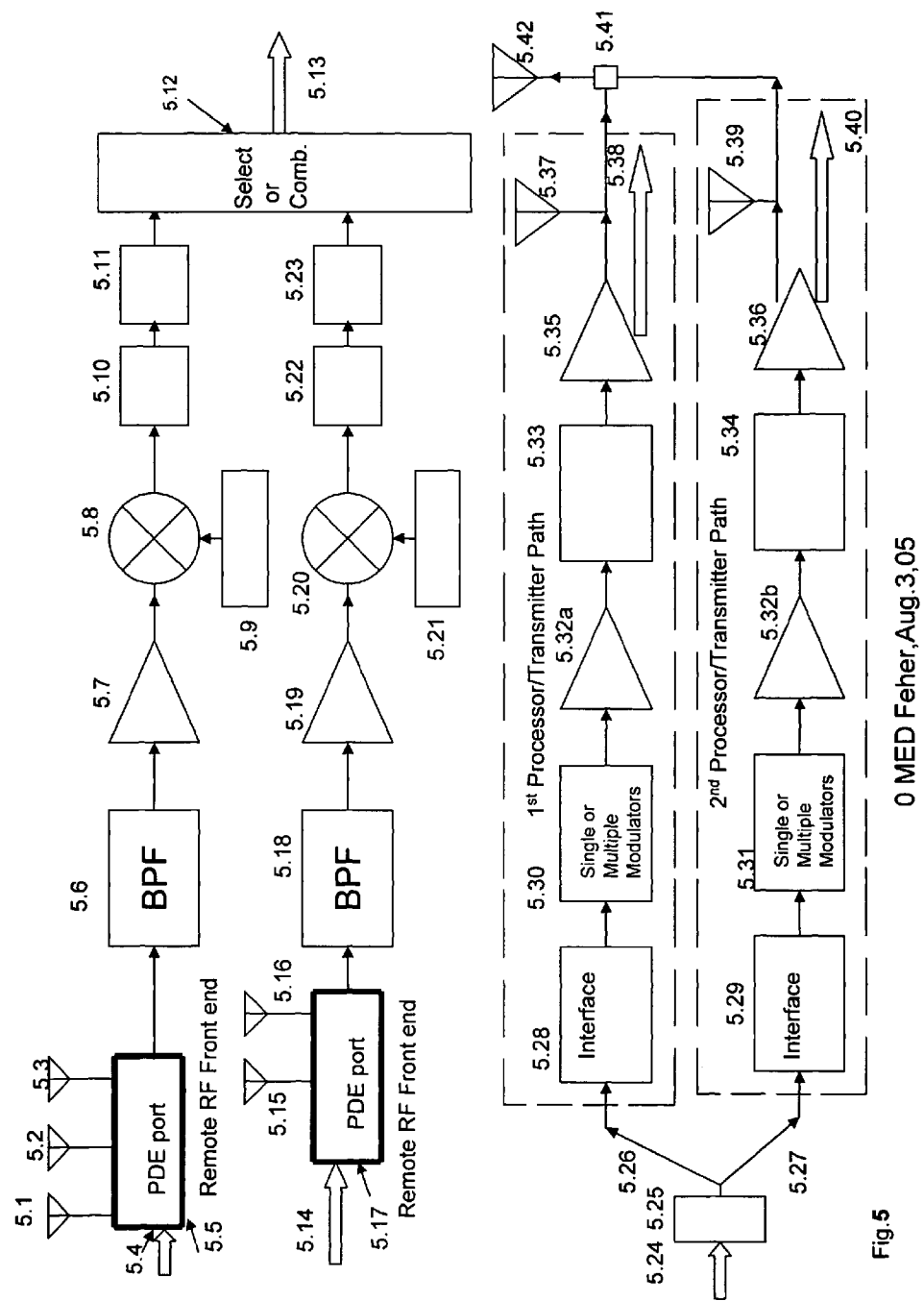
FIG. 5 represents implementation architectures and structures for single or multiple receiver and single or multiple transmitter signals, including location or position finder signals, from one or more antennas.

FIG. 5 represents implementation architectures and structures for single or multiple receiver and single or multiple transmitter signals, including location or position finder signals, e.g. wireless signals, cellular signals, GPS signals received from one or more satellites or from one or more ground (terrestrial) based single or plurality of antennas, Units 5.1, 5.2, 5.3, 5.15 and 5.16 or land line or world wide web (www) signals received by connections or interface units 5.4 and 5.14 which interface and or receive signals from Transmit Section of Multiple Communicator Devices. Multiple Position Determining Entity (MPDE) is also designated as Position Determining Device (PDD). The Position Determining Entity (PDE) ports/units 5.5 and 5.17, in certain cases are part of the entire receivers while in other cases are implemented at separate locations from other parts of the receivers and designated as remote RF front ends. In addition to the PDE ports, other units of the receiver are located at remote locations, from the subsequent parts of the receivers. Units 5.1 to 5.23 constitute parts of two receivers. Each unit is optional and not all units are required for the operation of the system. Units 5.6 and 5.18 are Band Pass Filter (BPF), Units 5.7 and 5.19 are amplifiers, Units 5.8 and 5.20 are signal multipliers (also known as mixers) for signal down conversion and Units 5.9 and 5.21 are frequency synthesizers or oscillators which provide signals to the mixers. Units 5.10, 5.22 and 5.11, 5.23 are demodulators and signal processors which provide, through an optional signal combiner or signal selector, Unit 5.12, demodulated and processed single or multiple output signals to connection lead 5.13. In direct radio frequency (RF) to baseband conversion receivers, or any other direct conversion receivers, including certain Software Defined Radio (SDR) implementations several aforementioned units are not used in the implementations. Units 5.24 to 5.40 are elements or devices of single or plurality of transmit sections of one or more transmitters of one or more communicator devices. Software Defined Radio (SDR) systems concepts, principles, SDR architectures and SDR technologies have been described in the prior art, including in the cited reference book Tuttlebee, W.: "Software Defined Radio: Baseband Technology for 3G Handsets and Basestations", John Wiley & Sons, Ltd., Chichester, England, ISBN 0-470-86770-1, Copyright 2004. On single or multiple input connections or leads 5.24 single or multiple signals are received from one or more input signal sources, signal processors, sensors, detection devices or other systems; these input signals or signal sources include one or more of the following signals obtained from: Video to mobile video transmitters, Video over Internet Protocol (ViIP), Voice over Internet Protocol (VoIP), wireless systems including GSM, GPRS, TDMA, WCDMA, CDMA, W-CDMA, Orthogonal Frequency Division Multiplex (OFDM), infrared (IR), Bluetooth, Wi-Fi, wired systems, cable connected systems and or a combination of wired/wireless and or internet web based systems, including mobile web, or mobile internet based systems. The signal or signals on connection lead 5.24, in certain implementations of FIG. 5, consist of one or more of the following signals, further also shown in FIG. 16 as elements 16.1 to 16.13 and 16.15: location tracker Unit 16.1, remote control (RC) or universal remote control (URC) Unit 16.2, video, digital video or video game Unit 16.3, digital camera, photo camera, scanner X-ray or any other image Unit 16.4, emergency or alarm signals or detector signals or diagnosis signals (such as obtained from medical sensors or devices) Unit 16.5, voice, music, recorded/stored music, sound recording, dictation recorded signals Unit 16.6, telemetry and/or diagnostics telemetry or space telemetry or other telemetry or telematics signals Unit 16.7, fingerprint or other personal identification and/or other signals, such as Deoxyribose nucleic acid (DNA) information and/or generated or obtained or processed signals from DNA samples. In this application the term DNA refers to customary prior art dictionary definitions of DNA such as: Deoxyribose nucleic acid (DNA) is a nucleic acid that contains the genetic instructions specifying the biological development of all cellular forms of life (and many viruses). In this application the term DNA refers also to more generic DNA definitions and to generic medical diagnostics and diagnostics obtained and related audible, visual, blood pressure, temperature, density, motion, and other diagnostics signals. In the lower part of FIG. 5, Unit 5.25, is a splitter or selector or combiner device. The terms splitter, selector and combiner device or unit mean that each of these terms describes devices which split or select or combine one or more input signals, process these signals and provide one or more output signals. On single or multiple connection lead or leads 5.26 a signal or multiple signals are provided to Unit 5.28 the input interface unit of the first ($1^{st}$) processor and or first transmitter path. On single or multiple connection lead or leads 5.27 a signal or multiple signals are provided to Unit 5.29 the input interface unit of the second ($2^{nd}$) processor and or second transmitter path. Input interface Unit 5.28 and interface Unit 5.29 provide signals to one or more single or multiple modulator Units 5.30 and 5.31. The modulated output signals of these units are provided to one or more amplifiers, Unit 5.32a and or 5.32b to optional filters 5.33 and 5.34, to subsequent amplifiers 5.35 and or 5.36 and to antennas 5.37 and or 5.39 and or to the wired or cabled or infrared transmission media on connection leads 5.38 and or 5.40. One or more of the mentioned amplifiers are operated in linearly amplified or linearized amplification mode and or in Non-Linearly Amplified (NLA) mode. While FIG. 5 shows two signal path (in the upper part of the figure) and two signal path (in the lower part of the figure), implementations have single and multiple mode signal path applications, including one or two or three or more signal paths. In some embodiments single selected signals are transmitted, while in other embodiments of this invention multiple signals are transmitted. In FIG. 5 one of the implementation structures has multiple transmitter path, connected to a single antenna 5.42. In some embodiments the amplified signal or the amplified signals are connected by a switch or selector or combiner 5.41 to antenna Unit 5.42. Antenna Unit 5.42 may consist of a single antenna or multiple antennas.

Figure 6:
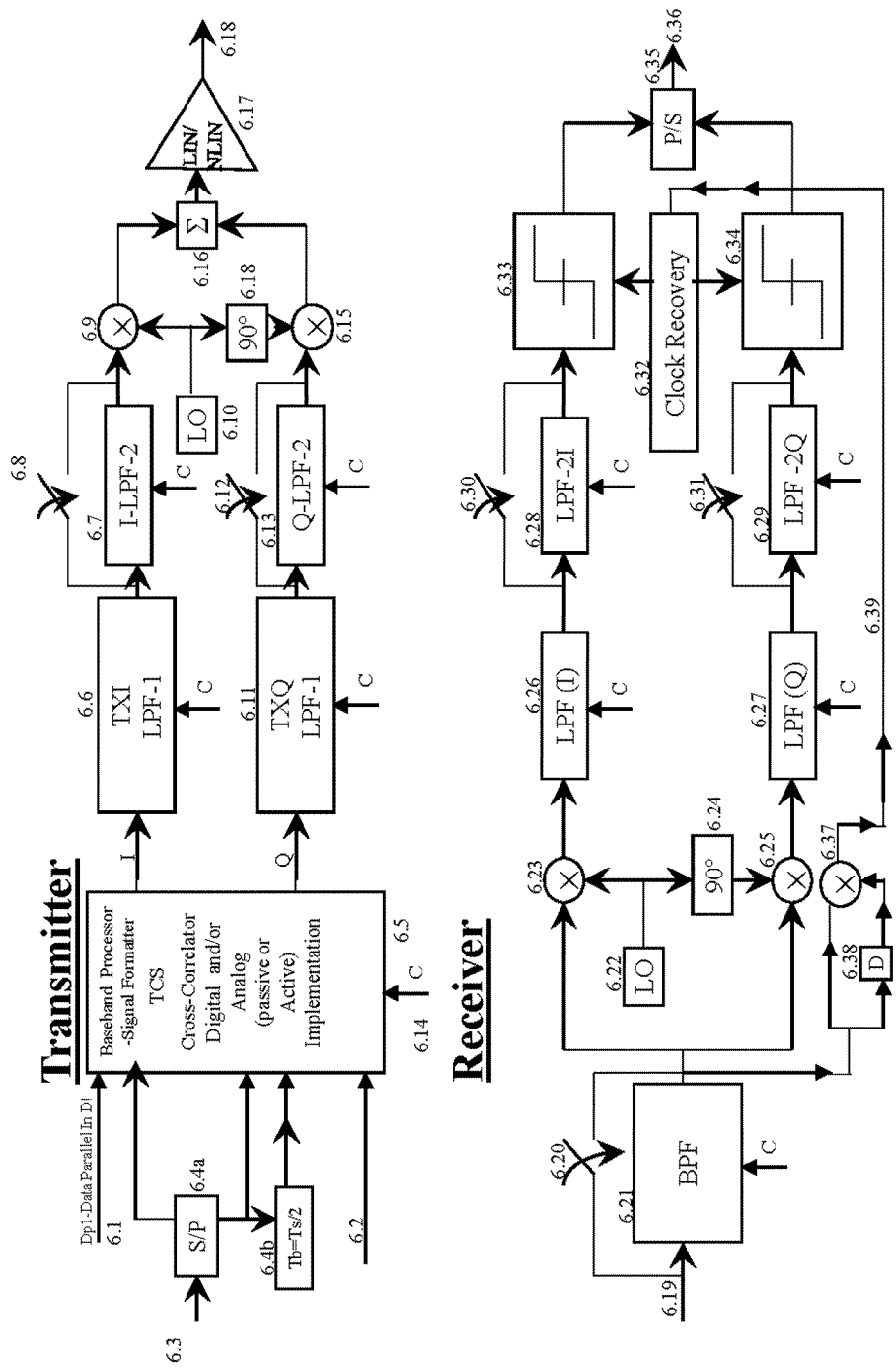
FIG. 6 is represents a generic prior art transmitter and receiver (transceiver or T/R), disclosed in Feher's U.S. Pat. No. 6,665,348 (the '348 patent).

FIG. 6 is represents a generic prior art transmitter receiver (transceiver or T/R), taken from the prior art FIG. 6 of Feher's U.S. Pat. No. 6,665,348 (the '348 patent), Ref.[42]. Since several terms used in the '348 patent and in the current application have the same and/or similar meaning as in the prior art and to facilitate reading of the current application, without the need to repeatedly refer to the '348 patent, in the following paragraphs pertinent highlights and or additional explanations of the prior art FIG. 6, of the '348 patent, within the context of this application, are presented. In FIG. 6 of the current application (which is taken from FIG. 6, of the prior art '348 patent) an implementation diagram with cascaded switched transmit (Tx) and receive (Rx) Low-Pass-Filters (LPF) in conjunction with cross-correlated and other non cross-correlated Time Constrained (TCS) waveform and cascaded Long Response (LR) filters or LR processors is shown. The terms cross-correlated or cross-correlation (abbreviated also as CC, or CCOR or Xcor) and cross-correlated have the descriptions, definitions and meanings as described in the cited prior art including Feher et al. U.S. Pat. Nos. 4,567,602; 5,491,457; 5,784,402; 6,445,749; 6,470,055; 6,665,348; 6,757,334 and in the book Feher, K.: "Wireless Digital Communications: Modulation & Spread Spectrum Applications", Prentice Hall PTR, Upper Saddle River, N.J. 07458, Copyright 1995, Book ISBN No: 0-13-098617-8. In general cross-correlated signals or cross-correlated waveforms means that signals (or waveforms) are related to each other. More specifically, the term "cross-correlating" means "processing signals to generate related output signals in the in-phase (I) and in the quadrature-phase (Q) channels". Related to description of FIG. 7, FIG. 8 and FIG. 9 it is noted that if a signal is split into two signal path or two signal channels and the signals in the two channels are the same, or practically the same, then the signals in the two channels are related thus, are cross-correlated. The term "cascade" or "cascaded" means that the signal flow or signal connection between filters or units is in a sequence, such as serial signal flow between filters, processors or units, or the signal flow or signal path is simultaneous or parallel between multiple units. In FIG. 6 the LR filters or LR processors could be implemented as separate in-phase (I) and quadrature-phase (Q) LPF s or as an individual time-shared LPF. The transmit Baseband Signal Processor (BBP) including the I and Q LPF s could be implemented by digital techniques and followed by D/A converters or by means of analog implementations or a mixture of digital and analog components. In certain embodiments only one signal path is present, that is there are no separate I and Q signal channels. Certain architectures use Bit Rate Agile (BRA), Modulation Format Selectable (MFS), modulation and demodulation filters have been implemented and tested with intentionally Mis-Matched (MM) filter parameters. Some of the implementations use Agile (Bit rate Agile or BRA) Cascaded Mis-Matched (ACM) architectures. The term Bit rate Agile or BRA refers to systems in which the bit rate is tunable, selectable or changeable. The LR filter units, embodied by the first and second sets of I and Q are implemented as LPF s or alternately as of other types of filters such as Band-Pass Filters (BPF) or High Pass Filters (HPF) or other filter/processor LR filter combinations. For several embodiments all of the aforementioned processors, filters and modulators, demodulators (modems) are BRA, MFS and ACM, while for other implementations bit rate agility and or ACM or MFS implementations may not be required. Unit 6.17 is an amplifier that could be operated in a linear (LIN) or in a NLA mode. The output of amplifier unit 6.17 is provided on lead 6.18 to the transmission medium. In some of the embodiments and structures the units in only one of the signal channels, e.g. the channel designated as the Q channel are implemented while in the other channel, designated as I channel the components are not used. In yet another set of embodiments only the baseband processor part is implemented. In FIG. 6 at the receiving end, on lead 6.19, is the modulated received signal. Unit 6.21 is a BPF that is present in some embodiments while in others it is not required. A more detailed description of Units 6.1 to 6.35 and embodiments and operation is contained in Feher's U.S. Pat. No. 6,665,348 (the '348 patent).

Figure 7:
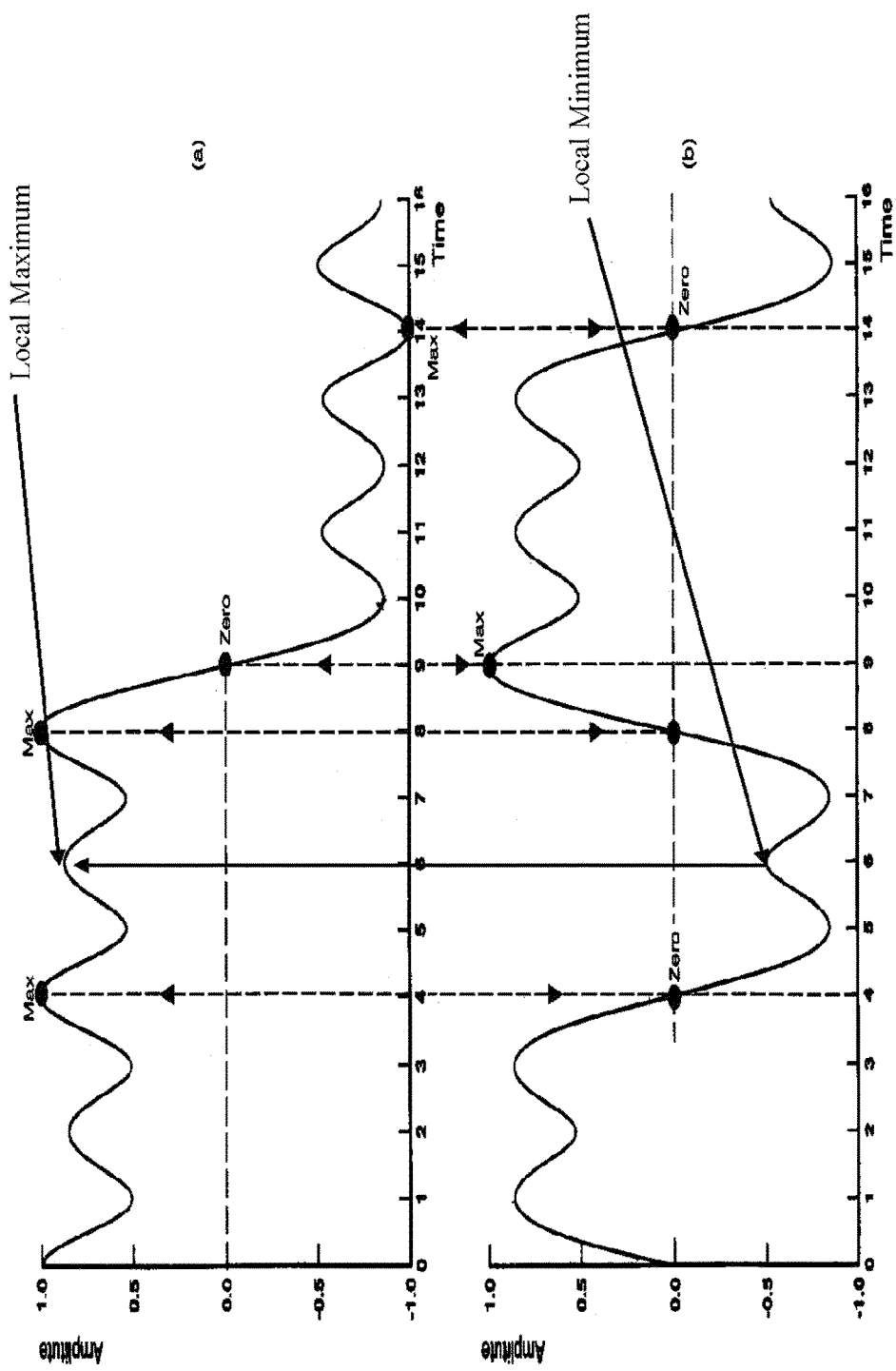
FIG. 7 shows prior art cross-correlated signals, and in particular in-phase (I) and quadrature-phase (Q) signal patterns-displayed in the time domain.

FIG. 7 contains prior art cross-correlated signals, and in particular in-phase (I) and quadrature-phase (Q) signal patterns-displayed in the time domain. This figure is taken from a prior art cited book, Feher, K.: "Wireless Digital Communications: Modulation & Spread Spectrum Applications". Note that the displayed amplitude patterns (amplitude as a function of time) of the upper signal (designated as I signal) and of the lower signal (designated as Q signal) are related, that is these signals are cross-correlated. This relation or cross-correlation property of the I and Q signals (upper and lower signals) is noted in FIG. 7, for example, whenever the upper signal (I signal) has its maximum amplitude, the lower signal (Q signal) has zero value and when the upper signal has a local maximum the lower signal has a local minimum. The term zero means zero or approximately zero, while the terms maximum and minimum mean maximum and minimum or approximately maximum and approximately minimum.

Figure 8:
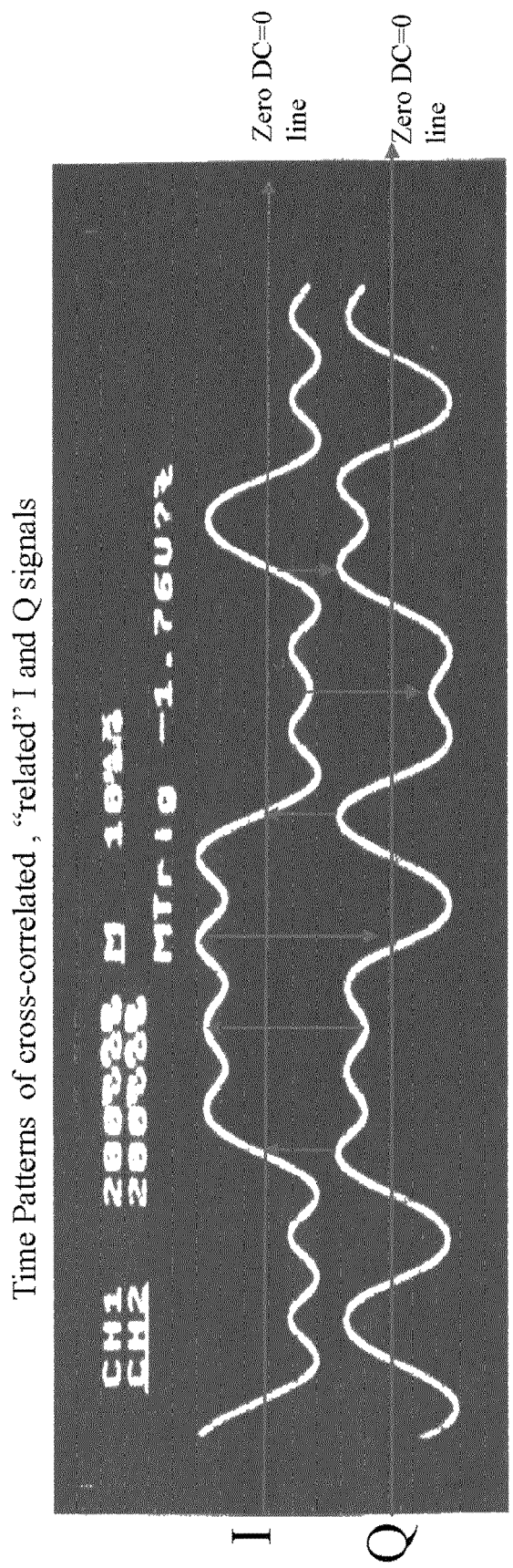
FIG. 8 presents prior art measured cross-correlated in-phase (I) and quadrature-phase (Q) baseband signals of a GMSK modulator, with BTb=0.3, specified for GSM systems.

FIG. 8 shows prior art measured cross-correlated signals on a sample Integrated Circuit (chip), manufactured by Philips and designated as the PCD-5071 chip. The Philips PCD-5071 chips was manufactured for use in GSM systems for generation of GSM system recommended/specified GMSK modulation signals. This FIG. 8 is taken from the prior art cited book Feher, K.: "Wireless Digital Communications: Modulation & Spread Spectrum Applications", Prentice Hall PTR, Upper Saddle River, N.J. 07458, Copyright 1995, Book ISBN No: 0-13-098617-8. The measured signal time patterns (or waveform) in the upper channel (designated as I signal) and in the lower channel (designated as Q signal) are related, i.e. they are cross-correlated. This cross-correlation or relation property between the upper and lower signals is evident, for example, whenever the upper signal (I signal) has its maximum amplitude, the lower signal (Q signal) has zero value.

Figure 9:
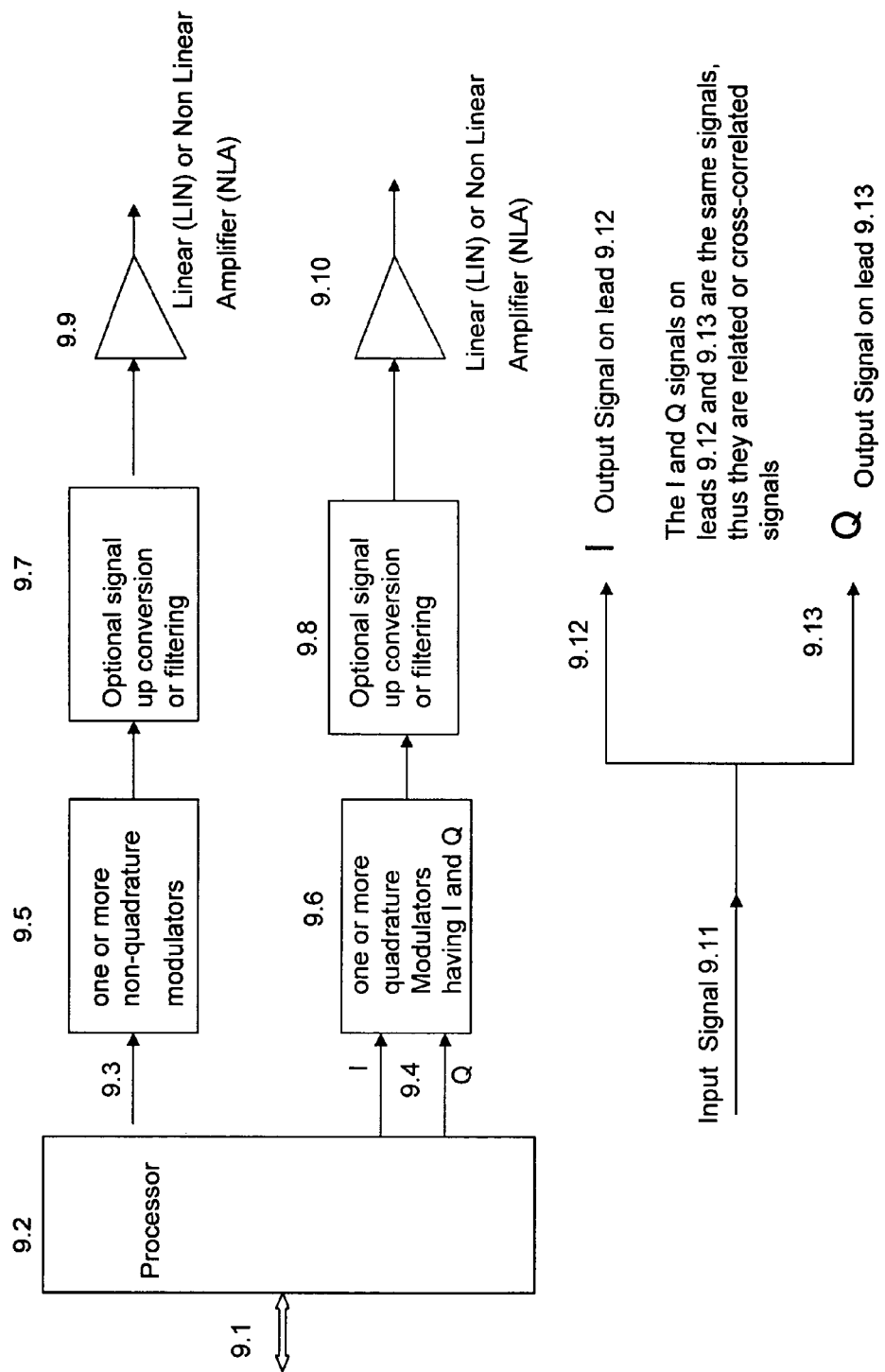
FIG. 9 shows Quadrature and Non Quadrature Architectures with one or more processors, and or single or multiple modulators and antennas.

FIG. 9 shows in the upper part of the figure one or multiple signals, connected on lead 9.1 to an interface unit 9.2 or processor unit 9.2. Interface and or processor 9.2 provides single or multiple signals on single or multiple leads 9.3 and or single or multiple leads 9.4 to one or more modulators. Unit 9.5 contains one or more non-quadrature modulation implementation structures such as prior art FM modulators and or polar modulators or other non quadrature modulators. Non quadrature modulators are modulators which have structures and implementations which are different from the quadrature (QUAD) implementation structures. Unit 9.6 contains one or a plurality processors and modulators which have a quadrature (QUAD) implementation structure. Modulators having quadrature structure have base band in-phase (I) signals baseband quadrature-phase (Q) signals connected to the inputs of the Quadrature modulators. An illustrative embodiment of a quadrature modulator structure is shown in FIG. 6. A prior art non-quadrature modulator embodiment is shown in the lower part of FIG. 13. Non-quadrature modulators are described in numerous prior art references; these are designated as FM modulators, FSK modulators, BPSK modulators or by similar and or related names and acronyms. Units 9.7, 9.8, 9.9 and 9.10 provide transmission processing functions such as filtering, up-conversion, and linear (LIN) or NLA signal amplification. In the lower part of FIG. 9, an input signal on connection 9.11, and connection of the 9.11 input signal to signal lead 9.12 and to signal lead 9.13 is shown. In one of the embodiments, the same input signal is provided (split or by the splitter) to the I channel, on connection 9.12, and to the Q channel on connection 9.13. Thus, the signals on connection leads 9.12 and 9.13, designated as I and Q signals, in this implementation architecture, are the same or are practically the same, thus they are related or cross-correlated signals. In other embodiments the splitter provides processed and different signals to leads 9.12 and 9.13 respectively, that is the I signal is different than the Q signal. The different I and Q signals, depending upon the processor/splitter may or may not be related, that is they may or may not be cross-correlated.

Figure 10:
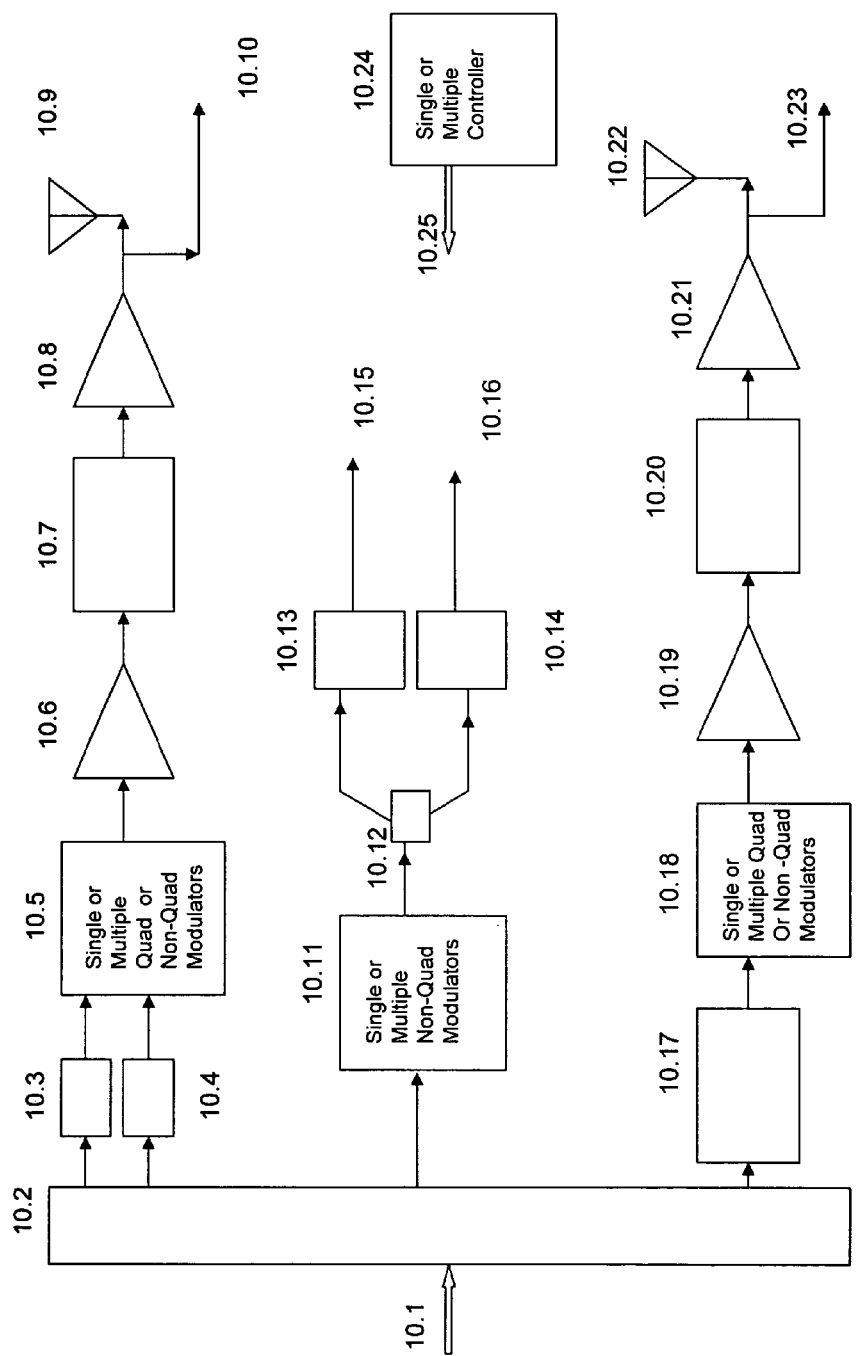
FIG. 10 is a multiple BRA and MFS transmitter architecture with one or more processors, modulators and amplifiers, antennas and interface connections) to wired or cabled or other transmission media.

FIG. 10 is a multiple BRA and MFS transmitter architectures with one or more processors, modulators and amplifiers, antennas and interface connection(s) to wired or cabled or other transmission media, including but not limited to mobile wired or wireless internet systems. On lead 10.1 one or more input signals are provided to signal interface Unit 10.2. These input signals could be analog, mixed analog and digital (hybrid) or digital baseband signals, such as prior art Non Return to Zero (NRZ) encoded or other digital signals. These input signals could be obtained from a sensor, from RFID devices, from motion detectors, video cameras, television or other picture and or image processors or from signals generated by a touch screen operation. Unit 10.2 provides one or more signals to one or more quadrature (designated also as QUAD or quad) baseband signal processors Units 10.3 or 10.4 and or to one or more non-quadrature baseband signal processors included in Unit 10.17. These baseband signal processors interface, process and or generate one or more of OFDM, CDMA, W-CDMA or WCDMA, CDMA-2000, CDMA EVDO, other CDMA, other spread spectrum or TDMA, or continuous data streams analog or digital signals for modulation. The embodiment of FIG. 10 is for multiple BRA and MFS signal processing, modulation and transmission and or for single modulation format or single modulation format selected systems. The term Bit Rate Agile (BRA) means that the bit rate is selectable or tunable or adaptable to the system requirements and system objectives and the term Modulation Format Selectable (MFS) means that various modulation formats can be selected and or that the modulation type or modulation types are adaptable to the system or user requirements. Units 10.5, 10.11 and 10.18 are single or plurality of non-quadrature or quadrature modulators. Units 10.6, 10.7, 10.8, 10.9, 10.10, 10.13, 10.14, 10.15, 10.16 and 10.19 to 10.23 are optional amplifiers, filters, signal conditioners or signal processors antennas and interface points to wired or cabled transmission systems. Single or multiple controller Unit 10.24 controls through control signals present on connections or leads or software control algorithms on 10.25 the selection or combining process of one or more signals and controls which signals should be connected to the transmission medium and when should the selected and or combined signals be transmitted. Unit 10.11 receives signals from interface or processor Unit 10.2. Unit 10.11 contains non-quadrature (also designated as non quadrature or non-QUAD or non-quad) modulators.

FIG. 11*a* is a new implementation architecture and block diagram of a multiple communication link, also designated as a cascaded link, or a system having cascaded units which inter operate in a sequence for multimode operated wireless and or wired and internet systems including fixed location systems and mobile systems. Unit 11.1 contains one or more of the following devices or signals generated by these devices: a location finder, also designated as a Position Determining Entity (PDD) or Position Determining Device (PDD), a medical apparatus a diagnostic device, voice processor, data processor, image processor, digital camera processor, video processor, a finger print stored or processed signal or image, DNA signal processors, music, other storage devices or a screen touch generated or processed signal. One or more signals contained in Unit 11.1 are provided to Unit 11.2 containing a short range system, such as a WLAN, Bluetooth, infrared or other communication system or sub system. The short range systems are connected to an optional medium range communication system, Unit 11.3. The medium range system provides signals to one or more remote units, designated as Unit 11.4 of the system. The remote unit provides signals to the interface unit or units of the transmission medium, designated as Unit 11.5. The signal path is implemented from the location finder, Unit 11.1 to the interface Unit 11.5 and also in the opposite direction from interface Unit 11.5 to the location finder. The units in this structure, in one of the embodiments have fixed parameters while in an other embodiment are BRA and MFS units operated in a single or in plurality of multi mode systems. In the embodiments of units 11.1 to 11.5 optional modulation devices and circuits are included. The prior art implemented modulation circuits have two distinct implementation architectures. One of the implementations is known as quadrature modulator (also designated as QUAD-mod or quad mod) and the second implementations is known as polar modulation and or designated herein as non-Quadrature, or non-QUAD modulation.

Figure 12:
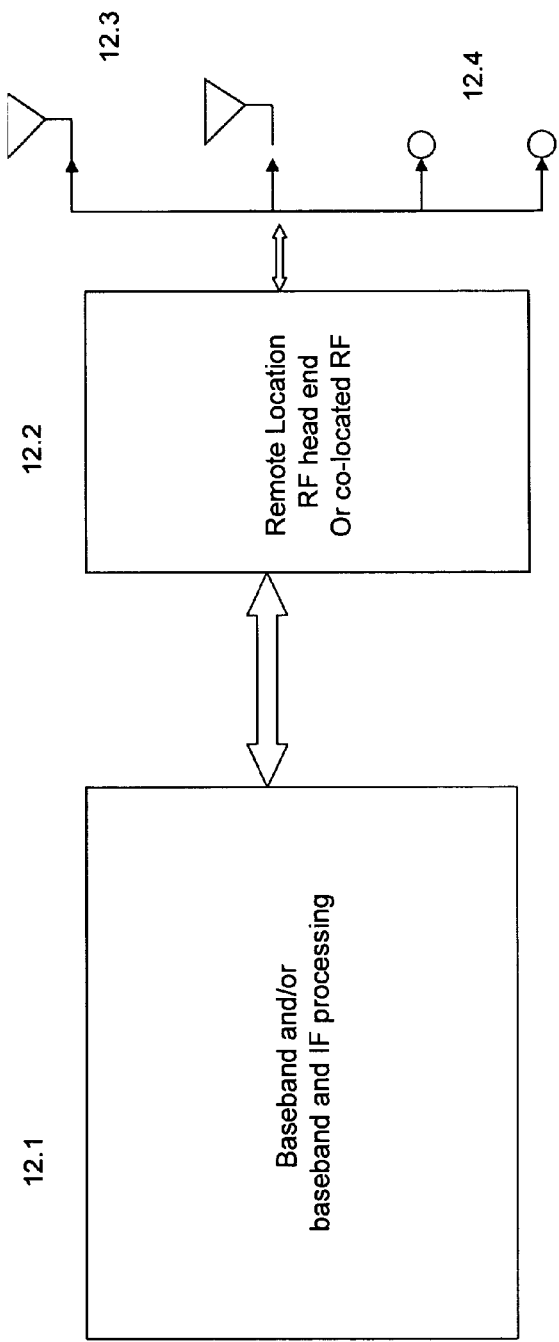
FIG. 12 is an embodiment of an RF head end (alternatively designated as RF subsystem or RF part) which is co-located with the baseband and or Intermediate Frequency (IF) processing units, or is at a remote location.

FIG. 11*b* shows an exemplary prior art quadrature modulator. In a later part of this application, in the description of FIG. 17*b* and FIG. 17*c* two prior art polar and or non-QUAD architectures are described. In the exemplary prior art quadrature modulator, shown in FIG. 11*b*, the input source signals, present on leads 11.6 and 11.7 are connected to optional Digital to Analog (D/A) converters 11.8 and 11.9. These input signals are also known as in-phase (I) and quadrature-phase (Q) signals. The I and Q signals are provided to optional filters, shown as 11.10 Filter-I and shown as 11.11 Filter-Q. The input signals on leads 11.6 and or 11.7 may include such signals as a microphone, video camera, photo camera, facsimile, wireless internet connection, modem, or other source of customer, subscriber, or other user data signals or converted processed signals. The optionally D/A converted and or optionally filtered I and Q signals, or the signals present on input leads are provided to two multipliers (also known as mixers), designated as Unit 11.13 and Unit 11.16. These multipliers receive also an unmodulated carrier wave from a frequency source or frequency generator, designated in the figure as Local Oscillator (LO), unit 11.12. In particular mixer 11.13 is provided by an unmodulated carrier wave (CW) signal on lead 11.14, while mixer 11.16 is provided a CW signal which is 90 degrees phase shifted from the signal provided to mixer 11.13. Mixer 11.16 receives the 90 degree phase shifted signal from the 90 degree phase shifter unit, Unit 11.15. The outputs of mixers 11.13 and 11.16 are provided to the inputs of a summing device 11.17. The output of summing device 11.17 is the quadrature modulated signal. It is provided to an optional signal amplifier (Amp1). The modulated signal is provided on lead 11.9 to the transmission medium FIG. 12 is an embodiment of an RF head end (alternatively designated as RF subsystem or RF part) which is co-located with the baseband and or Intermediate Frequency (IF) processing units, or is at a remote location. Remote location means that there is a separate physical unit (enclosure or box) other than is the unit and/or location of the baseband processing (BBP) and or Intermediate Frequency (IF) units. Unit 12.1 contains the BBP and or IF devices while Unit 12.2 is the RF head. The BBP circuits in Unit 12.1 in some embodiments have single processors, for processing a single baseband signals, while in other embodiments contain multitude of baseband processors and or multitude of IF or multitude of RF processors, or multitude of RF head ends for processing of more than one signal. The RF head includes one or more of the following Radio Frequency (RF) components: RF amplifiers, RF filters, circulators, RF splitters or RF combiners, RF diplexers, RF switches, and or RF cables or connections including fiber optic communication (FOC) links. Unit 12.3 is the embodiment of one or more transmit and/or receive antennas and Unit 12.4 is the structure for one or more interface elements, for interfacing the signals from or to Unit 12.2 to the wired or cabled or FOC communications or broadcasting medium. All signals are enabled to flow from Unit 12.1 to Units 12.3 and 12.4 and in reverse directions from Units 12.3 and or Unit 12.4 towards Unit 12.1. The embodiments and operation of FIG. 12 include multi operation and multi function of a plurality of systems including: single or multiple location finder, location tracker devices, position finder devices, Radio Frequency Identification Devices (RFID), connected with single or multiple Bit Rate Agile (BRA), and single modulation or Modulation Format Selectable (MFS) satellite and/or land based devices. These systems components assembled in one or more combinations and variations operate in GSM, General Packet Radio Service (GPRS), Enhanced Digital GSM Evolution (EDGE), or Evolution of GSM (E-GSM), Code Division Multiple Access (CDMA), Wideband Code Division Multiple Access (WCDMA or W-CDMA), Orthogonal Frequency Division Multiplex (OFDM), Time Division Multiple Access (TDMA), IEEE 802.xx, Digital European Cordless Telecommunication (DECT), Infrared (IR), Wireless Fidelity (Wi-Fi), Bluetooth, and other standardized as well as non-standardized systems. FIG. 12 operations include single mode and or multimode communication systems with co-located and remote located RF heads with single and or plurality of antennas.

Figure 13:
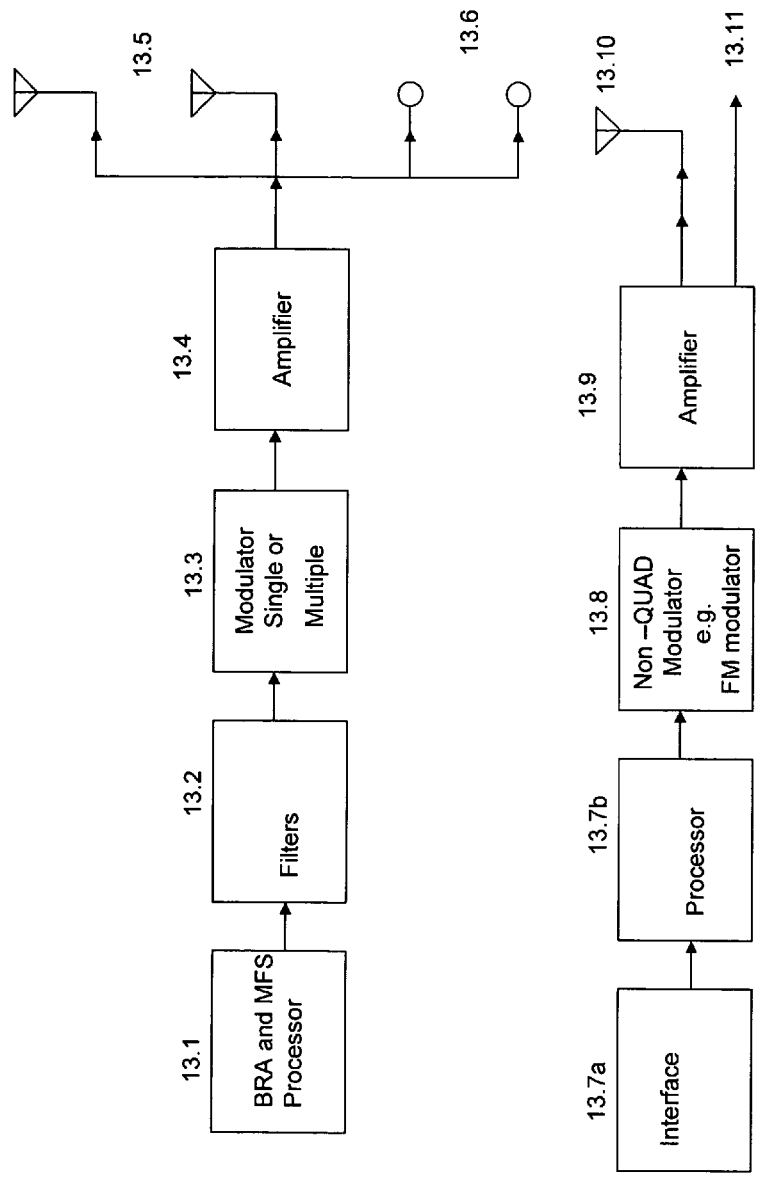
FIG. 13 represents an alternative embodiment of a multi mode BRA and MFS system connected to single or multitude of wireless, wired, cabled or fiber optic communication (FOC) connected and or internet or mobile internet web based systems.

FIG. 13 represents an alternative embodiment of a multi mode BRA and MFS system connected to single or multitude of wireless, wired, cabled or FOC connected and or internet or mobile internet web based systems. A single bit rate and or a Bit Rate Agile (BRA) baseband processor and a single modulation format and/or Modulation Format Selectable (MFS) system structure is shown. Units 13.1 to 13.4 are the embodiments of single bit rate and or single modulation format processors and or of multiple bit rate or BRA and MFS processors, filters, modulators and amplifiers. The single or multiple amplified signals of the communication structure are provided to interface points and to single or multiple antennas for wireless transmission, shown as antennas 13.5, and or to interface points 13.6 for systems having physical hardware or firmware connections or connectors. Units 13.1 to 13.4 may contain single processors, filters and or modulators or may contain a multitude of processors, filters and or modulators which are connected in a cascade (serial mode) or parallel or other configuration. Unit 13.2 contains one or more Time Constrained Signal (TCS) processors and or Long Response (LR) filters. The signals processed and or filtered in Unit 13.2 are provided to single or multiple modulators, contained in Unit 13.3. In one of the embodiments, the modulators in Unit 13.3 are quadrature (QUAD) modulators, while in an other embodiment they are non-quadrature (non-QUAD) modulators, while in an other implementation structure or embodiment they are a combination of single or multiple QUAD and single or multiple non-QUAD modulators. Some of the QUAD-modulators have cross-correlated in-phase (I) and quadrature-phase (Q) baseband signals, while other QUAD-modulator embodiments have no cross-correlation between the I and Q baseband signals. In some of the implementations the transmit filters are matched to the receive filters, while in other embodiments intentional mis-match between the transmit processor/filter and receiver processor/filters is implemented. A prior art non-quadrature modulator embodiment is shown in the lower part of FIG. 13. Non-quadrature modulators are described in numerous prior art references; these are designated as FM modulators, FSK modulators, BPSK modulators or by similar and or related names and acronyms. Interface Unit 13.7a provides signals to optional processor 13.7b. Processor 13.7b implementation structures is an analog or digital or a hybrid (mixed analog and digital) baseband processor. The processed baseband signal is provided to non-quadrature modulator, Unit 13.8 for modulation and connection to amplifier unit 13.9 for modulated signal amplification. The amplified signal is provided to the transmission medium, antenna Unit 13.10 or to the wired or cabled transmission mediums interface Unit 13.11.

Figure 14:
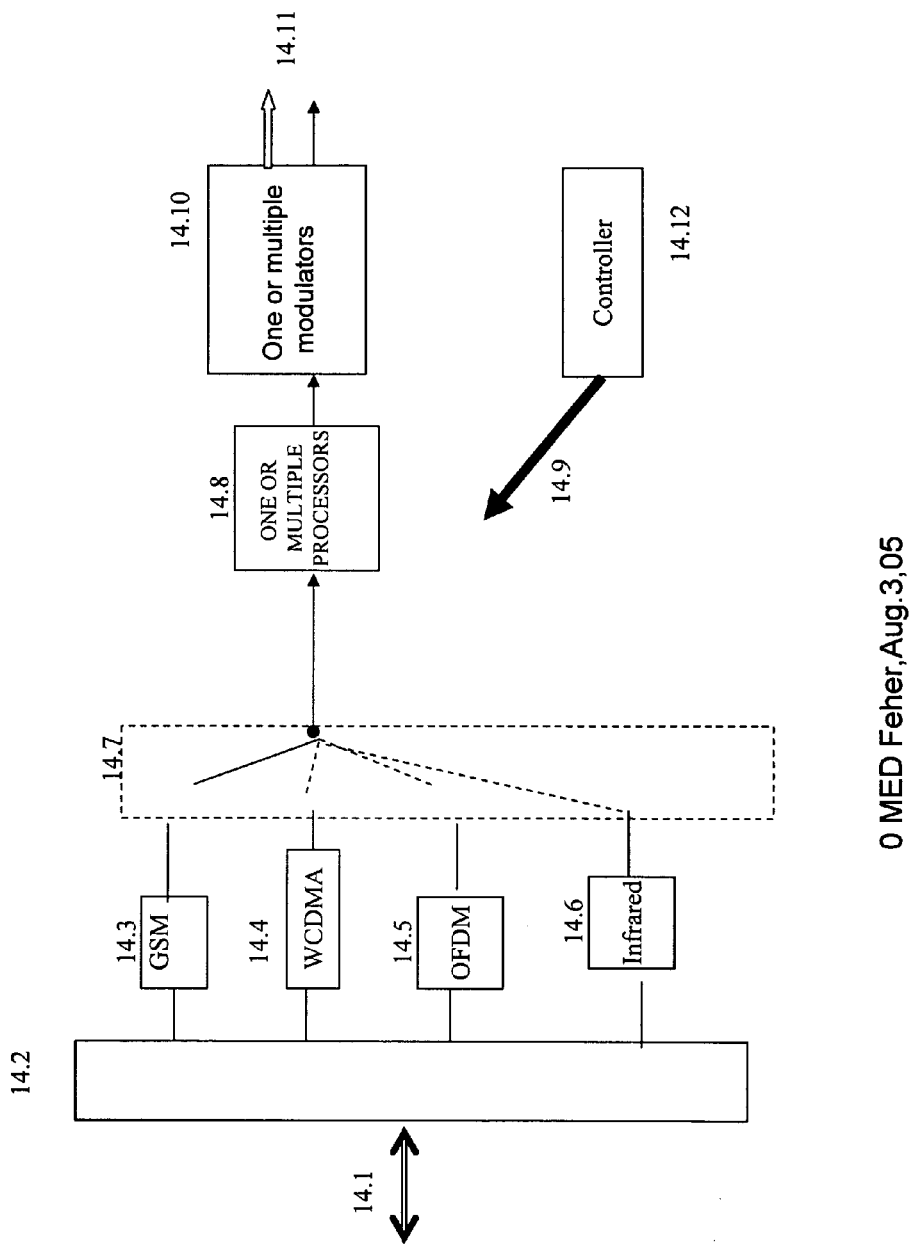
FIG. 14 is an embodiment of a multi-mode, multi bit rate system, with BRA, MFS and code selectable OFDM, WCDMA, Wi-Fi, Wi-Max, WLAN, infrared, Bluetooth and or other spread spectrum or continuous data systems.

FIG. 14 is an embodiment of a multi-mode, multi bit rate system, with BRA, MFS and code selectable OFDM, WCDMA, Wi-Fi, WLAN, infrared, Bluetooth and or other spread spectrum or continuous data systems. The embodiments include connection and or elements or units of the system architecture operating in a single mode or simultaneous multi-mode configuration. On single lead or multiple lead 14.1 input analog and/or digital and/or hybrid signals are provided to interface and or processor unit 14.2. Hybrid signals contain combination of single or multiple analog and/or digital signals. The signal or signals on input lead 14.1 contain in certain embodiments video signals or audio signals or signals obtained from processed photography, DNA samples, fingerprints, touch screen control or identification signals, RFID signals, telemetry, telematics, Remote Control processed signals or other web or www based communication or broadcast signals. Interface processor may comprise a simple connection device, or a splitter or o a combiner or a signal processing circuit with one or more output connection leads. The single or multiple output signal(s) are provided to Units 14.3 to 14.6 for signal interface and/or further processing. As shown in FIG. 14 these units contain one or more of the following interface units (connections) and/or signal processors: Unit 14.3 is a GSM and/or GPRS and/or EDGE connection and/or signal processor, Unit 14.4 is a connection and/or spread spectrum signal processor, for example a Code Division Multiple Access (CDMA) processor, an other type of Direct Sequence Spread Spectrum (DS-SS) processor, a Frequency Hopped Spread Spectrum (FH-SS) processor, a Collision Sense Multiple Access (CSMA) spread spectrum connection lead and/or processor or an other variation of spread spectrum processors. Unit 14.5 is an OFDM signal connection and/or processor, while Unit 14.6 is an interface unit connection and/or processor for one infrared signal or a plurality of infrared signals. In some of the implementations only one of the Units 14.3-14.6 is used, while in other embodiments a combination of these units is embodied. In alternate implementations the interface or processor for one of the shown designated processors is replaced by Wi-Fi, or other interfaces such as Fiber Optic Communication (FOC), or cable systems or other wired and/or wireless system interfaces. One or multiple output signals of Units 14.3-14.6 are connected to a selector (switch, combiner or splitter or similar device), Unit 14.7 and provided to one or multiple processors embodied in Unit 14.8. One or more output signals, from Unit 14.8, are connected to one or multiple modulators, shown in Unit 14.10. The output or outputs of 14.10 are connected to single or multiple transmit interface points shown as Unit 14.11. A controller, Unit 14.12 provides control signals 14.9 to one or more Units, shown in FIG. 14, for selection and/or processing of one or more signals and/or connection of the selected signals to the transmission interface unit(s) 14.11.

Figure 15:
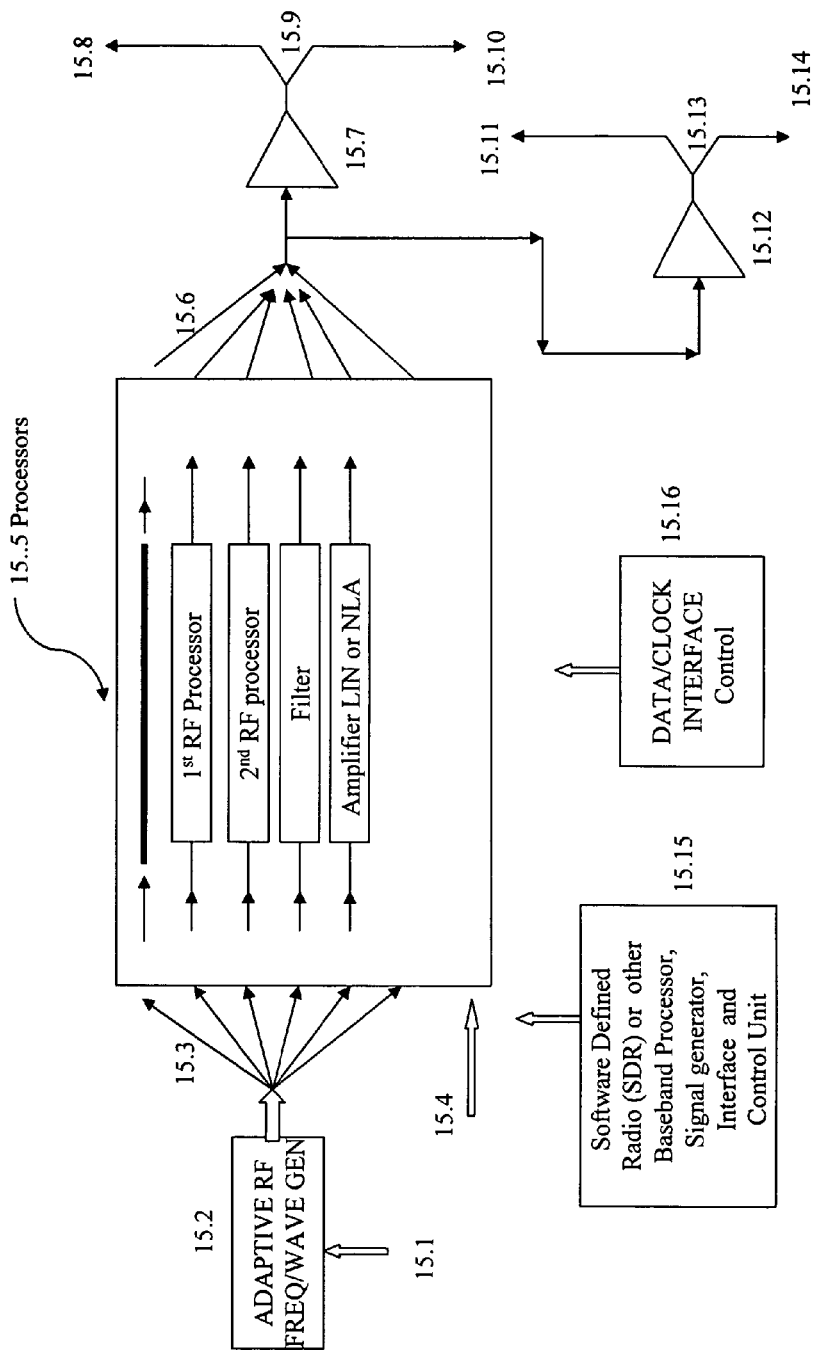
FIG. 15 is an adaptive Radio Frequency (RF) wave generator, RF processor, radio and modulator structure.

FIG. 15 is an adaptive Radio Frequency (RF) wave generator, RF processor, radio and modulator structure. The implementation includes baseband processor, interface and control unit, data clock interface and RF amplifiers, RF splitters or RF switch device and antennas. The implementation embodiments are for single or multi-mode modulation formats and or for Modulation Format Selectable (MFS) and Bit Rate Agile (BRA) systems. The term Bit Rate Agile (BRA) means that the bit rates are adaptable or selectable. Specifically the embodiment of a direct baseband to RF transmitter, such as used in Software Defined Radio (SDR) systems, with or without multiple transmitters and with or without diversity is used. A frequency source signal is provided on single lead 15.1 or multiple leads 15.1 to adaptive RF frequency and or RF wave generator Unit 15.2. The source signal, on lead 15.1 consists of a frequency reference source, such as an oscillator, or a Phase Locked Loop (PLL), or a numerically controlled oscillator, or a frequency synthesizer, or a clock signal received from an other system, or an unmodulated carrier wave (CW), or any other signal source. In certain embodiments RF frequency and or RF wave generator Unit 15.2 is merely an interface unit which provides to one or multiple leads (connections) 15.3 the signal received on lead (connection) 15.1. In other embodiments RF frequency and or RF wave generator Unit 15.2 is an adaptive RF agile (RFA) signal processor and signal generator. In some embodiments the RFA generator comprises a frequency synthesizer for the generation of multitude of unmodulated CW signals, in other embodiments it generates one or a plurality of unmodulated or modulated RF signals. The generated RF signals might have a sinusoidal wave shape or rectangular wave shape or other wave shapes or waveforms and one or more of the RF signals, provided to connections 15.3 are periodic or non-periodic signals. On single or multiple connections (connections are also designated as leads) 15.4 control signals, obtained from units 15.15 and or 15.16, are provided to the processor Unit 15.5 for control, selection and further processing of one or more selected RF signals provided on leads 15.3 to processor 15.5. RF Processor Unit 15.5 contains input selectors, for selecting one or more of the signals, received on leads 15.3 and it also contains output selectors for selecting and providing one or more of the output signals to leads 15.6 and subsequent connection of the selected output signals to one or multitude of amplifiers 15.7 and or 15.12. Unit 15.15 is an interface and or a processor unit, which includes an interface circuit and optional processor circuits for signal conversion, e.g. Analog to Digital (A/D) signal conversion, Digital to Analog (D/A) signal conversion; converters and or transducers for conversion of temperature, blood pressure, heart rate, fingerprint, DNA; touch screen (pressure or mere physical touch), motion detector, interactive, emergency sensors and or activators of emergency signals (e.g. smoke fire or heat detectors), excess humidity or flood or water level sensors, audio and or video signals, scanned images, RFID generated signals, location based signals and/or other signals into processed electrical, optical, Infrared or other signals. One of the implementation structures of Unit 15.15 includes parts of the baseband circuitry of a Software Defined Radio (SDR) and or the entire or the entire software part and or hardware or firmware parts of the non RF parts of a SDR. Since the principles and technologies of Software Defined Radio (SDR) implementations and structures were disclosed in the prior art, including in Hickling, R. M.: "New technology facilitates true software defined radio", RF Design Magazine April 2005, Tuttlebee, W.: "Software Defined Radio: Baseband Technology for 3G Handsets and Basestations", John Wiley & Sons, Ltd., Chichester, West Sussex, England, Copyright 2004, ISBN 0-470-86770-1, and patents such as U.S. Pat. No. 6,906,996, issued to Ballantyne, G. J., Assignee Qualcomm, Inc., and U.S. Pat. No. 5,430,416, issued to Black et al., Assignee Motorola, there is no need to include additional details of SDR in this Application. Processor Unit 15.5 contains one or more optional circuits. Within Unit 15.5 there are input signal leads (arrows), shown on the left hand side, and output signal leads shown on the right hand side. In Unit 15.5 the bold line represents a signal connection between a selected signal from input lead 15.3 and output lead 15.6. The signal present on the bold line, (representing a connection) may be selected or not selected. The $1^{st}$ RF processor, $2^{nd}$ RF processor, Filter, Amplifier LIN or NLA are implementations of different processors and or different modulators. The implemented modulators are in some implementations quadrature (QUAD) modulators, while in other embodiments they are non-quadrature (non-QUAD) modulators, such as polar modulators. In certain designs the amplifiers operate in a relatively linear mode (LIN amplifier) while in other embodiments they operate in a Non-Linearly Amplified (NLA) mode, close or at saturation. In an other implementation the amplifiers may be switched or adapted to operate in a LIN or in a NLA mode. In certain implementations a multiple number of the aforementioned RF processor and or modulators, filters and amplifiers are used. The Interface and or Control Unit 15.5 in combination with the data clock interface unit 15.16 selects one or more of the output signals and connects the single or multitude of selected Unit 15.5 output signals to one or more optional amplifiers 15.7 and or 15.12. One or a plurality of the output signals is provided to one or more of the transmission media interface points, shown as 15.8, 15.10, 15.11 and 15.14. Elements 15.9 and 15.13 are optional signal switch or splitter or combiner or duplexer or diplexer units.

Figure 16:
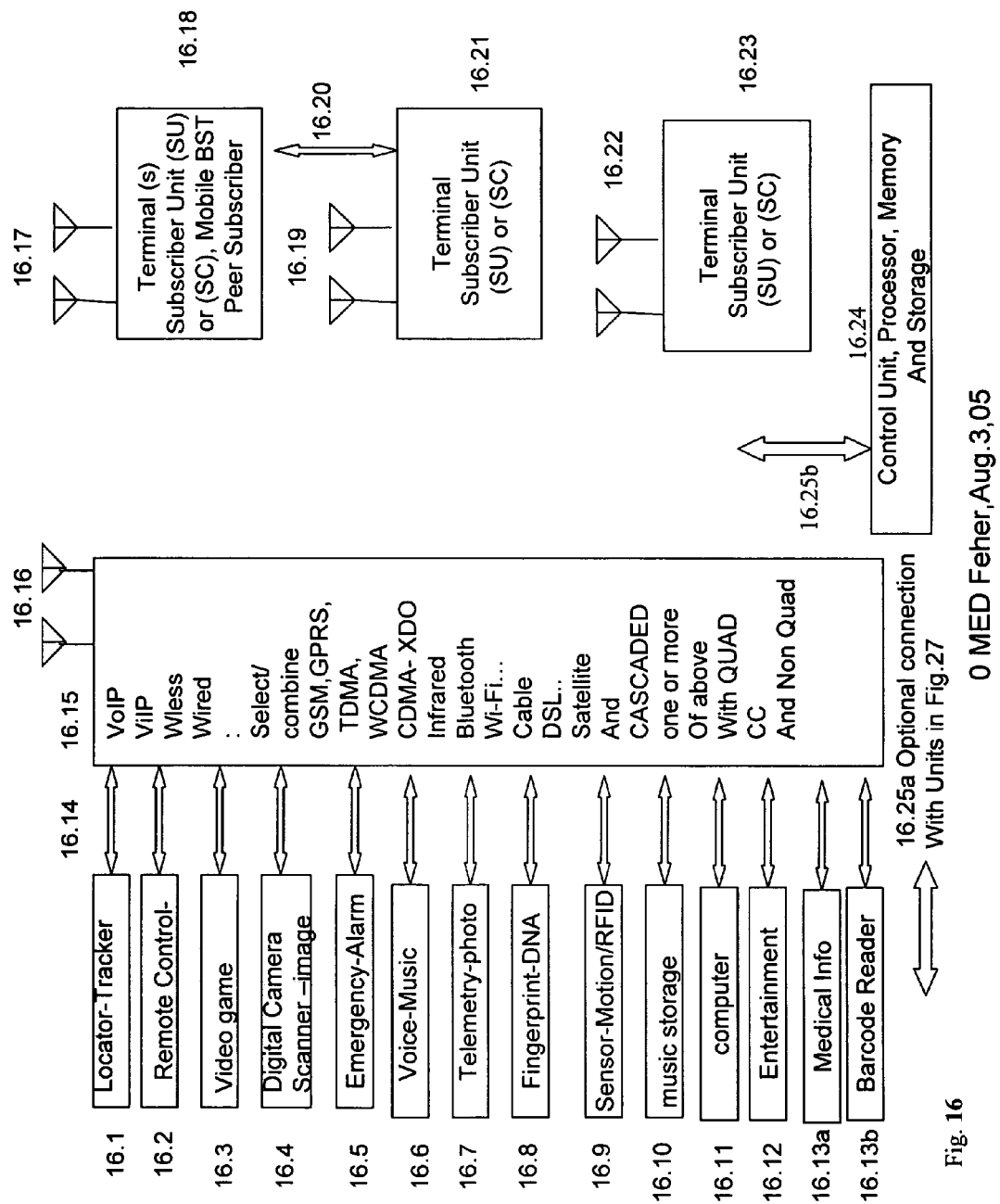
FIG. 16 is a multimode, multipurpose system embodiment for numerous applications, including signal processing and storage, medical diagnostics, broadcasting entertainment, educational and alarm system for seamless adaptive communications, emergency reporting, location finding and remote control embodiments.
Figure 27:
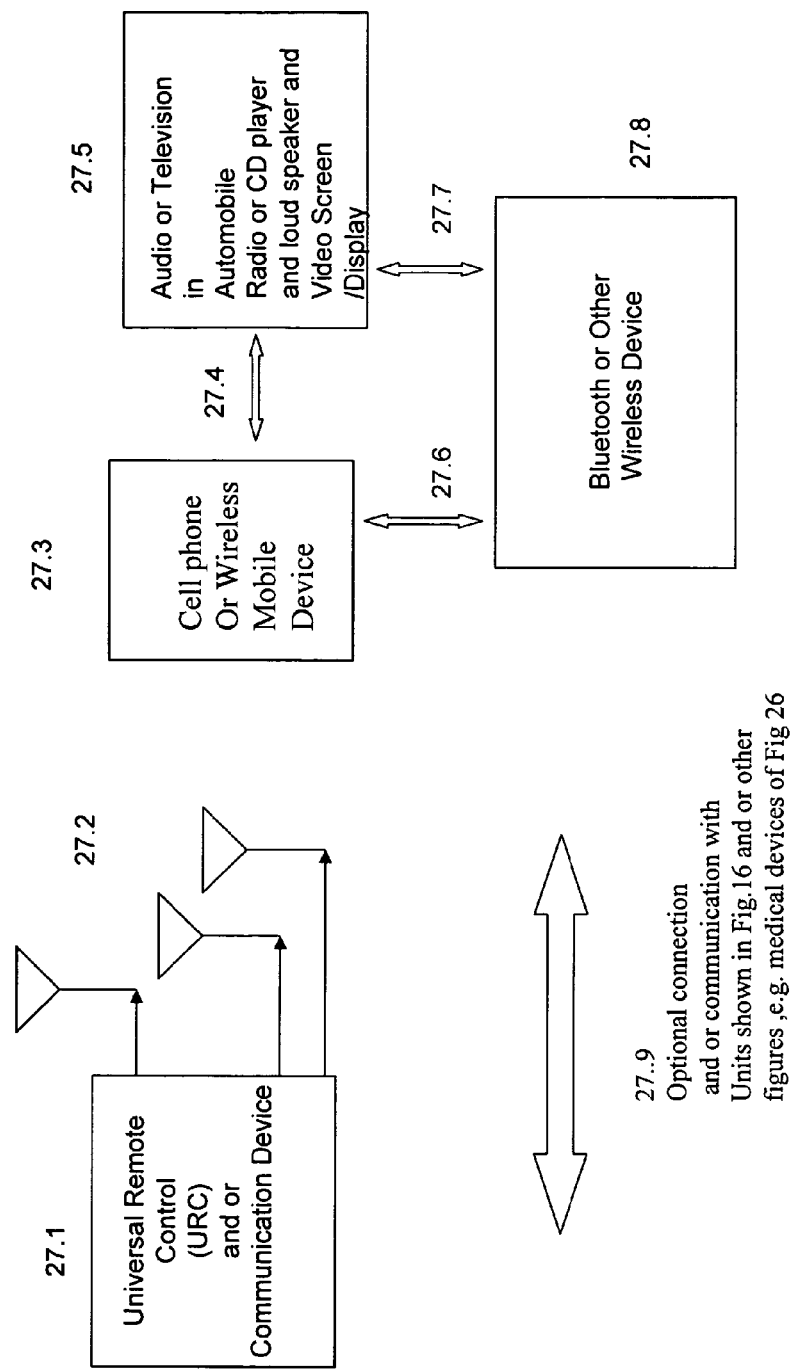
FIG. 27 depicts a Universal System including one or multiple Remote Control or Universal Remote Control (URC) devices, including wired or wireless devices.

FIG. 16 is a multimode, multipurpose system which incorporates embodiments for numerous applications, including but not limited to enhanced performance, increased coverage, higher speed information and data transfer wired and wireless communications seamless communications, communications over different operating systems and different standards, including American and internationally standardized systems, non-standardized systems, signal processing and storage, data manipulation, diagnostics, broadcasting entertainment, educational and alarm system for seamless adaptive communications, emergency reporting, location finding and remote control embodiments. Implementation and or selection of one or more of the system and network components, shown in FIG. 16, enable information storage, use of multimedia tools including voice, music, camera, high definition camera, real-time one-way, two-way or multi-way video and or and or voice calling, broadcasting and communications, still and moving image capture and editing. Direct access to launch browsers from the screen, by touching the screen or other direct access does not require push buttons. Addition of supplemental memory or removal of memory and or of other components is enabled by insertion or removal of components into one or more of the units shown in FIG. 16. Interconnection between cellular systems, Bluetooth, infrared, Wi-Fi with remote control devices, with cellular phone and automobile based or home based radio or television and or computer systems is enabled. One of FIG. 16 optional interconnections or communications with mobile devices in automobiles, other portable or mobile devices including motorcycles or other vehicles, e.g. tractors or trains or boats or ships or airplanes and or remote control systems is also shown in FIG. 27. Information and signal transmission and reception (communication and or broadcasting) are enabled between two or more than two users. Architectures and embodiments enable a single user to process, store and manipulate information and or to transmit it to others, or transfer to the user, computer, printer camera, facsimile or to other interface. The different units and or elements (components) of the system are optional and the system is operative in multiple embodiments without the use of certain elements (units) and or with an different interconnection between the units. In particular one or multiple elements 16.1 to 16.13 are connected and or selected through single or multiple leads 16.14 for connection to and from unit 16.15. Unit 16.1 contains a signal interface and or a signal processor for locator and or tracker device generated signals. Unit 16.2 contains a remote control signal interface or signal processor unit. Unit 16.3 contains a video game signal interface or signal processor unit. Unit 16.4 contains a digital camera and or scanner signal interface or signal processor unit. Unit 16.5 contains an emergency and or alarm signal interface or signal processor unit. Unit 16.6 contains voice, or telephony signal or music signal interface or signal processor unit or a combination of these interface units. Unit 16.7 contains interface circuits or signal processors for telemetry, telematics or photograph or scanned or facsimile signals. Unit 16.8 signal interface or signal processor elements for fingerprint identification and or fingerprint control and or touch screen control. Unit 16.9 contains signal interface or signal processor elements for sensor, transducer, detector (including motion detector, pressure detector, heat or smoke detector), Radio Frequency Identification and Detection (RFID) obtained signals. Unit 16.10 contains signal interface or signal processor unit to interface with stored analog or digital information, including stored music, stored video, stored images, stored scanned data information or other stored information. Unit 16.11 contains signal or data interface or signal or data processor device for connection and or processing of computer, including mobile computer, Personal Digital Assistant (PDA) and other digital or analog signals. Unit 16.12 contains signal interface or signal processor unit for connection, interface or coupling of music and or video, and or animated graphics and or sensor detected transformed signals or other stored and or retrieved information signals including signals containing educational materials. Unit 16.13 contains medical and or information signal interface or signal processor unit, including diagnostics, sensor, transducer obtained signals, motion detector or pressure detector or DNA generated or stored signals and or information. Unit 16.15 embodies one or more signal processors and communication devices for providing single or multimode communications, multidirectional (to and from) through single or multiple communications and or broadcast media to single or multiple terminals 16.18, 16.21 and 16.23 and or to one or multiple interface units 16.1 to 16.13. Terminal or Subscriber Units (SU), also designated as Subscribers (SC), are in some of the embodiments operated in a peer subscriber mode while in other configurations they are in a star, mesh or other network configuration, including optional adaptive network. An adaptive network is a network in which the connection between various elements of the network and the communication system format are changeable, that is, they are selectable or adaptable. The adaptive network configuration, interaction between various elements, selection of signals, selection and connection of one or of a multitude of signals and or interface units and or of one or more processors is controlled by the control unit, Unit 16.24. Control unit 16.24 provides and or receives one or multiple signals through single or multiple leads 16.25 from or to Unit 16.15, from or to the Subscriber Units (SU) and or from or to one more interface units 16.1 to 16.13. The signals from or to control unit 16.24 are chosen by manual control or voice control or other direct operator control, and or remotely and or electronically and or by software or firmware and or by hardware or firmware. Unit 16.15 is a single and or multimode, single and or multipurpose communication and signal processing and or data processing unit. Unit 16.15 contains one or more of the following interface points and or connections and or communication devices: Voice over Internet Protocol (VoIP), Video Internet Protocol (ViIP) or video over internet or video over intranet, wireless, mobile system elements including one or more processors, modulators demodulators (modems), transmitters receivers (TR) for TDMA, FDMA, GSM, GPRS EDGE, WCDMA, CDMA 1x, EV-DO, WLAN, WMAN, Wi-Fi, IEEE 802.xx, cable, DSL, satellite, cable, infrared (IR), Bluetooth, location finder, GPS, emergency alarm medical diagnostics or appliance communicator. These units operate in a "plug and play" configuration, that is, each unit can operate as a single unit or part of simultaneous operation in a network with several other units or in an adaptive network. The processors and or modulators contained in Unit 16.15 in certain implementations have non-quadrature (non-QUAD) architectures, such as in certain Frequency Modulated (FM) or Phase Modulated (PM) systems, e.g. FSK modulated or GFSK modulated systems, and Amplitude Modulated (AM) systems, including but not limited to implementations of polar modulated systems. In other embodiments quadrature modulation (QUAD mod) architectures with or without cross-correlation in the transmit baseband in-phase (I) and quadrature phase (Q) signals is implemented. In some other embodiments multiple modem architectures are implemented. In certain embodiments Unit 16.15 or one or more of interface Units 16.1 to 16.13 and or subscriber units (SU) 16.18, 16.21 and or 16.23 contain one or more of the following systems, components or signals: Multi-purpose System and Devices for Locator/Trackers-Position Determining Entity (PDE), Remote Control (RC), video, photograph, facsimile, emergency alarm, telephony signal, voice, music telemetry fingerprint DNA device activation sensor, motion sensor, body temperature sensor, Base Station Controller (BSC), Terminal or Subscriber Unit (SU) Base Station Transceiver Subsystem (BTS) devices. Each unit may contain processor, memory, communication port or interface, single or multiple modulator and or demodulator, automatic transmission alert of unauthorized and authorized fingerprint originated signals. Lead or leads 16.25a and 16.25b show optional connections with Units in FIG. 27 with one or more elements of FIG. 16 and or units in other figures.

Figure 26:
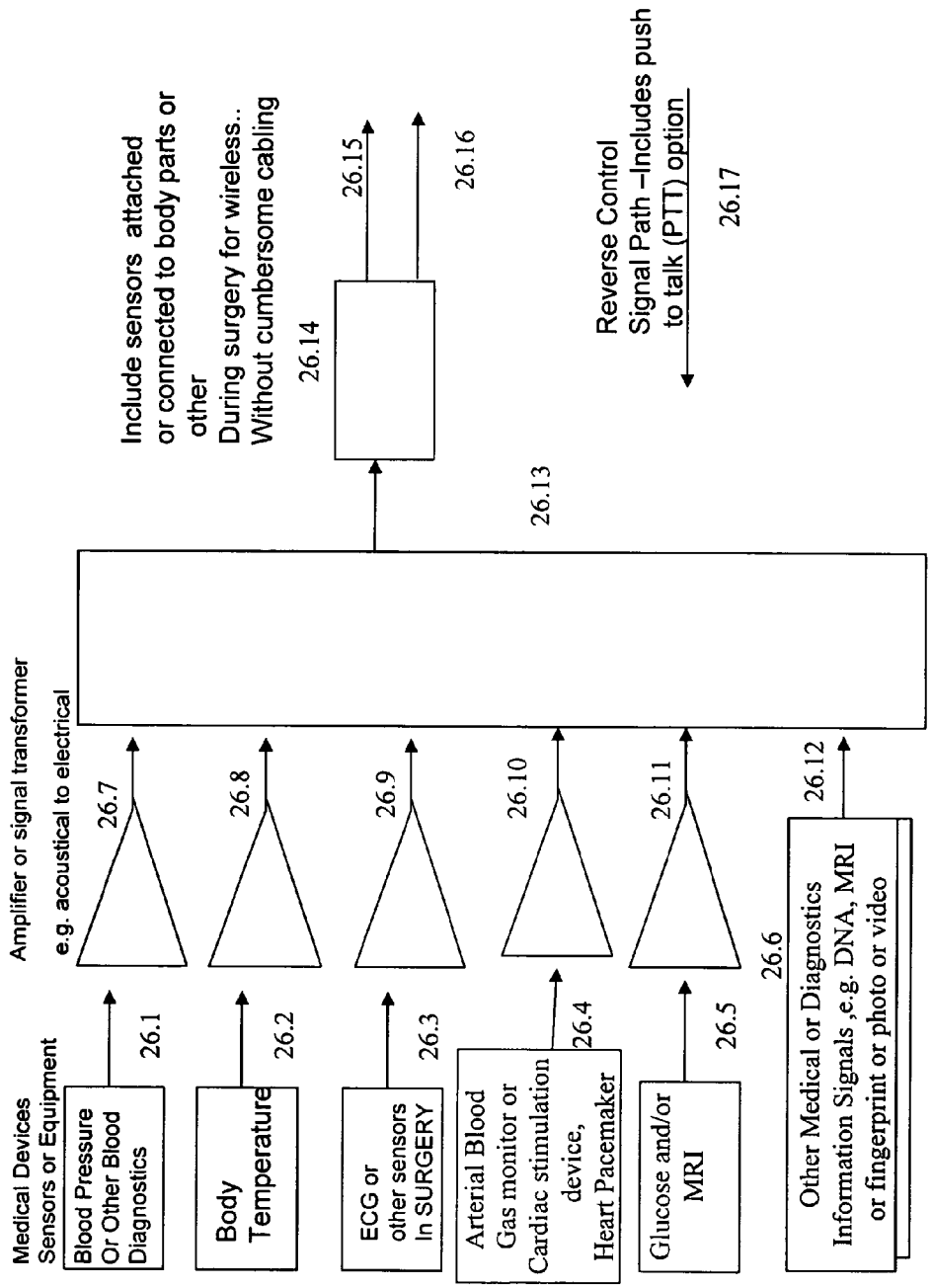
FIG. 26 is an information monitoring processing and communication system. This system in certain application includes a patient monitor and diagnostic system.
Figure 30:
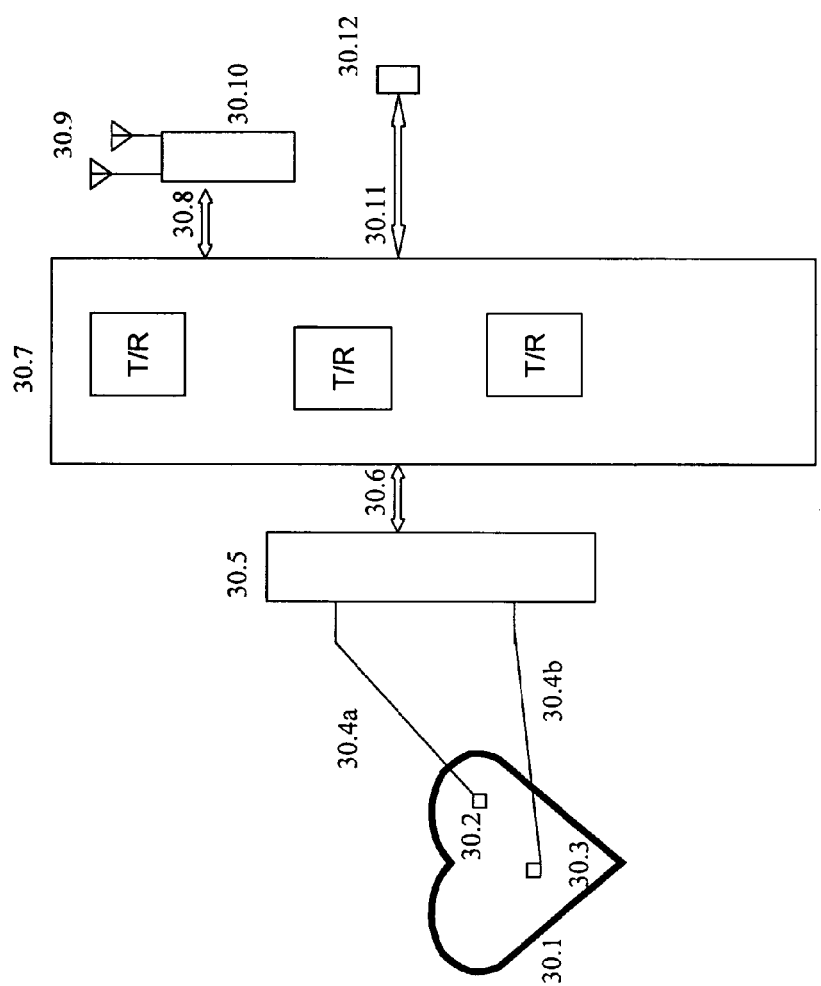
FIG. 30 represents an implantable cardiac stimulation device, a heart and a block diagram of a single-chamber and or a dual-chamber pacemaker with single or multiple wireless communications and control systems.

For user identification, user authentication, for medical information, emergency and alarm processing, for law enforcement, for financial and or other transactions, for signal transmission, reception and or control of one or more of Units 16.1 to 16.13, these units are in certain implementations are interconnected with and or comprise selected units of FIG. 26 and or of FIG. 27 and or of FIG. 30 and or of other figures of this disclosure. As an exemplary embodiment Unit 16.8 contains single and or multiple fingerprint sensors and conversion devices for conversion and or coding of the information contained in the fingerprint to signals suitable for multiuse signal processing, storage, authentication and/or identification of one or of a plurality of users and single and or multiple signal transmission. The signal transmitters transmit the signals provided by the single or multiple fingerprint sensors. The signal transmission of the fingerprint signals, depending on the setting of the transmitter is based on the authorized user and or by unauthorized user. Authorized and also unauthorized signal transmission is under the control of control Unit 16.24. Control Unit 16.24 contains in certain applications memory, processing and storage devices for storing the fingerprint information of the authorized and also of the unauthorized user and may provide control signals for transmission of the fingerprint information in addition to the dialed recipient to a third party, e.g. to a police department, to an emergency center or other law enforcement and or health care agency, or an individual or an alarm monitoring company, or the users alternate receiver device, which could include recording and/or storing the information on the same device in which the signal transmission originates. The telephone number(s) and or other information, e.g. e-mail address of the said third party may be preprogrammed by the authorized user and or remotely preprogrammed by law enforcement agencies. If unauthorized signal transmission (or authorized under force and or against the free will of the authorized user) is underway, the control unit 16.24 inserts "alarm" or "flag" signals into the transmitter path, alerting the single or multiple recipients, including the third party recipient that unauthorized and or emergency signals are transmitted and including signals for the recipient to store the unauthorized fingerprint and or the entire or part of the conversation and or communication. One of the sections of the fingerprint unit 16.8 and or the control and processor and memory unit 16.24, if requested by the control unit, based on reception and detection information of the received signal may store the received fingerprint information and or the received communications speech, picture, video or information in other forms. Authorizing may be performed locally or based upon a remote authorization signal. In case of unauthorized signal transmission, based on signal transmission of an unauthorized fingerprint user, Control Unit 16.24, in certain applications, directs the camera and or video recorder to take pictures and or video clips of the unauthorized transmitter's surroundings and add these signals to the intended recipient and to the third party receiver. In some embodiments, Unit 16.8 and or Unit 16.6 in conjunction with one or more other units 16.1 to 16.13 and or one or more Units 16.1 to 16.13, without the use of unit 16.8 are used for authorized user authentication and signal transmission storage, processing to third parties and to the users devices. In certain embodiments fingerprint sensor and converter of the fingerprint sensor provided information into signals which can be processed and stored and or analyzed, identified with a particular individual are included for single or multiple fingerprints in Unit 16.8 and or Unit 16.24. One or multiple fingerprint are used for single or multiple communication and or control and or location purposes. For example location of a mobile unit is enhanced by providing a fingerprint database having a multiplicity of transmitted fingerprints, each fingerprint in the fingerprint database having an associated unique location. Fingerprint information has multiuse benefits, including authentication of authorized use or of unauthorized use, locating the position of the device (mobile device and or stationary device), emergency request and or signal transmission and or storage to third parties, identification of the unauthorized user. Barcode reader, Unit 16.13b, within the structure of FIG. 16 and or in combination or connection with the structures of other figures of this disclosure, including but not limited to the structures of FIG. 27 has multiuse applications, including the above described use and applications.

FIG. 17a contains non-quadrature (non-QUAD) and quadrature modulation (Quad Mod or QUAD mod) multiple modulator exemplary embodiments, including polar modulator structures with and or without selection and or combining and connection of one or more of the modulated signals to one or a plurality of amplifiers and or one or more optional antennas, with and without cross-correlated quadrature modulation implementations for Bit Rate Agile (BRA) or Bit Rate Adaptive (BRA), Modulation Format Selectable (MFS) and radio frequency agile (RFA) system implementations having single or multitude of modulators, amplifiers and antennas of the current application are shown.

FIG. 17b Polar (non Quadrature) exemplary prior art modulator implementation block diagram is shown in this figure FIG. 17c Non-Quadrature (non-QUAD) exemplary prior art modulator architecture is shown in this figure.

FIG. 17a is described in more detail in this section. While, the prior art in general and Feher's U.S. patents, e.g. U.S. Pat. Nos. 5,491,457; 6,470,055; 6,198,777; 6,665,348; 6,757,334 and Ballantyne's U.S. Pat. No. 6,906,996, assigned to Qualcomm Inc., contain disclosures of multiple modulation wireless transmitters and communication systems, the prior art does not disclose the FIG. 17a disclosed architectures, structures and embodiments for system configurations and implementations of multiple modulator embodiments, including polar modulator structures with and or without selection and or combining and connection of one or more of the modulated signals to one or a plurality of amplifiers and or one or more optional antennas, with and without cross-correlated quadrature modulation implementations for BRA, MFS, and RFA system implementations having single or multitude of modulators, amplifiers and antennas with selectable single or multiple signal sources, disclosed in conjunction with FIG. 17a, FIG. 1, FIG. 2, FIG. 3, FIG. 16, FIG. 18, FIG. 27 and or other figures and relevant parts of the currently disclosed specifications and claims. In FIG. 17a Unit 17.1 is a single or multiple interface unit for connection of single or multiple signals to one or more signal and or data processor elements, shown as Unit 17.2. While four (4) processor units (boxes) are illustrated, in certain embodiments only one processor is used, while in other embodiments two or more processors are implemented. Single or multiple processor(s) provide processed signals to one or more than one (multiple or plurality) of modulator Unit(s) 17.3 for modulation. The processed signal or processed multiple signals are provided to single or multiple modulator Unit(s) 17.3. The signal connection or multiple connections between the processor(s) 17.2 and modulator(s) 17.3 is/are under the control of a control unit 17.9 and or under the control of an operator. One or more of the modulated signals is provided to a first optional modulated signal selector (switch) and or combiner and or splitter unit 17.4. One or more outputs of Unit 17.4 are connected to one or a plurality of amplifiers 17.5. The amplified signal or signals are connected to the second optional selector, combiner or splitter unit 17.6. The outputs of Unit 17.6 are provided to an optional signal interface unit 17.7 and afterwards to one or more optional antennas, Unit 17.8. There is a variety quadrature modulator embodiments disclosed in the prior art. In FIG. 11b of the current application an exemplary prior art quadrature modulation implementation is highlighted. One or multiple quadrature modulator (QUAD mod) implementations and embodiments are used in the embodiments of the quadrature modulators, shown in FIG. 17. In certain embodiments of FIG. 17 one or more non-quadrature (non-QUAD) modulators are implemented, in addition to QUAD modulators and or instead of QUAD modulators. Some of the non-quadrature modulation structures are known in the prior art as polar modulation, while other non-QUAD modulators are prior art Frequency Modulators (FM), Frequency Shift Keying (FSK), Gaussian Frequency Shift Keying (GFSK), Amplitude Modulator (AM) systems and devices. FIG. 17b and FIG. 17c. show two prior art non-QUAD modulation architectures.

FIG. 17b is based on Lindoff et al. U.S. Pat. No. 6,101,224 and Black et al U.S. Pat. No. 5,430,416, assigned to Motorola. The illustrated non-QUAD modulation technique is also known as polar modulation, since it is based on a polar representation of the baseband signals. In this non-Quad modulator polar components i.e., amplitude (r) and phase (p) components are used, instead of in-phase (I) and quadrature-phase (Q) components used in quad modulation techniques. In this exemplary prior art modulator, the source signal (or information signal) to be transmitted is present on connection 17.10. Signal processor 17.11 generates a signal amplitude component and a signal phase component. These signal components are provided to a Digital to Analog (D/A) converter and to a Phase Modulator (PM) respectively. The phase component modulates the carrier signal in a phase modulator 17.13, resulting in a phase modulation with constant envelope. The amplitude component is converted to an analog signal in a D/A-converter and then fed through a regulator (Reg) 17.14 which adjusts the current or voltage of the signal controlling the power of a power amplifier (PA) 17.15, based on the signal and the output D/A converted signal 17.12. The regulated analog signal modulates the phase modulated carrier signal in the output power amplifier 17.15 by controlling the power of the power amplifier. The resulting amplified signal is then provided for transmission.

FIG. 17c shows an exemplary other prior art Non-QUAD modulator. In this implementation the source signal, present on lead 17.16 is provided to a Phase Modulator (PM) or Frequency Modulator (FM), Unit 17.17. The PM and/or FM modulated signal is provided to a subsequent Amplitude Modulator (AM) and the AM modulated signal is provided to the transmission medium interface on lead 17.19.

Figure 18:
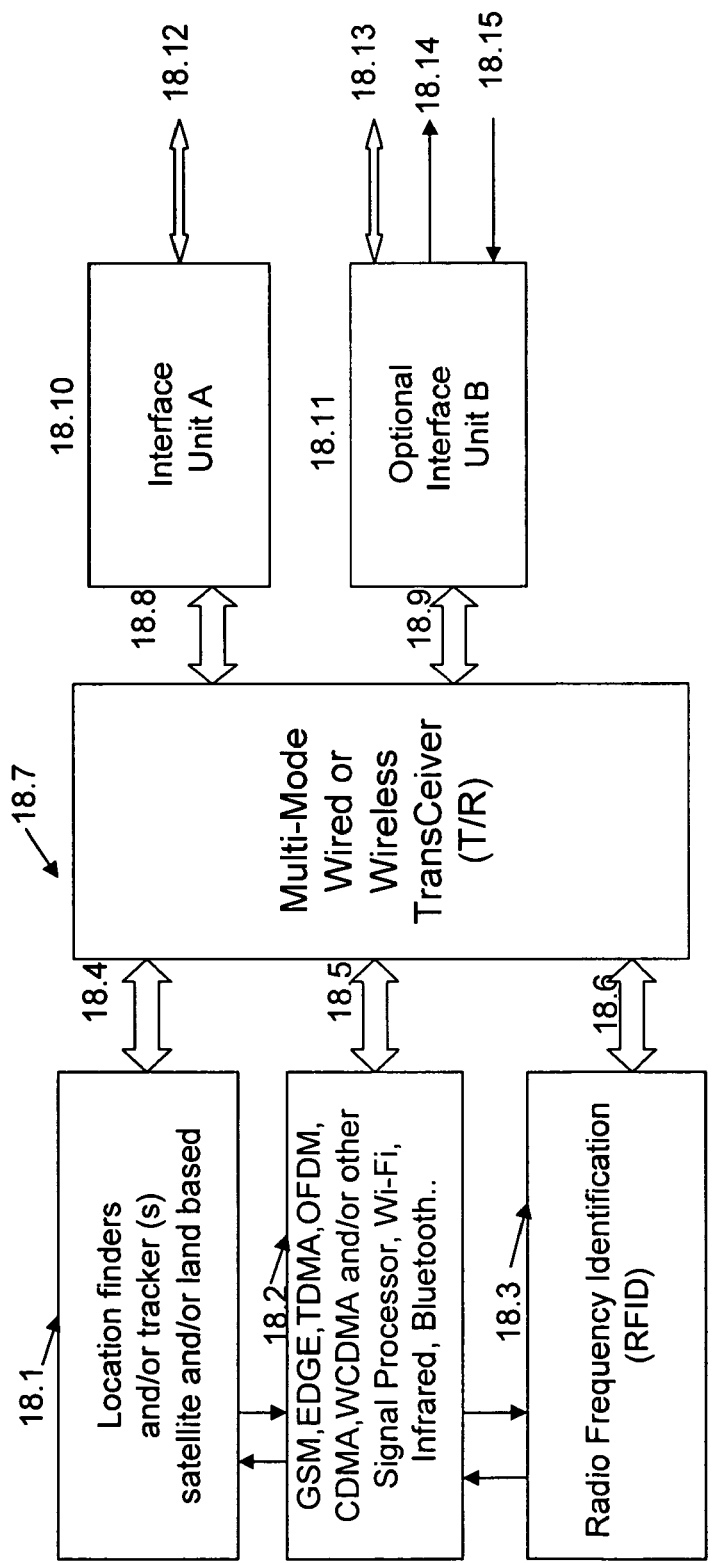
FIG. 18 represents multi-mode location receiver connections to multi-mode or to single mode wireless transmitters.

FIG. 18 is a location (position) finder, communication and or broadcast and Radio Frequency Identification Detection (RFID) single and or multimode system. Unit 18.1 contains one or a plurality of location finder (also designated as position finder) and or tracker interface units or systems, which are satellite based, or land based or based on or in water and or air based. On water based systems include ships, boats, vessels, buoys, swimmers, floating devices. In water systems include submarines, divers, fish, sharks, creatures and or their attached devices. Air based systems are in aircraft such as airplanes, helicopters, Unmanned Vehicles (UV) or in balloons or in birds or in other objects or air based items, including but not limited to rockets, missiles, space shuttles or other items. In certain embodiments Unit 18.1 includes optional communication and or control devices, such as Remote Control (RC) devices. One or multiple communication and or control devices are contained in one or more units shown in FIG. 18. In one embodiment all Units 18.1 to 18.15 include interface and or processor circuits for single or multiple location finders, single or multiple communication and or single or multiple RFID and or single or multiple control. Units 18.2 contains one or more interface and or processing and or modulation demodulation units for GSM, GPRS, EDGE, TDMA, OFDMA, CDMA, WCDMA, Wi-Fi, Bluetooth, Infrared (IR), CDMA, WCDMA, IEEE 802.xx or other communication systems. Units 18.3 contain single or multimode wireless or wired transceivers and interconnection between a multitude of units, shown in FIG. 18. Optional interface units 18.10 and 18.11 provide signals for further processing to one or more interface connections 18.12, 18.13, 18.14 and or 18.15

Figure 19:
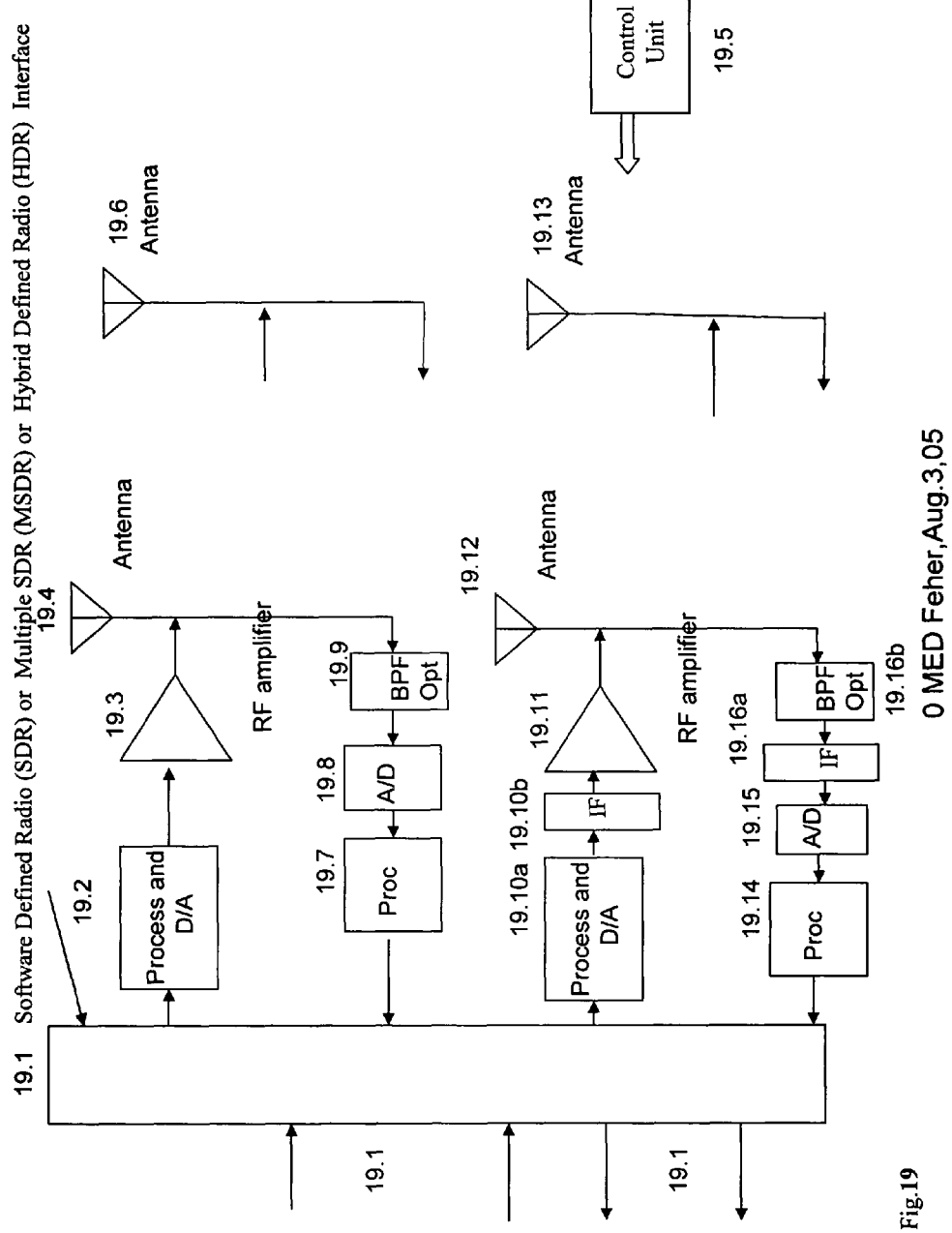
FIG. 19 is a Software Defined Radio (SDR), Multiple SDR (MSDR) and Hybrid Defined Radio (HDR) transmitter and receiver embodiment, with single or multiple processors, single and or multiple RF amplifiers and antennas and single or multiple SDR and or non-SDR implementation architectures.

FIG. 19 is a Software Defined Radio (SDR), Multiple SDR (MSDR) and Hybrid Defined Radio (HDR) transmitter and receiver embodiment, with single or multiple processors, single and or multiple RF amplifiers and antennas and single or multiple SDR and or non-SDR implementation architectures. While SDR implementations and embodiments have been disclosed in the prior art, including in exemplary cited references: book by Tuttlebee, W.: "Software Defined Radio: Baseband Technology for 3G Handsets and Basestations", John Wiley & Sons, Ltd., Chichester, West Sussex, England, Copyright 2004, ISBN 0-470-86770-1.; article by Hickling, R. M.: "New technology facilitates true software defined radio" RF Design Magazine April 2005, available from www.rfdesign.com (5 pages), and numerous patents, such as exemplary cited patents, including Kohno et al.: U.S. Pat. No. 6,823,181, "Universal platform for software defined radio", assigned to Sony Corporation, Tokyo, Ballantyne's U.S. Pat. No. 6,906,996 "Multiple Modulation Wireless Transmitter", assigned to Qualcomm, Inc., the prior art does not disclose nor anticipate the implementations, embodiments and architectures of Software Defined Radio (SDR) and or Multiple SDR (MSDR) and or Hybrid Defined Radio (HDR) transmitter and receiver embodiments, with single or multiple processors, single and or multiple RF amplifiers and antennas and single or multiple SDR implementation architectures described in the specifications related to FIG. 19 and in other sections of this application. An exemplary prior art SDR contains an interface unit, such as Unit 19.1, a processor and a Digital to Analog (D/A) converter, Unit 19.2, an RF subsystem consisting of transmit RF amplifier, Unit 19.3, signal connection to and from transmit and or receive antenna, Unit 19.4, in the received signal path an optional RF Band-Pass-Filter (BPF), Unit 19.9, an Analog to Digital Converter (A/D), Unit 19.8, and a signal processor, Unit 19.7. The new Software Defined Radio (SDR) system, disclosed in this application contains one or more SDR connected to one or more RF transmit amplifiers and connected to one or more transmit antennas and one or more receive antennas. With multiple antennas transmit and or receive diversity systems are implemented. If multiple SDR is used then the system is designated as a Multiple SDR (MSDR). The SDR receiver part consists of one or more SDR receivers and or one or more conventional (non SDR) receiver systems. In some of the embodiments one or more SDR transmitters and or SDR receivers are used in conjunction with one or more non-S DR transmitter or receiver implementations. Non-SDR systems are radio systems which are implemented by firmware and hardware components and may include software applications or software processors, such as Digital Signal Processors. Systems which incorporate SDR components as well as non-SDR components (e.g. conventional prior art radio systems having mixed software, firmware and or hardware at baseband and or IF and or at RF) are designated as Hybrid Defined Radio (HDR) systems. Units 19.4 and 19.12 are transmit and or receive antennas. Additional antennas 19.6 and 19.13 transmit and or receive signals to the SDR and or MSDR and or HDR units. In this figure, all units 19.1 to 19.13 are single units in some embodiments, while all units 19.1 to 19.13 are single or multiple units in other embodiments. Unit 19.5 is a control unit for control of one or more units. In certain implementations selected units in FIG. 19 are BRA and MFS units, while in other embodiments single and or multiple units are used for transmission of the same bit rate and signal having the same specified modulation format. Control unit 19.5 generates and provides control signals to various transmitters and receivers and antennas for the selection and reception of specified signals.

Figure 20:
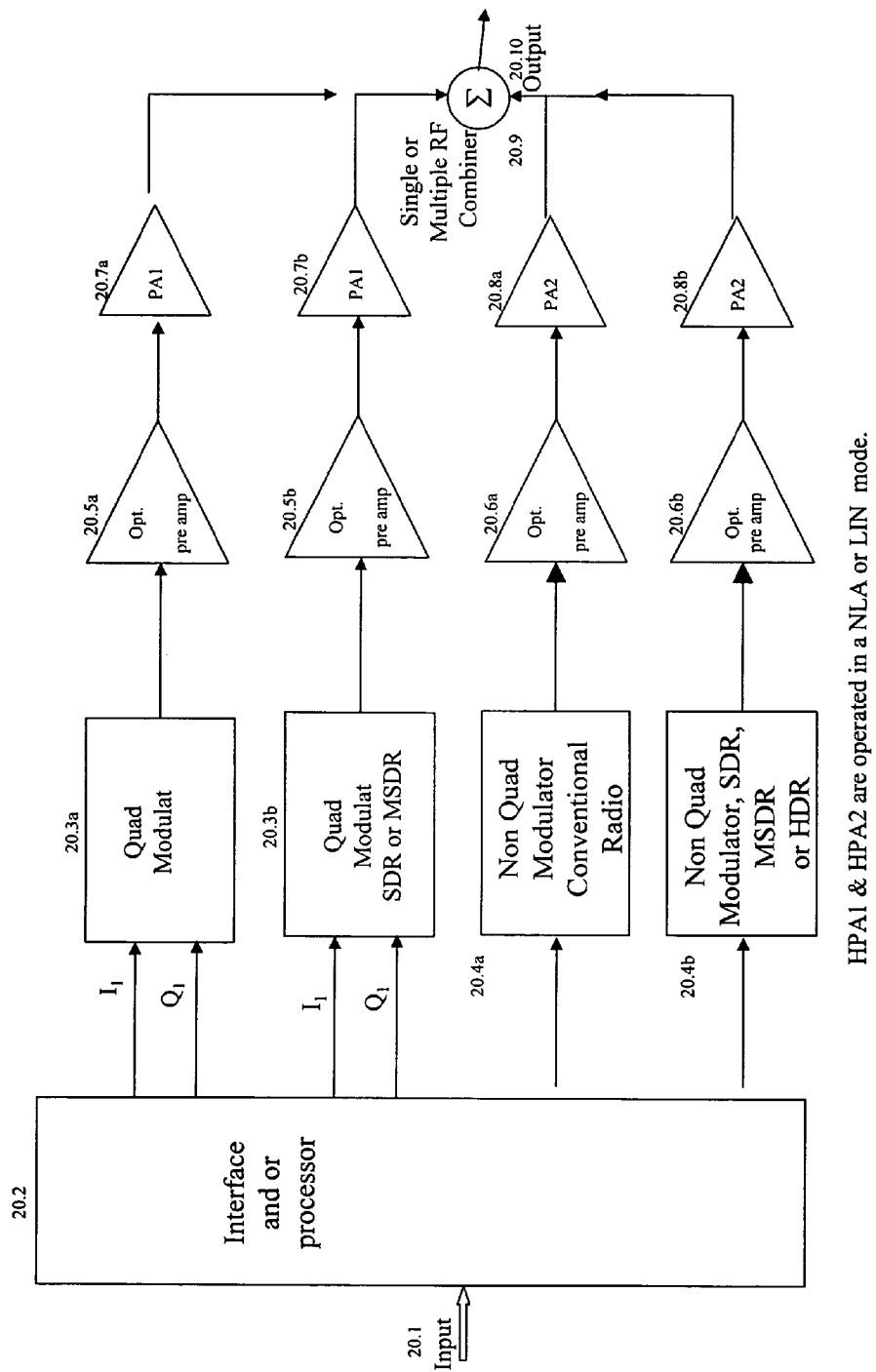
FIG. 20 shows interface and or processor units, set of modulators, amplifiers, selection devices and or combiner devices which provide RF signals to the transmission medium.

FIG. 20 contains an interface unit or multiple interface units, set of modulators, amplifiers, selection devices and or combiner devices which provide RF signals to the transmission medium. Single or multiple interface units, single or multiple modulation, single or multiple amplification, BRA and MFS structures and implementations are included. In this embodiment input lead 20.1 or multiple input leads 20.1 provide an input signal or multiple input signals to single or multiple interface and or processor unit 20.2. At the output of Unit 20.2 on one or multiple signal leads quadrature or non-quadrature signals are provided. In-phase (I) and quadrature-phase (Q) baseband signals are provided to Unit 20.3*a*. Unit 20.3*a* is a quadrature modulator which provides in some embodiments cross-correlated I and Q (designated also as I/Q) baseband signals, while in other embodiments there is no cross-correlation provided for the I/Q baseband signals, which are quadrature modulated (QM) in Unit 20.3*a*. Unit 20.3*b* contains one or more quadrature modulators (QM). The implementation of one or more of the QM, contained in unit 20.3*b* is in certain embodiments a SDR implementation structure, in some other embodiments it is a MSDR structure, while in certain other embodiments it is a HDR and or it is an other conventional prior art QM structure. Units 20.4*a* and 20.4*b* are non quadrature modulators. One or more of these modulators are embodied by conventional prior art non-quadrature modulators, such as FM, PM or AM or BPSK or FSK or other non SDR architectures, while in certain other embodiments the non-quadrature modulators are implemented by SDR and or by MSDR and or by HDR architectures and or by digital or analog polar modulation structures. One or more of the modulators 20.3*a*, 20.3*b*, 20.4*a* and or 20.4*b* in certain implementations operates at an Intermediate Frequency (IF) and contains an up-converter unit (frequency translation device) to the desired Radio Frequency (RF). One or more of the modulators 20.3*a*, 20.3*b*, 20.4*a* and or 20.4*b* in certain implementations are Bit Rate Agile or Bit Rate Adaptable (BRA) and or Modulation Format Selectable (MFS) and or Modulation Embodiment Selectable (MES) systems. In certain designs and or embodiments the same modulation format and same bit rate is used, however the modulation embodiment is different. For example, in an application a GMSK modulated system uses a Quadrature Modulation (QM) structure for low transmit power applications, while for a high transmit power application it uses a non-quadrature modulation (NQM), e.g. polar implementation structure. Thus, in this example the same GMSK modulation format, having the same bit rate (or a different bit rate) is switched (or selected) to be transmitted instead in the QM embodiment in a NQM embodiment. One or more of the modulators 20.3*a*, 20.3*b*, 20.4*a* and or 20.4*b* in certain implementations are IF and or RF agile, that is IF and or RF adaptable modulators, having selectable and or adaptable center frequency (and or center frequencies) of the modulated signal(s), which is (are) most suitable for the desired transmission frequency band. One or more of the modulators provides signals to one or more optional preamplifiers 20.5*a*, 20.5*b*, 20.6*a* and or 20.6*b* and or to one or more optional Power Amplifiers (PA) 20.7*a*, 20.7*b*, 20.8*a* and or 20.8*b*.

The preamplifiers operate in a linearized or linearly amplified (LINA) mode or in a Non-Linearly Amplified (NLA) mode. One or more of the amplified signals are provided to the output connector 20.10 through optional single or multiple combiner unit 20.9.

Figure 21:
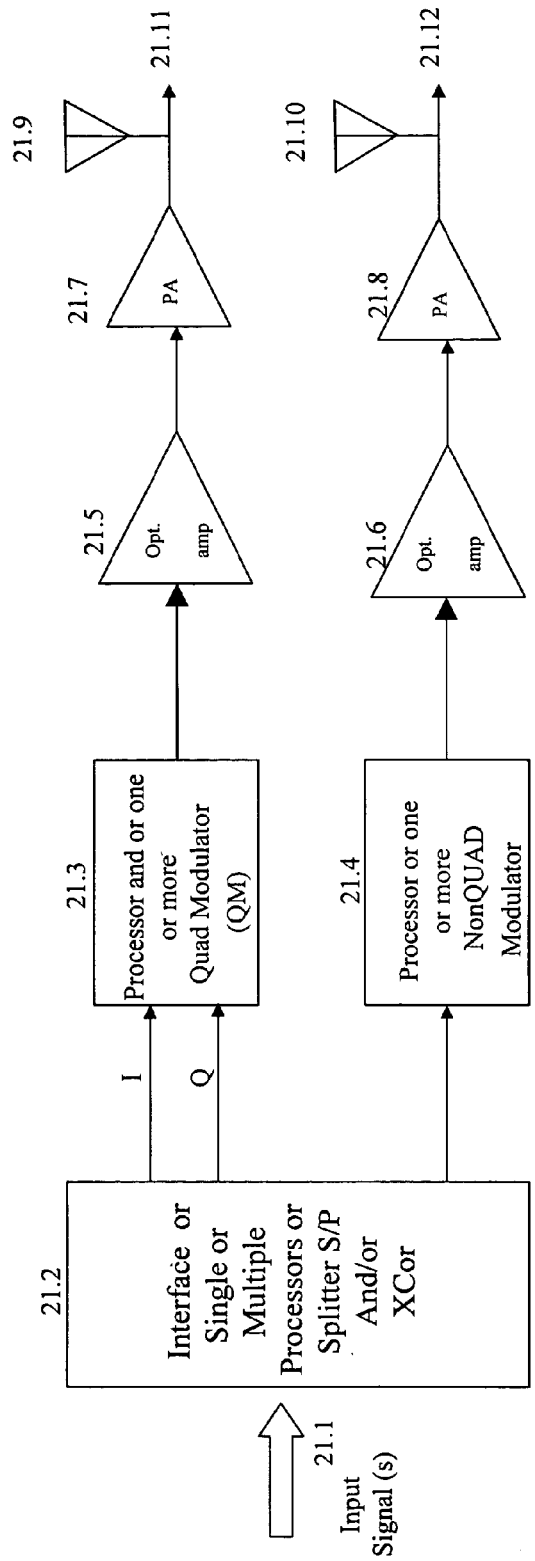
FIG. 21 is an embodiment of a single or multiple transmitter architecture using single or multiple transmitters; the multiple transmitter implementations are also designated as a diversity transmitter.

FIG. 21 is an embodiment of a single or multiple transmitter architecture using single or multiple transmitters; the multiple transmitter implementations are also designated as a diversity transmitter. This figure contains some of the elements, disclosed in prior art cited reference Feher's U.S. Pat. No. 6,665,348. On input lead 21.1 there is a single signal or there are multiple signals provided to Unit 21.2. Unit 21.2 contains one or more interface circuits and or one or more processors and or one or more splitters and or one or more Serial to Parallel (S/P) conversion circuits and or one or more signal switch (selector) circuits, one or more cross-correlator (XCor) circuits and one or more optional in-phase (I) and Quadrature-Phase (Q) signal processors and or generators. Unit 21.3 receives one or more I and Q signals from Unit 21.2. In Unit 21.3 one or more signal processors and one or more optional Quadrature Modulators (QM) are implemented. The output processed and or modulated signals are provided to optional units 21.5, 21.7 and 21.9 and or 21.11 for optional signal amplification by one or more linear amplifiers (LIN) or one or more Non-Linear Amplifiers (NLA) and or one or more Power Amplifiers (PA) and provided to one or more antenna 21.9 and or one or more interface connections 21.12 to interface with one or more communication systems. Unit 21.4 receives one or more signals from Unit 21.2. In Unit 21.4 there are one or more interface points (or interface connections), processors and or one or more non Quadrature modulators (Non Quad or NonQUAD or NQM) modulators. Units 21.5, 21.6, 21.7, 21.8, 21.10 and 21.12 are optional amplifiers, antennas and or interface points.

Figure 22:
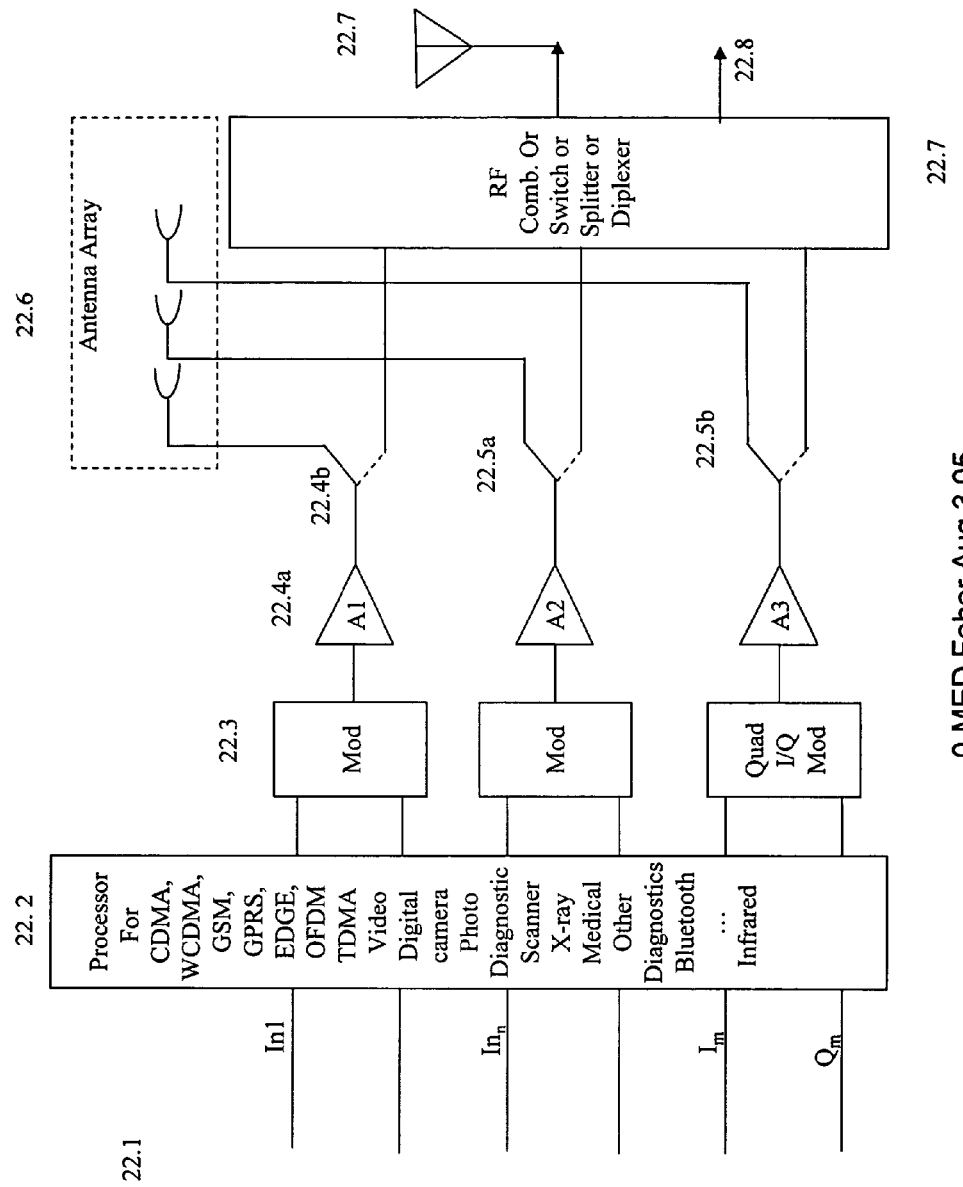
FIG. 22 shows a Multiple Input Multiple Output (MIMO) system.

FIG. 22 is a Multiple Input Multiple Output (MIMO) system. On single or multiple input lead 22.1 one or more input signals are provided to single or multiple interface and or single or multiple processor unit 22.2. The non-quadrature input signals are designated as $In_1$ to $In_n$, the n subscript indicating that there are n non-quadrature input signals, where n is an integer n=1, 2, 3 . . . , while the quadrature inputs are designated as $I_m$ and $Q_m$, the m subscript indicating that there are m input quadrature signals, where m is an integer m=1, 2, 3 . . . In unit 22.3 a single or multiple interface unit and a single or multiple processor unit is embodied. The processor(s) process baseband signals into suitable baseband formats for subsequent single or plurality of signal selections for subsequent modulation of CDMA, WCDMA, EvDo, GSM, GPRS, EDGE, OFDM, TDMA or Video Digital, or camera signals, photo camera originated signals, diagnostics, scanner X-ray, or medical device signals, Bluetooth originated signals or, infrared originated signals and selection or connection of one or more of these signals to one or more quadrature or non-quadrature modulators, implemented in Unit 22.3. One or multiple modulators, implemented in Unit 22.3 receive one or more of these signals and modulate them in single or multiple non-quadrature or quadrature modulator embodiments. One or multiple optional amplifiers, embodied in optional unit 22.4a are connected by optional single or multiple switching or splitting elements 22.4b, 22.5a or 22.5b to one or more antennas, shown as an antenna array, Unit 22.6 and or to an optional RF unit 22.7. Unit 22.7 contains an RF interface point and or one or more RF switching, combining, duplexer or diplexer and or splitter units. RF unit 22.7 is connected to output interface point 22.8 and/or to one or more antennas embodied in unit 22.7. Multiple I and Q inputs (I/Q inputs) with multiple non-quadrature inputs, connected to one or multiple processors, modulators, optional amplifiers RF combiners or RF switching elements and antennas, as embodied in one or more of the configurations and connection of selected elements of FIG. 22 distinguishes the embodiments from prior art.

Figure 23:
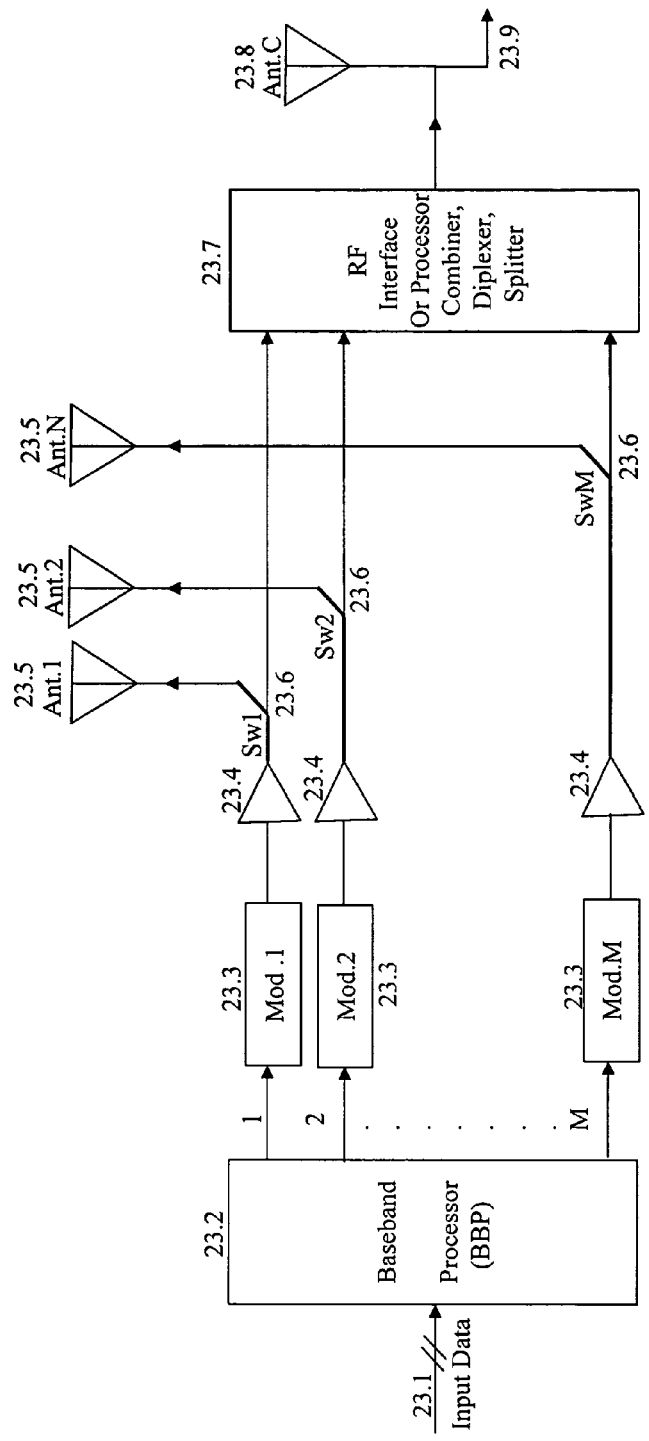
FIG. 23 is a Single Input Multiple Output (SIMO), Multiple Input Multiple Output (MIMO), and or Multiple Input Single Output (MISO) embodiment having one or multiple RF interface points and or one or multitude of antennas.

FIG. 23 is a Single Input Multiple Output (SIMO), Multiple Input Multiple Output (MIMO), and or Multiple Input Single Output (MISO) embodiment having one or multiple RF interface points and or one or multitude of antennas. The configuration with multiple antennas is also known as a system with antenna arrays and or a diversity system. On input lead or multiple input leads 23.1 one or multiple signals are connected to single or multiple interface Unit 23.2. One or more than one optional baseband processors (BBP) are contained in some of the embodiments of Unit 23.2. One or plurality of signals is present on connections (or leads) designated as 1, 2, . . . M. One or more of these signals are connected to one or more modulators, contained in Unit 23.3. These modulators designated as Mod.1, Mod.2 . . . and Mod.M modulate one or more input signals and provide the modulated signals to one or more optional amplifiers, contained in Unit 23.4 Through optional switching elements 23.6, designated as Sw1, Sw2 . . . Sw.M one or more modulated signals are provided to one or more optional antennas 23.5 (Ant.1, Ant.2 . . . Ant.N) and or RF Unit 23.7. The number of embodied modulators in certain implementations is the same as the number of switches and antennas in Unit 23.5, while in other embodiments it is different. In Unit 23.7 there is an RF interface and optional RF combiner, splitter or switch unit for providing one or more RF signals to the subsequent single or multiple RF interface unit 23.9 and or optional single or multiple antenna 23.8.

Figure 24:
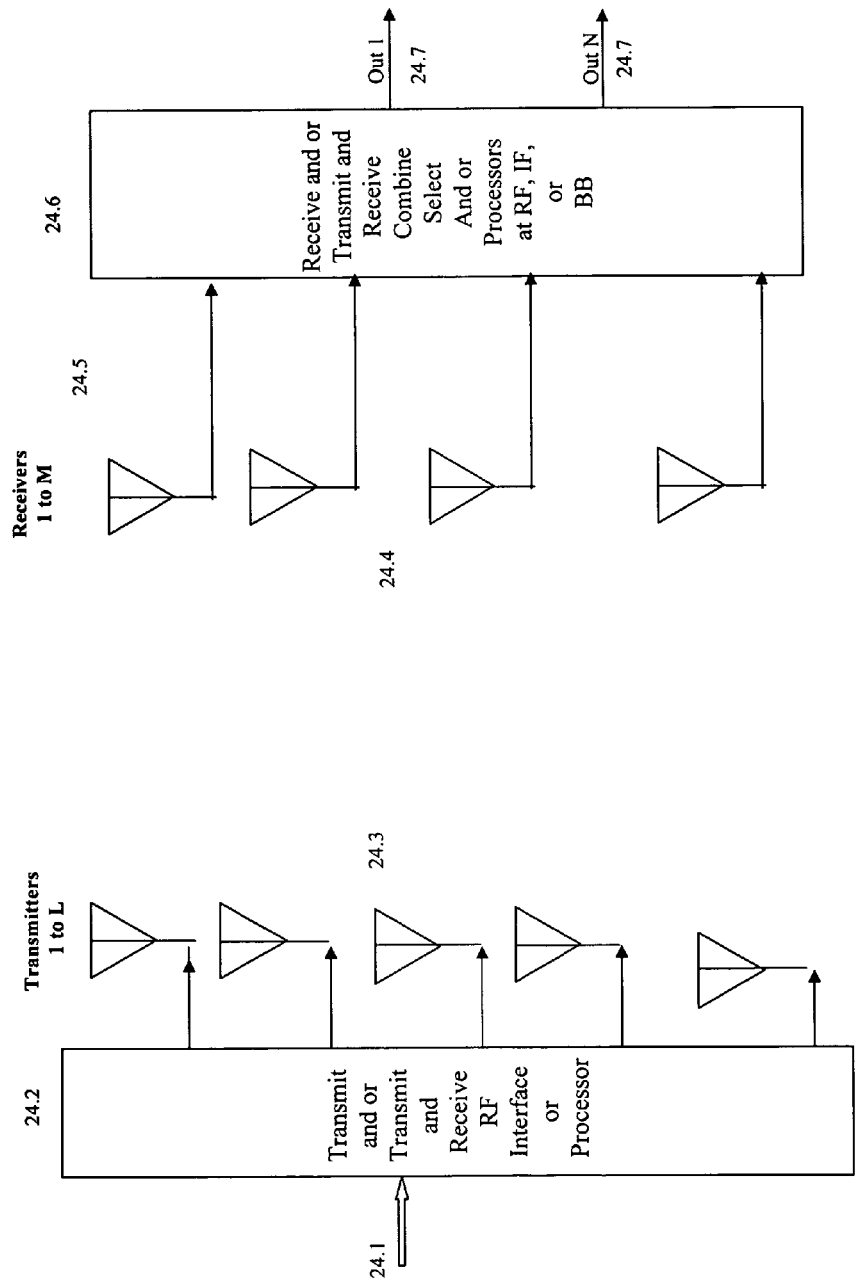
FIG. 24 represents an antenna array implementing Multiple Input Multiple Output (MIMO) and or Single Input Multiple Output (SIMO) and or Multiple Input Single Output (MISO) communication, position finding and broadcasting transmission-reception system, including transmit antenna diversity and receive antenna diversity systems.

FIG. 24 is an antenna array implementing Multiple Input Multiple Output (MIMO) and or Single Input Multiple Output (SIMO) and or Multiple Input Single Output (MISO) communication, position finding and broadcasting transmission-reception system, including transmit antenna diversity and receive antenna diversity systems. While the system contains elements of one or more Feher's prior art references, e.g. Feher's U.S. Pat. No. 6,665,348, the configurations, interconnections and operation with other system elements disclosed in this application and shown in previous or subsequent figures of this disclosure are new. On single or multiple input leads 24.1 one or more modulated RF signals are received and connected to optional single or multiple RF interface and or RF processor 24.2. Unit 24.2 in certain embodiments includes transmit processors, while in other embodiments it includes transmit and receive processors. The received RF modulated signals on connection 24.1 are provided by one or more disclosed embodiments in the description of previous or subsequent figures of this disclosure. One or multiple transmit antennas contained in Unit 24.3 are connected to one or more RF modulated signals. Single or multiple receivers have a single or multiple antennas, embodied in unit 24.4. In certain embodiments transmit and receive components, including connections/leads, interface units, processors and antennas are the same components, or are at the same location, while in other implementations the transmit and receive components are distinct physical units, while in some alternate implementations certain transmit and receive components are contained in the same physical units, while certain other transmit and receive components are distinct units. On receive single or multiple connections 24.5 one or more signals from the receiver antennas are connected to optional receive RF interface unit 24.6 which contains optional combiner, selector or switch or other RF signal processors and or RF processors combined with frequency down conversion components, IF processors and baseband processors. Single or multiple output signals are provided on output connection lead 24.7 Out 1 to Out N.

Figure 25:
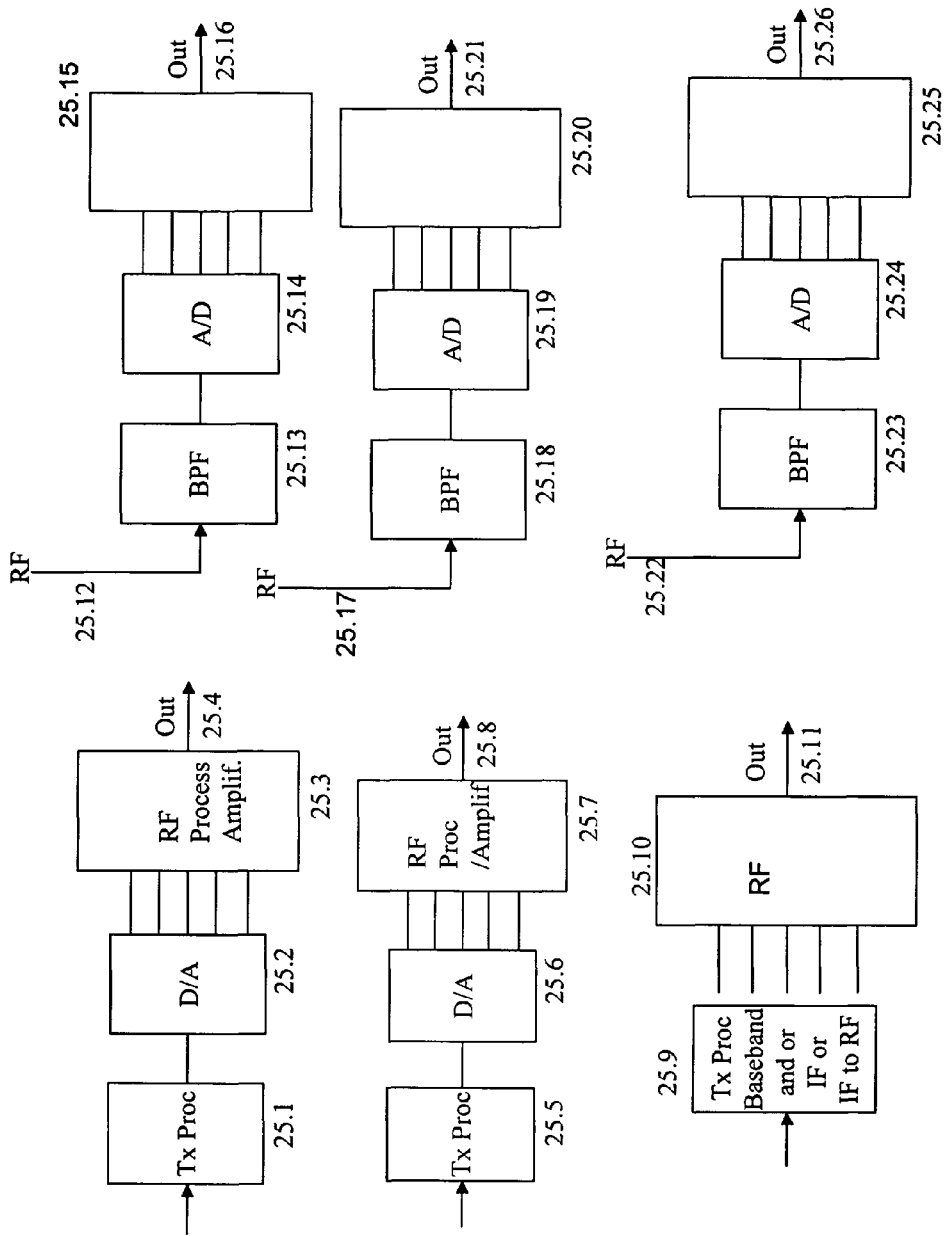
FIG. 25 shows Software Defined Radio (SDR) and Hybrid Defined Radio (HDR) systems for Multiple Input Multiple Output (MIMO) and or Single Input Multiple Output (SIMO) and or Multiple Input Single Output (MISO), including diversity systems.

FIG. 25 Software Defined Radio (SDR) and Hybrid Defined Radio (HDR) systems for Multiple Input Multiple Output (MIMO) and or Single Input Multiple Output (SIMO) and or Multiple Input Single Output (MISO) communication, position finding and or broadcasting transmission-reception systems, including diversity systems are implemented in this figure. On single or multiple input connections signals are provided to one or more of transmit (Tx) interface and or transmit processor units 25.1, 25.5 and 25.9. These units are parts of SDR and or HDR system embodiments. One or more of units 25.1, 25.5 and or 25.9 receive signals from one or multiple sources, for example from a location finder and or tracker source, a communications device, a remote controller, multiple remote controllers, an RFID device, a patient monitoring device, a video source, a video broadcasting source, video conferencing source, a source providing video clips, cellevision (cellular television), mobile vision, WiFi, WiMax an alarm monitor, a camera, a source providing data for credit card verification and or credit card transactions, a source providing bank transactions, a source providing electronic commerce signals /data and or other sources. In the SDR, units 25.1 and 25.5 process signals and provide them to Digital to Analog (D/A) converters (DAC) 25.2 and 25.6. In the HDR, one or more signals and or D/A converted signals are provided to one or multiple RF processing units 25.3 and/or 25.7 or 25.10. The RF processed and or RF amplified outputs, of the SDR units, are provided to single or multiple transmit interface units or single or multiple transmit antennas, designated as Out 25.4 and 25.8. Element 25.9 receives single or multiple input signals for baseband and or Intermediate Frequency (IF) and or IF and or IF and RF or merely RF transmission processing of the system. The RF signals are further processed in optional unit 25.10 and provided to single or multiple transmit interface units or single or multiple transmit antennas, designated as Out 25.11. Units 25.9, 25.10 and 25.11 are part of a single or multiple conventional radio transmitter implementation, in other words these units are not part of a SDR. Since Units 25.1 to 25.8 are part of single or multiple SDR transmitters, and Units 25.9 to 25.11 of a conventional Radio Transmitter (Tx), the combinations of SDR and conventional radio transmitters are designated as Hybrid Defined Radio (HDR) systems. One or multiple input signals are connected to one or more SDR and or one or more conventional radio systems parts of the HDR. In the receiver section of the HDR on leads 25.12, 25.17 and 25.22 single or multiple RF signals are received from single or multiple antennas. Units 25.13, 25.18 and 25.23 are single or multiple embodiments of Band Pass Filters (BPF), Units 25.14, 25.19 and 25.24 are single or multiple embodiments of Analog to Digital (A/D) Converters (ADC). Units 25.16, 25.21 and 25.26 are single or multiple embodiments of signal interface processor elements which provide single or multiple output signals on output leads 25.16, 25.21 and 25.26 respectively.

FIG. 26 is an information monitoring processing and communication system. This system in certain application may include a patient monitor system. This information processing and transmission of diagnostics signals, other signals including DNA, fingerprint information and or photo or video clips for single and or multiple systems is implemented in this figure. Signal sources include single or multiple sources including one or more of sensors, probes or resultant signals from medical procedures or other procedure provided signals to one or more interface Units 26.1 to 26.6. The signal sources could contain one or more devices which provide signals from medical devices, sensors, probes or equipment, from diagnostics and or measurement of blood pressure, or other blood diagnostics, skin diagnostics, diagnostics of internal medicine information, body temperature, ECG, Electro Cardiogram or other sensors information signals obtained during surgery or post surgery arterial blood gas or heart pacemaker, glucose, MRI, fingerprint, other medical or diagnostics information signals, e.g. DNA or other sources, such as photo or video or sound signals or a combination of the signal sources. The signals and/or signal sources could also include: blood pressure or other blood diagnostics containing signals, urine, stool, skin signals ECG, glucose body temperature arterial blood gas sensor provided signals, signals containing DNA, fingerprint or photo or video signals and or video clip signals. During surgery and or post surgery sensors, probes and other medical devices are attached and or connected or inserted in parts of the body of a patient and these devices, in certain implementations are integrated into one product. The said product could include one or more or all the elements shown in FIG. 26 and such integrated product enables providing medical information containing signals by wireless means, instead the use of prior art cables and or other physical cumbersome devices. Units 26.7 to 26.11 are amplifier or signal processor or signal transformer devices or transducers, e.g. acoustical to electrical or pressure to electrical or chemical content to electrical signal transformers (transducers) and or merely interface points between the 26.1 to 26.6 signal sources and Unit 26.13. Unit 26.13 contains single or multiple processors and or single or multiple signal modulators for modulation and connection of one or more modulated signals to the single or multiple signal transmitters, Unit 26.14. Single or multiple signal transmitters 26.14 provide signals to one or more transmit interface output elements 26.15 and or 26.16. On reverse signal path 26.17 control and information signals are provided to various units of FIG. 26. The purpose of this reverse path control signals is to enable changing some of the processing means of signal parameters, signal transmission formats and methods and in certain medically authorized cases to change the medical treatment, e.g. quantity or speed of oxygen flow or of pain relievers, medication or other. The reverse control signal path may include a push to talk (PTT) option and in certain cases includes other sets of signals, e.g. an emergency physician's orders regarding patient's treatment in a mobile emergency vehicle, or orders for patient care at a remote facility.

FIG. 27 is a Universal System including one or multiple Remote Control or Universal Remote Control (URC) devices, including wireless door opener and or ignition starter, or window opener of an automobile or motor cycle or of other mobile devices, garage door or home door opener and or locking control, control of home or office appliances, turn off or turn on of computers or other wired or wireless devices, alarm systems and of other systems including monitoring devices and or directivity and or recording parameters of monitoring devices. Optional connection and or communication or control between devices, shown in FIG. 27 and Units shown in FIG. 16, and or other figures, e.g. medical devices shown in FIG. 26 is provided by wired or wireless connections 27.9. Unit 27.1 is an interface device and or a processor device and or sensor and or signal generator device and or a communication device for single or multiple signal transmission to and reception from single or multiple antennas 27.2. Unit 27.3 is a cellular phone (cellphone) and or other wireless or mobile or portable device containing signal interface units, processors, transmitters, receivers and connections to transmit and receive antennas (not shown in the figure) and providing/receiving signals on leads 27.4 containing audio and or television, radio or CD player and or video screen information, provided to or by Unit 27.5. Wired and or wireless connections 27.6 and 27.7 provide additional communication, processing and control means between units 27.3 and 27.5 and Unit 27.8. Unit 27.8 contains a Bluetooth or other wireless device. Unit 27.3 is equipped to provide signal repeater operations. The term signal repeater means that the repeater device processes and or amplifies the signal, received from an other transmitter; following reception of the transmitted signal, the signal is provided for processing and amplification for subsequent transmission.

Figure 28:
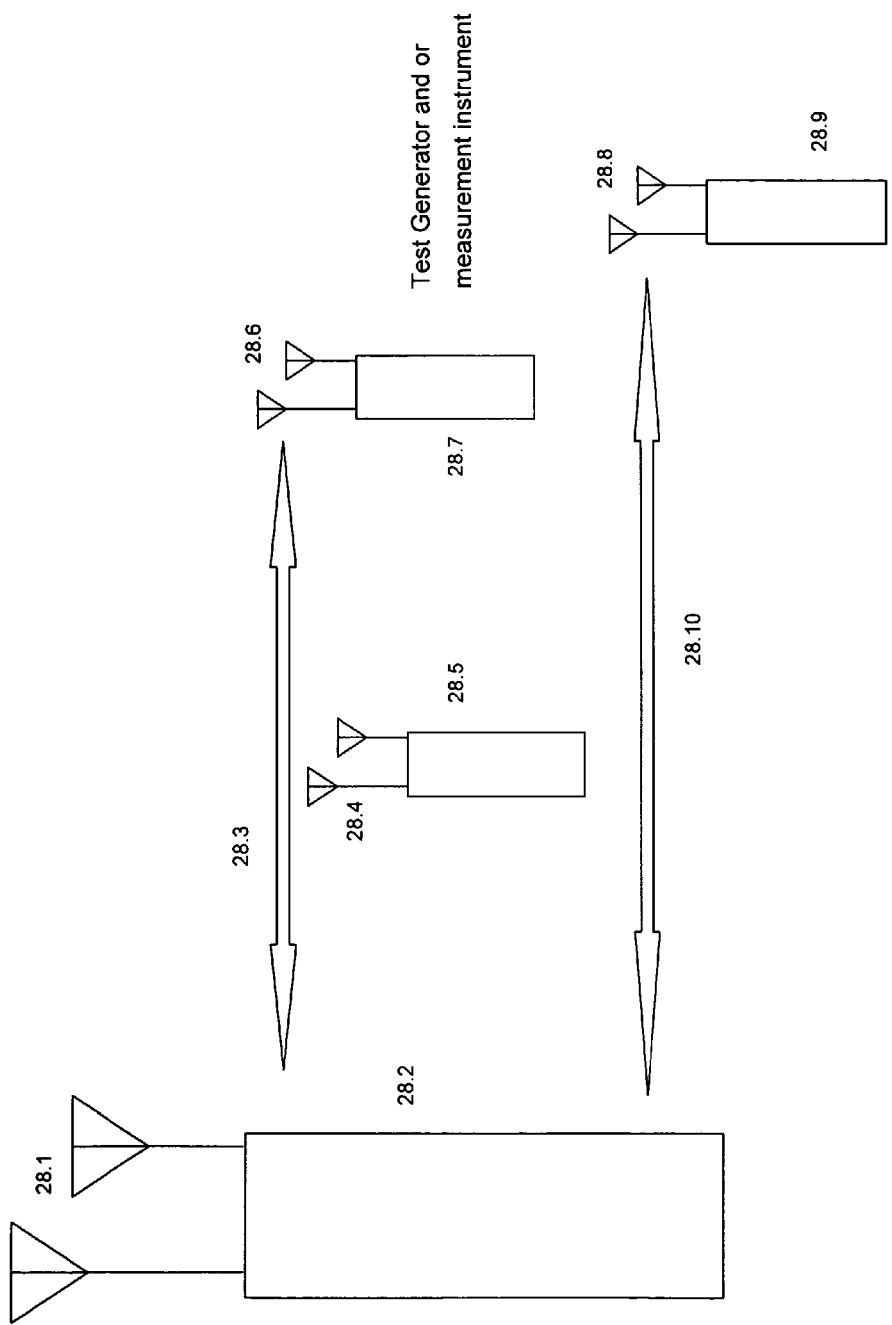
FIG. 28 shows a test and measurement instrumentation system within a wireless multi-mode system.

FIG. 28 is a test and measurement instrumentation system within a wireless multi-mode system. Single or plurality of antennas 28.1, 28.4, 28.6 and 28.8 receive/transmit signals from/to single or multiple transceivers 28.2, 28.5, 28.7 and 28.9 respectively. These transceivers are in certain cases parts of base station units and or of mobile units. Wired and or wireless connections 28.10 provide control and communications signals between one or more or all units shown in FIG. 28. Test signals are generated in Unit 28.9. These test signals are for performance measurement, testing and verification of one or multiple system performance parameters and or system specifications. In certain cases entire Unit 28.9 or parts of Unit 28.9 are implemented within Unit 28.2 and or 28.5 or 28.7.

Figure 29:
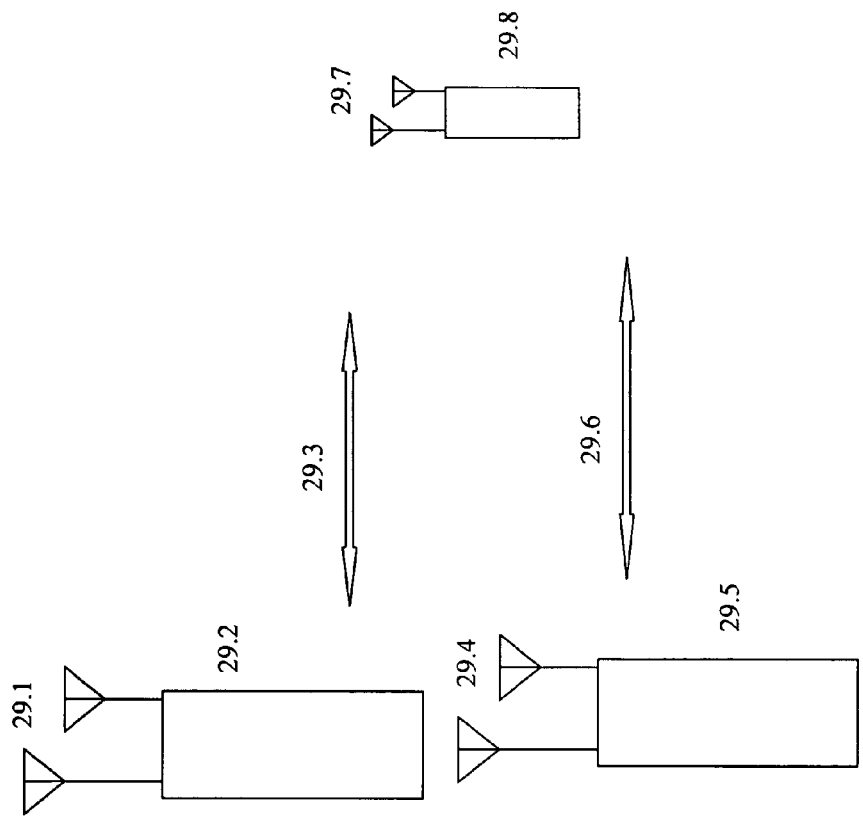
FIG. 29 is an implementation architecture of single or multiple cellular phones, or of other mobile devices, communicating with single or multiple Base Station Transceiver (BST) having single or plurality of antennas.

FIG. 29 is an implementation of single or multiple cellular phones, or of other mobile devices, communicating with single or multiple Base Station Transceiver (BST) having single or plurality of antennas. The BST are collocated in some of the implementations, while in others they are at different locations. Single or multiple antennas 29.1 and or 29.4 transmit and or receive signals to/from single or multiple BST 29.2 and 29.5. Unit 29.8 contains one or more cellular phones and or other wireless or other communication devices. Single or multiple antennas 29.7 receive and or transmit and connect signals to or from Unit 29.8, also designated here as the mobile unit. In one of the implementations BST 29.2 and or BST 29.5 contains one or more transmitters-receivers (T/R or transceivers) for WCDMA signals and or CDMA signals and or transceivers for GSM or GPRS and or EDGE signals and or OFDM signals or other spread spectrum signals. Unit 29.8 contains one or more transceivers. In some implementations mobile Unit 29.8 and or any of the BST units are connected in a repeater mode. The repeater mode is used to enhance signal coverage area by amplifying and retransmitting the received signal.

FIG. 30 shows a cardiac stimulation device, a heart and a block diagram of a single-chamber and or a dual-chamber pacemaker with a single or multiple wireless communications and control systems of the present invention. Exemplary prior art single-chamber pacemaker and/or dual-chamber pacemaker and implantable cardiac stimulation devices are described in U.S. Pat. No. 6,539,253 Thompson et al.: "Implantable medical device incorporating integrated circuit notch filters", issued Mar. 25, 2003 (for short "Thompson patent" or the "'253 patent" or "Thompson's '253 patent) and in U.S. Pat. No. 6,907,291 issued Jun. 14, 2005, Snell et al.: "Secure telemetry system and method for an implantable cardiac stimulation device", assigned to Pacesetter, Inc., Sylmar, Calif. (for short "Snell patent" or the "'291 patent" or "Snell's '291 patent"). The pacemaker and implantable cardiac stimulation device, of the current invention, is coupled to a heart 30.1 by way of leads 30.4*a* and 30.4*b*, lead 30.4*a* having an electrode 30.2 that is in contact with one of the atria of the heart, and lead 30.4*b* having an electrode 30.3 that is in contact with one of the ventricles of the heart. Leads 30.4*a* and 30.4*b* are connected to the pacemaker through a connection interface and or processor unit 30.5 that forms part of the pacemaker and implantable cardiac stimulation device. In certain other implementations and/or other applications, unit 30.1 contains other body parts or other body organs than the heart, for example unit 30.1 may be the kidney, limb, head, skin or a vessel while Unit 30.2 and Unit 30.3 a device or a medical probe or an other device than an electrode. Unit 30.6 contains single or multiple leads for connection of single or multiple signals between Unit 30.5 and 30.7. In certain embodiments unit 30.5 represents an interface connector or connection, and or some signal processing between leads 30.4*a* and 30.4*b* and Unit 30.7, while in other embodiments unit 30.5 contains a microprocessor for detection of signals received from Unit 30.7, for generation of control signals for the operation and/or modification of the parameters of the cardiac stimulation device-heart pacemaker, pulse generator, amplifiers, processors, memory sensors, battery and other components for the operation, control and modification of operating conditions of the pacemaker and or of other medical parameters. In some implementations Unit 30.5 contains stimulating pulse generators for atrial pulse generation and ventricular pulse generation, one or more detection circuits and amplifiers. One of the amplifiers, contained in Unit 30.5 is typically configured to detect an evoked response from the heart 30.1 in response to an applied stimulus, thereby aiding in the detection of "capture." Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue. Unit 30.5 of the current invention may contain a protection circuit for protecting the pacemaker from excessive shocks or voltages that could appear on the electrodes 30.2 and/or 30.3 in the event such electrodes were to come in contact with a high voltage signal, for example, from a defibrillation shock.

Unit 30.7 comprises one or more transmitters or receivers and/or transmitters and receivers, also known as transceivers (T/R), for transmission and or reception of one or multiple signals connected by leads 30.8 and or 30.11 to Unit 30.10 and or Unit 30.12. The single or multiple transceivers of Unit 30.7 contain in certain embodiments one or multiple modulation format selectable (MFS) and/or code selectable embodiments, such as previously described, e.g. GSM, WCDMA, spread spectrum, Bluetooth, Wi-Fi EDGE or other system specified modulation formats. In certain embodiments of Unit 30.7 there is at least one notch filter, also known as band stop filter, having an input and output that blocks predetermined Electromagnetic Interference (EMI) signals. Unit 30.10 contains interface circuitry and or connection circuitry-leads to one or multiple antennas 30.9. Unit 30.12 is an interface connection for transmission and or reception of signals.

In prior art pacemakers, e.g. Snell's '291 patent the pacemaker further includes magnet detection circuitry. It is the purpose of the magnet detection circuitry to detect when a magnet is placed over the pacemaker, which magnet may be used by a physician or other medical personnel to perform various reset functions of the pacemaker. The prior art pacemaker control requires magnet detection circuit for magnet controlled pacemaker parameters. Unfortunately this magnet dependent operation/change of parameters of pacemakers is in many cases causing difficulties and or even rendering impossible to have Magnetic Resonance Imaging (MRI), and/or Magnetic Resonance Image scanning on a patient who has a pace maker. Since MRI is a frequently desired diagnostic procedure for diagnostic purposes, even in an emergency where the information from the MRI scan could be life saving, and since MRI interferes with the correct operation of currently available magnetic detection-magnetic controlled based pacemakers, it would be highly desirable to develop a new generation of pacemakers which could be operated and controlled without substantial magnetic materials, i.e. without the need of magnet based detection and magnet control.

In distinction with the prior art magnet detection circuit and physician or other medical personnel performed various reset functions of the pacemaker, by placing a magnet over the pacemaker, in the current invention there is no need for magnet detection circuits and no need for magnet's to be placed over the pacemaker to reset or modify parameters and functions/operation of the pacemaker. In the current invention magnetic detection and magnet control of pacemaker is replaced by wireless signal detection and based on the detected wireless signals and processing of said wireless detected signals (received from a physician operated wireless transmitter) control signals are generated to control the parameters and operation of the pacemaker.

In distinction with the prior art and with Snell's '291 patent, the current invention provides new structures and embodiments of multiuse and/or multimode wired and or wireless transmitters and receivers, without need of magnetic coupling for adjusting or resetting the parameters of cardiac stimulation e.g. heart pacemaker devices and or other medical devices. An advantage of the presented embodiments is that the stimulation devices can continue to operate even in emergency rooms or other environments where the patient is having Magnetic Resonant Imaging (MRI) diagnostic tests.

Additional Description

Having now described numerous embodiments of the inventive structure and method in connection with particular figures or groups of figures, and having set forth some of the advantages provided by the inventive structure and method, we now highlight some specific embodiments having particular combinations of features. It should be noted that the embodiments described heretofore, as well as those highlighted below include optional elements or features that are not essential to the operation of the invention.

1. A first embodiment (1) is a location finder and communication system comprising: two or more antennas or receive ports for receiving location determining signals from two or more location determining transmitters; two or more receivers for processing of said location determining signal; a selector or combiner device for selection or combining of one or more of the received location determining signals; two or more communication transmitters; connection circuitry for connecting the selected or the combined processed location determining signal to one or more communication transmitters; a control and selection device for selection and connection of said location determining signals to one or more of said communication transmitters.

2. A second embodiment (2) provides a location finder and modulation-demodulation (modem) format selectable (MFS) and bit rate agile (BRA) communication system comprising: one or more receive ports for receiving location determining signals from one or more location determining transmitters; one or more receivers and demodulators for reception and demodulation of said location determining signals to baseband signals; a selector for selection of one or more of the baseband signals; connection circuitry for connecting the selected baseband signal to one or a plurality of transmitters; two or more communication transmitters; a baseband signal interface circuit for interfacing and receiving the selected baseband signal; a cross-correlator circuit for processing the baseband signal provided by said baseband interface circuit and for generation of cross-correlated baseband signals; a shaped Time Constrained Signal (TCS) wavelet processor and bit rate agile Long Response (LR) filter [structure] for providing shaped and filtered signals in in-phase and quadrature-phase baseband channels; a modulation-demodulation (modem) format selectable or code selectable baseband structure for providing either modem format selectable or code selectable cross-correlated processed and filtered in-phase and quadrature-phase baseband signals; a modulator for quadrature modulation of the in-phase and quadrature-phase baseband signals; one or more amplifiers comprising linear and/or nonlinear circuits for linear and/or non-linear amplification (NLA) of the modulated output signal of said quadrature modulator; and a switch or level controller for selecting linearly or non-linearly amplified (NLA) modulated signals.

3. A third embodiment (3) provides a location finding and communication system comprising: two or more receive ports for receiving either location finding signals and or other than location finding signals from either one or more location determining transmitters or from one or more other than location finding signal transmitters; one or more receivers and demodulators for receiving and demodulating said location finding signals to baseband signals; one or more receivers and demodulators for receiving and demodulating said other than location finding signals to baseband signals; a selector or combiner device for selection or combining of one or multiple baseband signals; two or more signal modulators; connection circuitry for connecting the selected or the combined single or multiple baseband signals to one or more of said signal modulators; a signal processing network for receiving the baseband signals from the connection circuitry and for providing cross-correlated in-phase and quadrature-phase baseband signals at a first specified bit rate; a signal processing network for receiving the selected or combined baseband signal and for providing a filtered signal at a second specified bit rate; and a selector for selecting either the cross-correlated signals, the filtered signal, or both the cross-correlated signals and the filtered signal; and connection for providing the selected signals to one or more modulators for signal modulation.

4. A fourth (4) implementation is a radio frequency identification (RFID) locator and communicator system comprising: one or more than one antennas for receiving Radio Frequency (RF) signals from one or more RFID and or location determining and or communication transmitters; one or more receivers and demodulators for reception and demodulation of said signals to baseband signals; a baseband signal processing network for receiving and processing said baseband signals; a cross-correlator circuit for cross-correlating said processed baseband signals and for generation of cross-correlated baseband signals; a shaped Time Constrained Signal (TCS) wavelet processor and bit rate agile Long Response (LR) filter structure for providing shaped and bit rate agile filtered signals in in-phase and quadrature-phase baseband channels; and a modulator for quadrature modulation of the in-phase and quadrature-phase baseband signals.

5. A fifth embodiment (5) is a Radio Frequency Identification (RFID) and communication system comprising a receiver for reception and demodulation of RFID transmitted signals to baseband signals; a cross-correlator for processing of said baseband signals for generation of cross-correlated in-phase and quadrature-phase baseband signals; and a modulator for quadrature modulation of the in-phase and quadrature-phase baseband signals.

6. A sixth embodiment (6) is a Radio Frequency Identification (RFID) and communication system, the improvement comprising: one or more receivers and one or more demodulators for reception and demodulation of RFID transmitted signals to baseband signals and for providing said baseband signals to a spread spectrum baseband processor and subsequent quadrature modulator for quadrature modulation of baseband spread spectrum signals and to a baseband filter and subsequent modulator for modulation of the said baseband filtered signal; and a connection circuit for providing either the spread spectrum modulated signal or the filtered modulated signal or both the modulated spread spectrum signal and the filtered modulated signals to one or more than one transmitters for transmission of the spread spectrum modulated and or the filtered modulated signals.

7. A seventh embodiment (7) is a location finder and Radio Frequency Identification (RFID) signal demodulation and modulation system comprising: one or more antennas for receiving modulated Radio Frequency (RF) location finder and or Radio Frequency Identification (RFID) signals from one or more than one location finder and or RFID transmitters; one or more receivers and demodulators for reception and demodulation of either said modulated RF or RFID signals to baseband signals; a signal processing network for receiving said baseband signals and for providing cross-correlated in-phase and quadrature-phase baseband signals at a first specified bit rate; a signal processing network for receiving said baseband signals and for providing a filtered signal at a second specified bit rate; a selector for selecting either the cross-correlated signals or the filtered signal or both the cross-correlated signals and the filtered signal; and a connection circuit for providing the selected signals to one or more modulators for signal modulation.

8. An eighth embodiment (8) comprises a location finder and communication system having two or more antennas for receiving modulated Radio Frequency (RF) location finder signals and communication signals from three or more location finder and communication system transmitters; two or more receivers and demodulators for reception and demodulation of said modulated RF signals to baseband signals; a signal processing network for receiving said baseband signals and for providing cross-correlated in-phase and quadrature-phase baseband signals at a first specified bit rate; a signal processing network for receiving said baseband signals and for providing a filtered signal at a second specified bit rate; a selector for selecting either the cross-correlated signals or the filtered signal or both the cross-correlated signals and the filtered signal; a connection circuit for providing the selected signals to one or more than one modulators for signal modulation; and a connection circuit for providing the modulated signals to two or more than two amplifiers and two or more than two antennas for amplification and transmission of the amplified modulated signals.

9. A ninth embodiment (9) provides a location finder and communication system comprising: one or more receive ports for receiving modulated location finder signals from one or more location finder and communication system transmitters; one or more receivers and demodulators for reception and demodulation of said modulated signals to baseband signals; a signal processing network for receiving said baseband signals and for providing cross-correlated in-phase and quadrature-phase baseband signals at a first specified bit rate; a first quadrature modulator for quadrature modulating the cross-correlated signal; a filter for filtering a second bit rate signal, said second bit rate signal having a different bit rate than the first bit rate signal, and providing a filtered baseband signal; a second modulator for modulating the filtered baseband signal; and switch circuitry for selecting and connecting either the cross-correlated first bit rate modulated signal or the filtered second bit rate modulated signal to a transmitter.

10. A tenth embodiment (10) is a barcode reader, location finder and communication system comprising: a barcode reader for reading bar-coded information and processing said bar-coded information into electrical signals; one or more receive ports for receiving modulated location finder signals from one or more location finder and communication system transmitters; one or more receivers and demodulators for reception and demodulation of said modulated signals to baseband signals; a signal processing network for receiving and processing said baseband signals and said bar-coded electrical signals and for providing in-phase and quadrature-phase baseband signals; a filter for filtering said baseband signals and said bar-coded electrical signals and for providing filtered baseband signals and said bar-coded electrical signals; a first quadrature modulator for quadrature modulating the in-phase and quadrature-phase baseband signals; a second modulator for modulating the said filtered baseband and said bar-coded electrical signals; and switch circuitry for selecting and connecting either the quadrature modulated or the filtered modulated signal to a transmitter.

11. An eleventh embodiment (11) is a stimulation device and communication system comprising: leads for carrying stimulation pulses to and or from one or more electrodes; a pulse generator configured to generate stimulation pulses and for providing said pulses by said leads to the electrodes; an interface circuit and/or processor for connection of said stimulation pulses to and/or from one or more wireless transmitter-receiver (T/R) circuits for transmission and/or reception of one or more wireless signals; and a control circuit coupled to one or more of said wireless transmitter-receiver circuits, said control circuit comprising a control signal generator for generating control signals for controlling operation parameters of the implantable cardiac stimulation device.

12. A twelfth embodiment (12) provides a cardiac stimulation and communication system comprising: a pulse generator and processor for processing the stimulation pulses to and/or from one or more electrodes, said electrodes located in a heart; a signal processing network for receiving said stimulation pulses and for providing cross-correlated in-phase and quadrature-phase baseband signals; a signal processing network for receiving said stimulation pulses and for providing a filtered baseband signal; and a selector for selecting either the cross-correlated signals or the filtered signal or both the cross-correlated signals and the filtered signal; and providing the selected signals to one or more modulators for signal modulation.

13. A thirteenth embodiment (13) provides an implantable cardiac stimulation and modulation system comprising: a processor for processing stimulation pulses to and/or from one or more electrodes; a signal processing network for receiving said stimulation pulses and for providing in-phase and quadrature-phase baseband signals; a signal processing network for receiving said stimulation pulses and for providing a filtered baseband signal; and a selector for selecting either the in-phase and quadrature-phase baseband signals or the filtered signal or both the in-phase and quadrature-phase baseband signals and the filtered signal; and providing the selected signals to one or more modulators for signal modulation.

14. A fourteenth embodiment (14) provides a medical diagnostic and communication system comprising: a processor for processing signals received from one or more medical diagnostic devices; a first signal processing network for receiving said processed signals and for providing in-phase and quadrature-phase baseband signals; a second signal processing network for receiving said processed signals and for providing a filtered baseband signal; and a selector for selecting either the in-phase and quadrature-phase baseband signals or the filtered baseband signal or both the in-phase and quadrature-phase baseband signals and the filtered signal; and providing the selected signals to one or more modulators for signal modulation.

15. A fifteenth embodiment (15) is a medical diagnostic and communication system comprising: a processor for processing signals received from one or more medical diagnostic devices; a first signal processing network for receiving said processed signals and for providing baseband signals having a first specified bit rate; a second signal processing network for receiving said processed signals and for providing baseband signals having a second specified bit rate; and a selector for selecting either the first specified bit rate signal or the second specified bit rate signal or both the first specified bit rate signal and the second specified bit rate signal; and providing the selected signals to one or more modulators for signal modulation.

16. A sixteenth embodiment (16) is a medical and diagnostic communication system, the improvement comprising: a transmitter of signals generated by a medical device; a receiver for reception and processing of said medical device generated signals to baseband signals; circuitry for processing said baseband signals for generation of in-phase and quadrature-phase spread spectrum baseband signals; and a modulator for quadrature modulation of the in-phase and quadrature-phase baseband spread spectrum signals.

17. A seventeenth embodiment (17) is a stimulation device and communication system comprising: leads for carrying stimulating pulses to and or from one or more electrodes; a pulse generator configured to generate stimulation pulses and for providing said pulses by said leads to the electrodes; an interface circuit and/or processor for connection of said stimulating pulses to and/or from one or more spread spectrum transmitter-receiver (T/R) circuits for transmission and/or reception of one or more spread spectrum signals; a control circuit coupled to one or more of said spread spectrum transmitter-receiver circuits and the said pulse generator and further arranged to process and detect one or more received signals; and said control circuit having a control signal generator for controlling the operation parameters of the stimulation device.

18. An eighteenth embodiment (18) provides a multiple modulator system comprising: a fingerprint sensor, detection, identification and processing device for processing one or multiple fingerprint information to activate one or multiple modulators for signal transmission; a location information receiver and processor for receiving and processing the location of the user; a processor device for processing and combining the location information and fingerprint information activated signals with an additional user signal, said user signal comprising a signal generated by a user and providing the processed signals to a first and or to a second modulator; a first modulator for spread spectrum encoding and modulating the processed baseband signals; a second modulator for filtering and modulating the processed baseband signals; a connection circuit for providing either the spread spectrum modulated signal or the filtered modulated signal or both the spread spectrum modulated signal and the filtered modulated signal to one or more transmitters for signal transmission.

19. A nineteenth embodiment (19) is a dual modulation transmitter apparatus comprising: a fingerprint sensor, detection, identification and processing device for processing one or multiple fingerprints to activate a modulator for signal transmission; a location information receiver and processor for receiving and processing the location of the user; a processor device for processing and combining the location information and fingerprint activated signals with additional user signals and providing the processed, baseband signals to a first and to a second modulator; a first modulator for spread spectrum encoding and modulating the processed baseband signals; a second modulator for filtering and modulating the processed baseband signals; a connection circuit for providing either the spread spectrum modulated signal or the filtered modulated signal or both the modulated spread spectrum signal and the modulated filtered signals to one or more antennas for signal transmission.

20. A twentieth embodiment (20) provides a multiple purpose system comprising: a fingerprint sensor, detection, identification and processing device for processing one or multiple fingerprints to activate one or multiple fingerprint generated signals for modulation and for signal transmission; a location information receiver and processor for receiving and processing the location of the user; a processor device for processing and combining the location information and fingerprint activated signals with additional user signals, said user signals comprising a signal generated by a user, and providing a processed baseband signal to a first and to a second modulator; a first modulator for quadrature modulating the processed baseband signals; a second modulator for filtering and modulating the processed baseband signals; a connection circuit for providing either the quadrature modulated signal or the filtered modulated signal or both the quadrature modulated signal and the modulated filtered signals to one or more antennas for signal transmission.

21. A twenty-first embodiment (21) is a multiple path transmitter system comprising: a fingerprint sensor, detection, identification and processing device for processing one or multiple fingerprints to activate one or multiple modulators for signal transmission; a location information receiver and processor for receiving and processing the location of the user; a processor device for processing and combining the location information and fingerprint activated signals with additional user signals and providing the processed, baseband signals to a first and to a second modulator; a first modulator cross-correlating and for quadrature modulating the processed baseband signals; a second modulator for filtering and modulating the processed baseband signals; a connection circuit for providing either the quadrature modulated signal or the filtered modulated signal or both the quadrature modulated signal and the modulated filtered signals to one or more antennas for signal transmission.

22. A twenty-second embodiment (22) provides a multiple modulator system comprising: a fingerprint sensor, detection, identification and processing device for processing one or multiple fingerprint information to activate one or multiple modulators for signal transmission; a location information receiver and processor for receiving and processing the location of the user; a processor device for processing and combining the location information and fingerprint information activated signals with an additional user signal, said user signal comprising a signal generated by a user and providing the processed signals to a first and to a second modulator; a first modulator cross-correlating and for quadrature modulating the processed signals; a second modulator for filtering and modulating the processed signals; a connection circuit for providing either the quadrature modulated signal or the filtered modulated signal or both the quadrature modulated signal and the modulated filtered signals to two or more transmitters for signal transmission.

23. A twenty-third embodiment (23) is a multi path communication apparatus comprising: a user detection and authentication device for identifying a user, processing the detected authentication identification of the user, and generating authentication information signals; a first signal path including a modulator coupled to said information signals and to an other user generated input signal, said input signal comprising a signal generated by a user; a second signal path including a cross-correlator for generation of in-phase (I) and quadrature-phase (Q) cross-correlated baseband signals from said information signals and or from said user generated signals, and a quadrature modulator coupled to said cross-correlated baseband signals; a third signal path coupled to a transmitter; and a switch or combiner configured to couple the third signal path to the first signal path under a first condition, to couple the third signal path to the second signal path under a second condition, or to couple the third signal path to both the first signal path and the second signal path under a third condition.

24. A twenty-fourth embodiment (24) is system comprising: a user detection and authentication device for identifying a user, processing the detected authentication identification of the user, and generating authentication information signals; a first signal path including a modulator coupled to said information signals and to an other user generated input signal, said input signal comprising a signal generated by a user; a second signal path including a quadrature modulator coupled to said information and or other user generated signal; and a switch or combiner configured to couple the first signal path under a first condition, or the second signal path under a second condition, or the third signal path under a third condition to the transmitter for signal transmission.

The invention further provides methods and procedures performed by the structures, devices, apparatus, and systems described herein before, as well as other embodiments incorporating combinations and subcombinations of the structures highlighted above and described herein.

All publications including patents, pending patents and reports listed or mentioned in these publications and/or in this patent/invention are herein incorporated by reference to the same extent as if each publication or report, or patent or pending patent and/or references listed in these publications, reports, patents or pending patents were specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A mobile device comprising:
a cross-correlator, transmit baseband filter and first modulator, for cross-correlating a first bit rate signal into a cross-correlated in-phase and quadrature-phase signal, filtering, modulating and providing said cross-correlated modulated signal to a first transmitter;
a Orthogonal Frequency Division Multiplex (OFDM) processor for processing a second bit rate signal, received from internet, and providing processed OFDM signal to a second modulator for modulation and for connection to a second transmitter;

a transmission system comprising said first and second transmitter for wireless transmission of said cross-correlated and OFDM modulated signal wherein, said OFDM processor and said cross-correlator are in said mobile device and said transmission system is controlled by a signal generated by touching the screen of said mobile device;

a diversity receiver system comprising a first and a second receiver for receiving a Radio Frequency (RF) modulated signal and for providing said received RF signal to a first demodulator; and said first demodulator, receive baseband filter and receive processor for demodulation, filtering and processing said RF signal, wherein said receive baseband filter for filtering is intentionally mis-matched to said transmit baseband filter for filtering and said receive filter provides received baseband mis-matched filtered cross-correlated in-phase and quadrature-phase signal; and a third receiver and second demodulator for receiving and demodulating location finder modulated transmitted signal to demodulated baseband location finder signal.

2. A system comprising:

a first processor and transmit baseband filter for processing and filtering internet provided signal into a first bit rate cross-correlated in-phase and quadrature-phase filtered Time Division Multiple Access (TDMA) signal and into a second bit rate cross-correlated spread spectrum in-phase and quadrature-phase baseband signal and providing the first and second bit rate signal to a modulator for modulation, wherein first and second rates are distinct rates;

a modulator for modulation of said TDMA or said spread spectrum cross-correlated signal and for providing said modulated signal to a transmitter for transmission of the modulated signal;

a receiver and first demodulator system for receiving and demodulating a transmitted modulated signal;

said first demodulator system comprising a demodulator, baseband receiver filter and a second processor for demodulation, filtering and processing said transmitted modulated signal, wherein said receiver baseband filter, used for filtering of the first bit rate cross-correlated filtered signal, is mis-matched to said transmit baseband filter and said receiver filter provides cross-correlated filtered in-phase and quadrature-phase signal;

a receiver, second demodulator and third processor for receiving, demodulating and processing location finder modulated transmitted signals to demodulated processed baseband location finder signals; and a fourth processor for processing said processed baseband location finder signals with said processed cross-correlated TDMA signals and for providing processed location finder signals with said processed TDMA cross-correlated signals to a modulator for modulation of the processed location finder signals with said processed cross-correlated signals.

3. A system comprising:

a processor and transmit baseband filter for processing and filtering an internet provided signal into a first bit rate time division multiplexed (TDM) filtered signal and a second bit rate Orthogonal Frequency Division Multiplexed (OFDM) processed signal and for providing said processed TDM filtered signal to a first modulator and said OFDM processed signal to a second modulator for modulation and for providing modulated TDM and OFDM signal to a transmission system for transmission of the modulated signal;

a transmission system comprising two distinct transmitters for transmission of the modulated signal;

a receiver and first demodulator system for receiving and demodulating a transmitted modulated signal;

a first demodulator system comprising a demodulator, baseband receive filter and a processor for demodulation, filtering and processing said transmitted signal, wherein said baseband receive filter is mis-matched to said transmit baseband filter used for filtering of said first bit rate TDM filtered signal;

a receiver, second demodulator and a processor for receiving, demodulating and processing a location finder modulated transmitted signal to a demodulated processed baseband location finder signal;

a processor for processing said processed baseband location finder signal with said processed TDM signal and for providing processed location finder signal with processed TDM signal to a modulator for modulation of the processed location finder signal with said processed TDM signal; and a processor for receiving and processing a fingerprint and a touch screen generated signal for user authentication and for touch screen control and operation of said transmitters.

4. The system of claim 1, wherein said second bit rate signal received from internet is a Video over Internet Protocol (ViIP) or video over intranet signal and further comprising a non-quadrature modulator for polar modulation of a camera generated signal in a cellular system and a processor and filter for processing and providing a processed and filtered first bit rate cross-correlated in-phase and quadrature-phase spread spectrum signal, for providing a second bit rate cross-correlated in-phase and quadrature-phase spread spectrum signal and a third bit rate cross-correlated in-phase and quadrature-phase Time Division Multiple Access (TDMA) signal, wherein said first and second bit rate spread spectrum signals are used in distinct cellular systems and wherein said received location finder information signals are received from a cellular system and from a Global Positioning System (GPS) satellite system and comprising a connector for providing a voice signal from a wire.

5. The system of claim 1 wherein said location finder modulated transmitted signal is a signal used in navigation systems and further comprising a video processor for receiving and processing a video signal for providing a processed filtered video cross-correlated in-phase and quadrature-phase filtered baseband signal to a quadrature modulator and comprising a processor and filter for processing and providing a processed photo camera generated filtered cross-correlated in-phase and quadrature-phase spread spectrum signal, for providing a Radio Frequency Identification (RFID) device generated cross signal.

6. The system of claim 1 wherein said cross-correlator is a cross-correlator used in Global Mobile System (GSM) for cross-correlating GSM in-phase and quadrature-phase signals.

7. The system of claim 1 wherein transmitter of first bit rate modulated signal comprises a transmitter operated as a Non-Linearly Amplified (NLA) transmitter and transmitter of second bit rate modulated signal comprises a transmitter operated as a linearly amplified or linearized amplifier transmitter.

8. The system of claim 1 wherein said OFDM signal is a wireless fidelity (Wi-Fi) signal specified or recommended in one or more IEEE standard.

9. The system of claim 2 wherein said spread spectrum signal is Code Division Multiple Access (CDMA) signal.

10. The system of claim 2 wherein said receiver comprises a receive antenna diversity system and further comprising a radio frequency (RF) head end which is located at a remote location from said mobile device and further comprising a non-quadrature modulator for polar modulation of a camera generated signal in a cellular system and a processor and filter for processing and providing a processed and filtered cross-correlated in-phase and quadrature-phase spread spectrum signal, and for providing a cross-correlated in-phase and quadrature-phase TDMA signal, wherein said spread spectrum cross-correlated signal and said TDMA cross-correlated signal is used in distinct cellular systems and further comprising a connector for connecting a wire provided control signal to said mobile device for wired signal control of said mobile device.

11. The system of claim 2 wherein said receiver comprises a radio frequency (RF) head end which is located at a remote location from the intermediate frequency (IF) or from the baseband parts of the diversity receiver and further comprising a video processor for receiving and processing a video signal for providing a processed filtered video cross-correlated in-phase and quadrature-phase filtered baseband signal to a quadrature modulator and comprising a processor and filter for processing and providing a processed photo camera generated filtered cross-correlated in-phase and quadrature-phase spread spectrum signal and comprising a receiver and processor for a fingerprint generated signal for user identification of said mobile device.

12. The system of claim 2 wherein said transmitter for transmission of the modulated signal for first bit rate signal is operated as a Non-Linearly Amplified (NLA) transmitter and transmitter of second bit rate modulated signal comprises a transmitter operated as a linearly amplified or linearized amplifier transmitter.

13. The system of claim 3 wherein said first bit rate time division multiplexed (TDM) signal is a cross-correlated in-phase and quadrature-phase filtered signal.

14. The system of claim 3 wherein said TDM modulated signal is provided to a Non-Linearly Amplified (NLA) transmitter and the OFDM modulated signal to a transmitter operated as a linearly amplified or linearized amplifier transmitter.

15. The system of claim 3 wherein said receiver comprises a receive antenna diversity system.

16. The system of claim 3 wherein said receiver comprises a radio frequency (RF) head end which is located at a remote location from the intermediate frequency (IF) or from the baseband parts of said receiver.

17. The system of claim 3 wherein said transmission system comprising two distinct transmitters for transmission of the modulated signal comprises a Non-Linearly Amplified (NLA) transmitter and a linearly amplified or linearized amplifier transmitter.

18. A mobile device comprising:

a receiver, demodulator and processor for receiving, demodulating and processing an internet provided Orthogonal Frequency Division Multiplex (OFDM) modulated signal, a Global Positioning System (GPS) satellite system provided modulated signal, a Radio Frequency Identification (RFID) system provided modulated signal, a cellular system provided Code Division Multiple Access (CDMA) modulated signal and a cellular system provided Time Division Multiple Access (TDMA) modulated signal into demodulated and processed OFDM, GPS, RFID, CDMA and TDMA baseband signal, wherein, said receiver and demodulator is part of a mobile device and said TDMA modulated signal comprises a video signal and said demodulator provides quadrature demodulated baseband cross-correlated in-phase and quadrature-phase signal;

a body temperature sensor and processor for sensing and processing the body temperature of a user of said mobile device into a processed body temperature signal for providing said processed body temperature signal to a polar modulator and a transmitter for non-quadrature modulation and transmission of said processed body temperature signal;

a screen, a touch screen detector and a processor for touching the screen of said mobile device for generating, detecting, receiving and processing a touch screen generated signal into processed touch screen control signal, wherein said control signal is used for control of connection of one or more of said demodulated and processed signal to a user interface unit;

a Multiple Input Multiple Output (MIMO) system comprising a processor and filter processing a received location finder signal from cellular base stations, processing and filtering a received voice signal, providing a processed voice filtered baseband signal and connecting said received processed cellular base station location finder signal combined with said processed voice signal to a non-quadrature modulator for non-quadrature modulation of said processed voice signal;

a processor for processing a camera generated signal and for providing a processed camera generated signal, a processor and a connector for processing and connecting said processed location finder signal combined with said processed camera generated signal to quadrature OFDM modulator for quadrature modulation of said processed signal;

a connector for connecting said non-quadrature and said quadrature modulated signal to a transmitter;

a signal transmitter for transmission of said non-quadrature and quadrature modulated signal, wherein said transmitter comprises multiple antennas and wherein said signal transmitter for transmission is controlled by a signal generated by touching the screen of a device; and a Radio Frequency (RF) receiver for reception of one or more transmitted modulated signals, wherein said RF receiver comprises multiple antennas.

19. A cellular phone comprising:

a receiver for receiving and processing an internet provided Orthogonal Frequency Division Multiplex (OFDM) modulated signal, a Global Positioning System (GPS) satellite system provided modulated signal, a sensor system provided modulated signal, a cellular system provided Code Division Multiple Access (CDMA) modulated signal and a cellular system provided Time Division Multiple Access (TDMA) modulated signal into processed OFDM, GPS, sensor, CDMA and TDMA signal, wherein, said receiver is part of a Software Defined Radio (SDR) cellular device and said OFDM modulated signal comprises a video signal;

a fingerprint detector and processor for detecting and processing fingerprint of a user of said cellular phone into a processed fingerprint authentication signal for providing said processed fingerprint authentication signal to an interface unit of said cellular phone and to a non-quadrature modulator and a transmitter for non-quadrature modulation and transmission of said processed fingerprint authentication signal;

a screen, a touch screen detector and a processor for touching the screen of said cellular phone for generating a touch screen generated signal, detecting and processing said touch screen generated signal into processed touch screen control signal wherein said control signal is used for control of connection of one or more of said processed OFDM, GPS, sensor, CDMA and TDMA signal to an interface unit of said user;

a non-quadrature modulator for non-quadrature modulation of a camera generated signal in a cellular system;

a processor and filter for processing and providing a processed and filtered cross-correlated in-phase and quadrature-phase video spread spectrum signal, and for providing a cross-correlated in-phase and quadrature-phase TDMA signal, wherein said spread spectrum cross-correlated signal and said TDMA cross-correlated signal is used in distinct cellular systems; and a motion detector for detection of motion of said cellular phone.

* * * * *